(12) United States Patent
Williams

(10) Patent No.: US 10,144,935 B2
(45) Date of Patent: Dec. 4, 2018

(54) DNA PLASMIDS WITH IMPROVED EXPRESSION

(71) Applicant: Nature Technology Corporation, Lincoln, NE (US)

(72) Inventor: James A. Williams, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 0 days.

(21) Appl. No.: 15/375,215

(22) Filed: Dec. 12, 2016

(65) Prior Publication Data
US 2017/0088844 A1   Mar. 30, 2017

Related U.S. Application Data

(62) Division of application No. 14/422,865, filed as application No. PCT/US2013/000068 on Mar. 14, 2013, now Pat. No. 9,550,998.

(60) Provisional application No. 61/743,219, filed on Aug. 29, 2012.

(51) Int. Cl.
| | |
|---|---|
| *C12N 15/63* | (2006.01) |
| *C12N 15/85* | (2006.01) |
| *C12N 15/70* | (2006.01) |
| *A61K 39/00* | (2006.01) |
| *A61K 48/00* | (2006.01) |

(52) U.S. Cl.
CPC ........... *C12N 15/635* (2013.01); *C12N 15/70* (2013.01); *C12N 15/85* (2013.01); *A61K 39/00* (2013.01); *A61K 48/00* (2013.01); *C12N 2800/107* (2013.01); *C12N 2820/55* (2013.01)

(58) Field of Classification Search
None
See application file for complete search history.

(56) References Cited

U.S. PATENT DOCUMENTS

| | | | |
|---|---|---|---|
| 5,922,583 | A | 7/1999 | Morsey |
| 6,977,174 | B2 | 12/2005 | Crouzel et al. |
| 7,244,609 | B2 | 7/2007 | Drocourt et al. |
| 7,279,313 | B2 | 10/2007 | Soubrier |
| 7,611,883 | B2 | 11/2009 | Cranenburgh |
| 7,807,444 | B2 | 10/2010 | Soubrier |
| 7,943,377 | B2 | 5/2011 | Carnes et al. |
| 2003/0161844 | A1 | 8/2003 | Soubrier |
| 2006/0063232 | A1 | 3/2006 | Grabherr et al. |
| 2007/0015282 | A1 | 1/2007 | Soubrier |
| 2007/0141708 | A2 | 6/2007 | Soubrier |
| 2006/9007535 | | 3/2009 | Snyder |
| 2009/0252713 | A1 | 10/2009 | Soubrier |
| 2010/0184158 | A1 | 7/2010 | Williams |
| 2010/0303859 | A1 | 12/2010 | Williams |

FOREIGN PATENT DOCUMENTS

| | | |
|---|---|---|
| GB | 2214508 A | 6/1989 |
| WO | 2004033664 A2 | 4/2004 |
| WO | 2006029449 A1 | 3/2006 |
| WO | 2008153733 A2 | 12/2008 |
| WO | 2009025690 A2 | 2/2009 |

OTHER PUBLICATIONS

A. Duilio et al.; Molecular Characterization of a Recombinant Replication Protein (Rep) from the Antarctic *Bacterium psychrobacter* sp. TA144; FEMS Microbiology, V 198, p. 49-55.
Nature Technology Corporation: "Targeting RIG-I activating Expression Vectors", Instruction Manual, vol. version 1, Sep. 1, 2011 (Sep. 1, 2011), XP002713690.
Abhyankar et al., Biochemical Investigations of Control of Replication Initiation of Plasmid R6K*, Journal of Biological Chemistry. vol. 279. No. 8, pp. 6711-6719, 2004.
Abhyankar et al., "Reconstitution of R6K replication in Vitro Using 22 Purified Proteins", The Journal of Biological Chemistry, vol. 278. No. 46, pp. 45476-45484, 2003.
Angulo et al., "Identification of a Boundary Domain Adjacent to the Potent Human cytomegalovirus Enhancer That Represses Transcription of the Divergent UL127 Promoter" Journal of Virology, Mar. 2000, p. 2826-2839.
Ashfield et al. "MAZ-dependent termination between closely spaced human complement genes" The EMBO Journal vol. 13 No. 23 pp. 5656-5667, 1994.
Barouch et al. "A Human T-Cell Leukemia Virus Type 1 Regulatory Element Enhances the Immunogenicity of Human Immunodeficiency Virus Type 1 DNA Vaccines in Mice and Nonhuman Primates" Journal of Virology, Jul. 2005, pp. 8828-8834 2005.
Carnes "Fermentation Design for the Manufacture of Therapeutic Plasmid DNA" Bioprocess International, pp. 2-7, Oct. 2005.
Chenna et al. "Multiple sequence alignment with the Clustal series of programs" Nucleic Acids Research, vol. 31, No. 13, pp. 3497-3500, 2003.
Del Solar et al., "Replication and Control of Circular Bacterial Plasmids", Microbiology and Molecular Biology Reviews, vol. 62, No. 2, pp. 434-464, Jun. 1998.
Franch and Gerdes "U-turns and regulatory RNAs" Current Opinion in Microbiology, 3:159-164, 2000.
Garg et al. "The Hybrid Cytomegalovirus Enhancer/Chicken b-Actin Promoter along with Woodchuck Hepatitis Virus Posttranscriptional Regulatory element Enhances the Protective Efficacy of DNA Vaccines" The Journal of Immunology pp. 550-558, 2004.
Hebel et al. "Challenges in the process development of a novel Zero-CpG CFTR plasmid for human clinical use" VGX Pharmaceuticals, Inc., (1 page), 2008.
Hiraga et al., "Comparative analysis of the replicon regions of eleven ColE2-related plasmids" Journal of Bacteriology, vol. 17, No. 23, pp. 7233-7243, 1994.

(Continued)

*Primary Examiner* — Nancy A Treptow
(74) *Attorney, Agent, or Firm* — Harness, Dickey & Pierce, P.L.C.

(57) ABSTRACT

The present invention relates to the production and use of covalently closed circular (ccc) recombinant plasmids, and more particularly to vector modifications that improve expression of said DNA molecules in the target organism.

7 Claims, 12 Drawing Sheets
Specification includes a Sequence Listing.

(56) References Cited

OTHER PUBLICATIONS

Kim et al. "Improved Mammalian Expression Systems by Manipulating Transcriptional Termination Regions" Biotechnol. Prog. vol. 19, No. 5. p. 1620-1622, 2003.
Lu et al. "The Extragenic Spacer Length Between the 5' and 3' Ends of the Transgene Expression Cassette Affects Trangene Silencing from Plasmid-based Vectors" Molecular Therapy, pp. 1-9, 2012.
Luke et al. "Improved antibiotic-free DNA vaccine vectors utilizing a novel RNA based plasmid selection system" Vaccine 27, pp. 6454-6459, 2009.
Luke et al. "Vector Insert-Targeted Integrative Antisense Expression System for Plasmid Stabilization" Mol. Biotechnol., (7 pages), 2010.
Manoj et al. "Approaches to Enhance the Efficacy of DNA Vaccines" Critical Reviews in Clinical Laboratory Sciences, 41(1), pp. 1-39, 2004.
Marians et al. "Maximal Limits of the *Excherichia coli* Replication Factor Y Effector Site Sequences in pBR322 DNA" The Journal of Biological Chemistry, vol. 247, No. 10, pp. 5656-5662, May 1982.
Masai et al. "The ABC-Primosome—A Novel Priming System Employing dnaA, dnaB, dnaC, and Primase on a Hairpin Containing a dnaA Box Sequence" The Journal of Biological Chemistry, vol. 265, No. 25, pp. 15134-15144, Sep. 1990.
Masai et al. "Roles of øX174 Type Primosome- and G4 Type Primase-dependent Primings in Initiation of Lagging and Leading Strand Syntheses of DNA Replication" The Journal of Biological Chemistry, vol. 265, No. 25, pp. 15124-15133, Sep. 1990.
Mutalik et al. "Rationally designed families of orthogonal RNA regulators of translation" Nature Chemical Biology, pp. 1-8, Mar. 2012.
Na et al. "Metabolic engineering of *Escherichia colii* using synthetic small regulatory RNAs" Nature Biotechnology, pp. 1-7, 2013.
Nomura et al. "Identification of eleven single-strand initiation sequences (ssi) for priming of DNA replication in the F, R6K, R100 and ColE2 plasmids" Gene, 108 (1991) 15-22.
Sato et al. "A Specific DNA Sequence Controls Termination of Transcription in the Gastrin Gene" Molecular and Cellular Biology, vol. 6, No. 4, pp. 1032-1043, Apr. 1986.
Soubrier et al. "pCOR: a new design of plasmid vectors for nonviral gene therapy" Gene Therapy, (1999)6, pp. 1482-1489.
Takechi et al. "Control of ColE2 plasmid replication: regulation of Rep expression by a plasmid-coded antisense RNA", Mol Gen Genet (1994) 244: pp. 49-56.
Wagner et al. "Antisense RNAs in Bacteria and Their Genetic Elements" Advances in Genetics, vol. 46, pp. 361-398, 2002.
Wilson et al. "Importance of Structural Differences between Complementary RNA Molecules to Control of Replication of an IncB Plasmid" Journal of Bacteriology, vol. 179, No. 3, pp. 742-753, Feb. 1997.
Wu et al. "A DNA Segment conferring Stable Maintenance on R6K y-Origin Core Replicons" Journal of Bacteriology, vol. 177, No. 22, pp. 6338-6345, Nov. 1995.
Yagura et al. "The Rep protein binding elements of the plasmid ColE2-P9 replication origin" Biochemical and Biophysical Research Communications, vol. 345, pp. 872-877, 2006.
Yagura et al. "Anatomy of the Replication Origin of Plasmid ColE2-P9" Journal of Bacteriology, vol. 188, No. 3, pp. 999-1010, Feb. 2006.
Bailone et al. "Nucleotide sequence of the operators of I ultravirulent mutants" Nucleic Acids Research vol. 8, No. 10, 1980.
Datsenko et al. "One-step inactivation of chromosomal genes in *Excherichia coli* K-12 using PCR products" PNAS, vol. 97, No. 12, pp. 6640-6645, 2000.
Nagase et al. "Essential elements in the coding region of mRNA for translation of ColE2 Rep protein" Plasmid 59, pp. 36-44, 2008.
Haldimann et al. "Conditional-Replication, Integration, Excision, and Retrieval Plasmid-Host Ssytems for Gene Structure-Function Studies of Bacteria" Journal of Bacteriology, vol. 183, No. 21, pp. 6384-6393, 2001.
Han et al. "The ColE2-P9 Rep protein binds to the origin DNA as a monomer" Biochemical and Biophysical Research Communications 353, pp. 306-310, 2007.
Kay et al. "A robust system for production of minicircle DNA vectors" Nature Biotechnology 28, pp. 1287-1289, 2010.
Lieb M. "Heat-Sensitive Lambda Repressors Retain Partial Activity During Bacteriophage Induction" Journal of Viroloty, vol. 32, No. 1, pp. 162-166, 1979.
Lanza et al. "Global Strain Engineering by Mutant Transcription Factors" Methods in Molecular Biology, vol. 765, pp. 253-274, 2011.
Lissemore et al. "Green Fluorescent Protein as a Quantitative Reporter of Relative Promoter Activity in *E. coli*" Biotechniques, vol. 28, No. 1, 2000.
Luke et al. "Coexpressed RIG-1 Agonist Enhances Humoral Immune Response to Influenza Virus DNA Vaccine" Journal of Virology, vol. 85, No. 3, pp. 1370-1383, 2011.
Metcalf et al. "Use of the rep technique for allele replacement to construct new *Escherichia coli* hosts for maintenance of R6Kg origin plasmids at different copy numbers" Gene Therapy vol. 138, pp. 1-7, 1994.
Wang et al. "Construction and analysis of compact muscle-specific promoters for AAV vectors" Gene Therapy 15, pp. 1489-1499, 2008.
Yasueda et al. "Structural and functional organization of ColE2 and ColE3 replicons" Mol Gen Genet 215, pp. 209-216, 1989.
Yasueda et al. "Control of ColE2 plasmid replication: negative regulation of the expression of the plasmid-specified initiator protein, Rep, at a posttranscriptional step" Mol Gen Genet 244, pp. 41-48, 1994.
Zhao et al. "Transfection of shRNA-encoding Minivector DNA of a few hundred base pairs to regulate gene expression in lymphoma cells" Gene Therapy 18, pp. 220-224, 2011.
Benson et al., "DNA Sequence Determinants of λ Repressor Binding in Vivo", Genetics, vol. 188, Jan. 1988, pp. 21-29.

SEQUENCE LISTING

```
<160> NUMBER OF SEQ ID NOS: 44

<210> SEQ ID NO 1
<211> LENGTH: 281
<212> TYPE: DNA
<213> ORGANISM: Artificial Sequence
<220> FEATURE:
<223> OTHER INFORMATION: Description of Artificial Sequence: R6K gamma
      Origin

<400> SEQUENCE: 1
ggcttgttgt ccacaaccgt taaaccttaa aagctttaaa agccttatat attcttttt      60 ttcttataaa acttaaaacc ttagaggcta tttaagttgc tgatttatat taatttatt    120 gttcaaacat gagagcttag tacgtgaaac atgagagctt agtacgttag ccatgagagc   180
ttagtacgtt agccatgagg gtttagttcg ttaaacatga gagcttagta cgttaaacat   240
gagagcttag tacgtactat caacaggttg aactgctgat c                       281

<210> SEQ ID NO 2
<211> LENGTH: 1667
<212> TYPE: DNA
<213> ORGANISM: Artificial Sequence
<220> FEATURE:
<223> OTHER INFORMATION: Description of Artificial Sequence: NTC9385R
      vector backbone

<400> SEQUENCE: 2
ccgcctaatg agcgggcttt ttttggctt gttgtccaca accgttaaac cttaaaagct     60
ttaaaagcct tatatattct ttttttctt ataaaactta aaaccttaga ggctatttaa    120
gttgctgatt tatattaatt ttattgttca aacatgagag cttagtacgt gaaacatgag   180
agcttagtac gttagccatg agagcttagt acgttagcca tgagggttta gttcgttaaa   240
catgagagct tagtacgtta aacatgagag cttagtacgt actatcaaca ggttgaactg   300
ctgatccacg ttgtggtaga attggtaaag agagtcgtgt aaaatatcga gttcgcacat   360
cttgttgtct gattattgat ttttggcgaa accatttgat catatgacaa gatgtgtatc   420
taccttaact taatgatttt gataaaaatc attaggtacc ccggctctag ttattaatag   480
taatcaatta cggggtcatt agttcatagc ccatatatgg agttccgcgt tacataactt   540
acggtaaatg gcccgcctgg ctgaccgccc aacgaccccc gcccattgac gtcaataatg   600
acgtatgttc ccatagtaac gccaataggg actttccatt gacgtcaatg ggtggagtat   660
ttacggtaaa ctgcccactt ggcagtacat caagtgtatc atatgccaag tacgccccct   720
attgacgtca atgacggtaa atggcccgcc tggcattatg cccagtacat gaccttatgg   780
gactttccta cttggcagta catctacgta ttagtcatcg ctattaccat ggtgatgcgg   840
ttttggcagt acatcaatgg gcgtggatag cggtttgact cacggggatt tccaagtctc   900
caccccattg acgtcaatgg gagtttgttt tggcaccaaa atcaacggga ctttccaaaa   960
tgtcgtaaca actccgcccc attgacgcaa atgggcggta ggcgtgtacg gtgggaggtc  1020
tatataagca gagctcgttt agtgaaccgt cagatcgcct ggagacgcca tccacgctgt  1080
```

```
tttgacctcc atagaagaca ccgggaccga tccagcctcc gcggctcgca tctctccttc   1140
acgcgcccgc cgcccctacct gaggccgcca tccacgccgg ttgagtcgcg ttctgccgcc   1200
tcccgcctgt ggtgcctcct gaactgcgtc cgccgtctag gtaagtttaa agctcaggtc   1260
gagaccgggc ctttgtccgg cgctcccttg gagcctacct agactcagcc ggctctccac   1320
gctttgcctg accctgcttg ctcaactcta gttctctcgt taacttaatg agacagatag   1380
aaactggtct tgtagaaaca gagtagtcgc ctgcttttct gccaggtgct gacttctctc   1440
ccctgggctt ttttcttttt ctcaggttga aagaagaag acgaagaaga cgaagaagac   1500
aaaccgtcgt cgacagatct ttttccctct gccaaaaatt atggggacat catgaagccc   1560
cttgagcatc tgacttctgg ctaataaagg aaatttattt tcattgcaat agtgtgttgg   1620 aatttttgt gtctctcact cggaaggaca taagggcggc cgctagc   1667

<210> SEQ ID NO 3
<211> LENGTH: 2103
<212> TYPE: DNA
<213> ORGANISM: Artificial Sequence
<220> FEATURE:
<223> OTHER INFORMATION: Description of Artificial Sequence: NTC9685R
      vector backbone

<400> SEQUENCE: 3
ccgcctaatg agcgggcttt ttttggctt gttgtccaca accgttaaac cttaaaagct    60
ttaaaagcct tatatattct tttttttctt ataaaactta aaaccttaga ggctatttaa   120
gttgctgatt tatattaatt ttattgttca aacatgagag cttagtacgt gaaacatgag   180
agcttagtac gttagccatg agagcttagt acgttagcca tgagggttta gttcgttaaa   240
catgagagct tagtacgtta acatgagag cttagtacgt actatcaaca ggttgaactg   300
ctgatccacg ttgtggtaga attggtaaag agagtcgtgt aaaatatcga gttcgcacat   360
cttgttgtct gattattgat ttttggcgaa accatttgat catatgacaa gatgtgtatc   420
taccttaact taatgatttt gataaaaatc attaggtacc cctgatcact gtggaatgtg   480
tgtcagttag ggtgtggaaa gtccccaggc tccccagcag gcagaagtat gcaaagcatg   540
catctcaatt agtcagcaac caggtgtgga agtccccag gctccccagc aggcagaagt   600
atgcaaagca tgcatctcaa ttagtcagca accatagtcc cgcccctaac tccgcccatc   660
ccgcccctaa ctccgcccag ttacggggtc attagttcat agcccatata tggagttccg   720
cgttacataa cttacggtaa atggcccgcc tggctgaccg cccaacgacc cccgcccatt   780
gacgtcaata atgacgtatg ttcccatagt aacgccaata gggactttcc attgacgtca   840
atgggtggag tatttacggt aaactgccca cttggcagta catcaagtgt atcatatgcc   900
aagtacgccc cctattgacg tcaatgacgg taaatggccc gcctggcatt atgcccagta   960
catgacctta tgggactttc ctacttggca gtacatctac gtattagtca tcgctattac  1020
catggtgatg cggttttggc agtacatcaa tgggcgtgga tagcggtttg actcacgggg  1080
atttccaagt ctccacccca ttgacgtcaa tgggagtttg ttttggcacc aaaatcaacg  1140
ggactttcca aaatgtcgta caactccgcc ccattgacg caaatgggcg gtaggcgtgt  1200
acggtgggag gtctatataa gcagagctcg tttagtgaac cgtcagatcg cctggagacg  1260
ccatccacgc tgttttgacc tccatagaag acaccgggac cgatccagcc tccgcggctc  1320
gcatctctcc ttcacgcgcc cgccgcccta cctgaggccg ccatcacgc cggttgagtc  1380 gcgttctgcc gcctcccgcc tgtggtgcct cctgaactgc gtccgccgtc taggtaagtt  1440
```

-continued

```
taaagctcag gtcgagaccg ggcctttgtc cggcgctccc ttggagccta cctagactca   1500
gccggctctc cacgctttgc ctgaccctgc ttgctcaact ctagttctct cgttaactta   1560
atgagacaga tagaaactgg tcttgtagaa acagagtagt cgcctgcttt tctgccaggt   1620
gctgacttct ctcccctggg cttttttctt tttctcaggt tgaaagaag aagacgaaga    1680 agacgaagaa gacaaaccgt cgtcgacaga tctttttccc tctgccaaaa attatgggga   1740
catcatgaag cccccttgagc atctgacttc tggctaataa aggaaattta ttttcattgc  1800
aatagtgtgt tggaattttt tgtgtctctc actcggaagg acataagggc ggccgctagc   1860
ccgcctaatg agcgggcttt tttttcttag ggtgcaaaag gagagcctgt aagcgggcac   1920
tcttccgtgg tctggtggat aaattcgcaa gggtatcatg gcggacgacc ggggttcgag   1980
ccccgtatcc ggccgtccgc cgtgatccat gcggttaccg cccgcgtgtc gaacccaggt   2040
gtgcgacgtc agacaacggg ggagtgctcc ttttggcttc cttcccctac cggggccgct   2100
agc                                                                 2103

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: ColE2
      Origin (+7)

<400> SEQUENCE: 4
caaaagggcg ctgttatctg ataaggctta tctggtctca ttttg              45

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: ColE2
      Origin (+7, CpG free)

<400> SEQUENCE: 5
caaaaggggg ctgttatctg ataaggctta tctggtctca ttttg              45

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: ColE2
      Origin (Min)

<400> SEQUENCE: 6
ggcgctgtta tctgataagg cttatctggt ctcatttt                      38

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: ColE2
      Origin (+16)

<400> SEQUENCE: 7
ctgctcaaaa agacgccaaa agggcgctgt tatctgataa ggcttatctg gtctcatttt   60
g                                                                   61
```

<210> SEQ ID NO 8
<211> LENGTH: 1482
<212> TYPE: DNA
<213> ORGANISM: Artificial Sequence
<220> FEATURE:
<223> OTHER INFORMATION: Description of Artificial Sequence: NTC9385C vector backbone

<400> SEQUENCE: 8

```
tacaatggct catgtggaaa aaccattggc agaaaaacac ctgccaacag ttttaccaca      60
attgccactt aacccacaaa agggcgctgt tatctgataa ggcttatctg gtctcatttt     120
gcacgttgtg gtagaattgg taaagagagt cgtgtaaaat atcgagttcg cacatcttgt     180
tgtctgatta ttgattttg gcgaaaccat tgatcatat gacaagatgt gtatctacct      240
taacttaatg attttgataa aaatcattag gtaccccggc tctagttatt aatagtaatc     300
aattacgggg tcattagttc atagcccata tatggagttc cgcgttacat aacttacggt     360
aaatggcccg cctggctgac cgcccaacga ccccgccca ttgacgtcaa taatgacgta      420
tgttcccata gtaacgccaa tagggacttt ccattgacgt caatgggtgg agtatttacg     480
gtaaactgcc cacttggcag tacatcaagt gtatcatatg ccaagtacgc ccctattga      540
cgtcaatgac ggtaaatggc ccgcctggca ttatgcccag tacatgacct tatgggactt     600
tcctacttgg cagtacatct acgtattagt catcgctatt accatggtga tgcggttttg     660
gcagtacatc aatgggcgtg gatagcggtt tgactcacgg ggatttccaa gtctccaccc     720
cattgacgtc aatgggagtt tgttttggca ccaaaatcaa cgggactttc caaaatgtcg     780
taacaactcc gccccattga cgcaaatggg cggtaggcgt gtacggtggg aggtctatat     840
aagcagagct cgtttagtga accgtcagat cgcctggaga cgccatccac gctgttttga     900
cctccataga agacaccggg accgatccag cctccgcggc tcgcatctct ccttcacgcg     960
cccgccgccc tacctgaggc cgccatccac gccggttgag tcgcgttctg ccgcctcccg    1020
cctgtggtgc ctcctgaact cgtccgccg tctaggtaag tttaaagctc aggtcgagac     1080
cgggcctttg tccggcgctc ccttggagcc tacctagact cagccggctc tccacgcttt    1140
gcctgaccct gcttgctcaa ctctagttct ctcgttaact taatgagaca gatagaaact    1200
ggtcttgtag aaacagagta gtcgcctgct tttctgccag gtgctgactt ctctccctg     1260
ggctttttc tttttctcag gttgaaaaga agaagacgaa gaagacgaag aagacaaacc    1320
gtcgtcgaca gatctttttc cctctgccaa aaattatggg gacatcatga agccccttga    1380
gcatctgact tctggctaat aaaggaaatt tattttcatt gcaatagtgt gttggaattt    1440
tttgtgtctc tcactcggaa ggacataagg gcggccgcta gc                      1482
```

<210> SEQ ID NO 9
<211> LENGTH: 1918
<212> TYPE: DNA
<213> ORGANISM: Artificial Sequence
<220> FEATURE:
<223> OTHER INFORMATION: Description of Artificial Sequence: NTC9685C vector backbone

<400> SEQUENCE: 9

```
tacaatggct catgtggaaa aaccattggc agaaaaacac ctgccaacag ttttaccaca      60
attgccactt aacccacaaa agggcgctgt tatctgataa ggcttatctg gtctcatttt     120
gcacgttgtg gtagaattgg taaagagagt cgtgtaaaat atcgagttcg cacatcttgt     180
tgtctgatta ttgattttg gcgaaaccat tgatcatat gacaagatgt gtatctacct      240
```

```
taacttaatg attttgataa aaatcattag gtacccctga tcactgtgga atgtgtgtca    300
gttagggtgt ggaaagtccc caggctcccc agcaggcaga agtatgcaaa gcatgcatct    360
caattagtca gcaaccaggt gtggaaagtc cccaggctcc ccagcaggca gaagtatgca    420
aagcatgcat ctcaattagt cagcaaccat agtcccgccc ctaactccgc ccatcccgcc    480
cctaactccg cccagttacg gggtcattag ttcatagccc atatatggag ttccgcgtta    540
cataacttac ggtaaatggc ccgcctggct gaccgcccaa cgaccccgc ccattgacgt     600 caataatgac gtatgttccc atagtaacgc caatagggac tttccattga cgtcaatggg    660
tggagtattt acggtaaact gcccacttgg cagtacatca agtgtatcat atgccaagta    720
cgccccctat tgacgtcaat gacggtaaat ggcccgcctg gcattatgcc cagtacatga    780
ccttatggga ctttcctact ggcagtaca tctacgtatt agtcatcgct attaccatgg     840
tgatgcggtt ttggcagtac atcaatgggc gtggatagcg gtttgactca cggggatttc    900
caagtctcca ccccattgac gtcaatggga gtttgttttg gcaccaaaat caacgggact    960
ttccaaaatg tcgtaacaac tccgccccat tgacgcaaat gggcggtagg cgtgtacggt    1020
gggaggtcta tataagcaga gctcgtttag tgaaccgtca gatcgcctgg agacgccatc    1080
cacgctgttt tgacctccat agaagacacc gggaccgatc cagcctccgc ggctcgcatc    1140
tctccttcac gcgcccgccg ccctacctga ggccgccatc cacgccggtt gagtcgcgtt    1200
ctgccgcctc ccgcctgtgg tgcctcctga actgcgtccg ccgtctaggt aagtttaaag    1260
ctcaggtcga ccgggcct tgtccggcg ctcccttgga gcctacctag actcagccgg       1320
ctctccacgc tttgcctgac cctgcttgct caactctagt tctctcgtta acttaatgag    1380
acagatagaa actggtcttg tagaaacaga gtagtcgcct gcttttctgc caggtgctga    1440
cttctctccc ctgggctttt ttcttttct caggttgaaa agaagaagac gaagaagacg     1500
aagaagacaa accgtcgtcg acagatcttt ttccctctgc caaaaattat ggggacatca    1560
tgaagccccT tgagcatctg acttctggct aataaaggaa atttattttc attgcaatag    1620
tgtgttggaa ttttttgtgt ctctcactcg gaaggacata agggcggccg ctagcccgcc    1680
taatgagcgg gcttttttt cttagggtgc aaaaggagag cctgtaagcg ggcactcttc     1740
cgtggtctgg tggataaatt cgcaagggta tcatggcgga cgaccggggt tcgagccccg    1800
tatccggccg tccgccgtga tccatgcggt taccgcccgc gtgtcgaacc caggtgtgcg    1860
acgtcagaca acgggggagt gctccttttg gcttccttcc cctaccgggg ccgctagc      1918
```

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: PL Promoter
    (-35 to -10)

<400> SEQUENCE: 10
ttgacataaa taccactggc ggtgatact                                         29

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: PL Promoter
    OL1-G (-35 to
    -10)

<400> SEQUENCE: 11
ttgacataaa taccactggc gtgatact                                              28

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: PL Promoter
    OL1-G to T(-35 to
    -10)

<400> SEQUENCE: 12
ttgacataaa taccactggc gttgatact                                             29

<210> SEQ ID NO 13
<211> LENGTH: 305
<212> TYPE: PRT
<213> ORGANISM: Artificial Sequence
<220> FEATURE:
<223> OTHER INFORMATION: Description of Artificial Sequence: R6K Rep
    protein P42L-P113S

<400> SEQUENCE: 13

Met Arg Leu Lys Val Met Met Asp Val Asn Lys Lys Thr Lys Ile Arg
1               5                   10                  15

His Arg Asn Glu Leu Asn His Thr Leu Ala Gln Leu Pro Leu Pro Ala
            20                  25                  30

Lys Arg Val Met Tyr Met Ala Leu Ala Leu Ile Asp Ser Lys Glu Pro
        35                  40                  45

Leu Glu Arg Gly Arg Val Phe Lys Ile Arg Ala Glu Asp Leu Ala Ala
    50                  55                  60

Leu Ala Lys Ile Thr Pro Ser Leu Ala Tyr Arg Gln Leu Lys Glu Gly
65                  70                  75                  80

Gly Lys Leu Leu Gly Ala Ser Lys Ile Ser Leu Arg Gly Asp Asp Ile
                85                  90                  95

Ile Ala Leu Ala Lys Glu Leu Asn Leu Pro Phe Thr Ala Lys Asn Ser
            100                 105                 110

Ser Glu Glu Leu Asp Leu Asn Ile Ile Glu Trp Ile Ala Tyr Ser Asn
        115                 120                 125

Asp Glu Gly Tyr Leu Ser Leu Lys Phe Thr Arg Thr Ile Glu Pro Tyr
    130                 135                 140

Ile Ser Ser Leu Ile Gly Lys Lys Asn Lys Phe Thr Thr Gln Leu Leu
145                 150                 155                 160

Thr Ala Ser Leu Arg Leu Ser Ser Gln Tyr Ser Ser Ser Leu Tyr Gln
                165                 170                 175

Leu Ile Arg Lys His Tyr Ser Asn Phe Lys Lys Asn Tyr Phe Ile
            180                 185                 190

Ile Ser Val Asp Glu Leu Lys Glu Glu Leu Ile Ala Tyr Thr Phe Asp
        195                 200                 205

Lys Asp Gly Asn Ile Glu Tyr Lys Tyr Pro Asp Phe Pro Ile Phe Lys
    210                 215                 220

Arg Asp Val Leu Asn Lys Ala Ile Ala Glu Ile Lys Lys Lys Thr Glu
225                 230                 235                 240

Ile Ser Phe Val Gly Phe Thr Val His Glu Lys Glu Gly Arg Lys Ile
                245                 250                 255

Ser Lys Leu Lys Phe Glu Phe Val Val Asp Glu Asp Glu Phe Ser Gly

```
            260                 265                 270
Asp Lys Asp Asp Glu Ala Phe Phe Met Asn Leu Ser Glu Ala Asp Ala
        275                 280                 285

Ala Phe Leu Lys Val Phe Asp Glu Thr Val Pro Pro Lys Lys Ala Lys
        290                 295                 300

Gly
305

<210> SEQ ID NO 14
<211> LENGTH: 305
<212> TYPE: PRT
<213> ORGANISM: Artificial Sequence
<220> FEATURE:
<223> OTHER INFORMATION: Description of Artificial Sequence: R6K Rep
      protein P42L-P106L-F107S

<400> SEQUENCE: 14

Met Arg Leu Lys Val Met Met Asp Val Asn Lys Lys Thr Lys Ile Arg
1               5                   10                  15

His Arg Asn Glu Leu Asn His Thr Leu Ala Gln Leu Pro Leu Pro Ala
            20                  25                  30

Lys Arg Val Met Tyr Met Ala Leu Ala Leu Ile Asp Ser Lys Glu Pro
        35                  40                  45

Leu Glu Arg Gly Arg Val Phe Lys Ile Arg Ala Glu Asp Leu Ala Ala
    50                  55                  60

Leu Ala Lys Ile Thr Pro Ser Leu Ala Tyr Arg Gln Leu Lys Glu Gly
65                  70                  75                  80

Gly Lys Leu Leu Gly Ala Ser Lys Ile Ser Leu Arg Gly Asp Asp Ile
                85                  90                  95

Ile Ala Leu Ala Lys Glu Leu Asn Leu Leu Ser Thr Ala Lys Asn Ser
            100                 105                 110

Pro Glu Glu Leu Asp Leu Asn Ile Ile Glu Trp Ile Ala Tyr Ser Asn
        115                 120                 125

Asp Glu Gly Tyr Leu Ser Leu Lys Phe Thr Arg Thr Ile Glu Pro Tyr
    130                 135                 140

Ile Ser Ser Leu Ile Gly Lys Lys Asn Lys Phe Thr Thr Gln Leu Leu
145                 150                 155                 160

Thr Ala Ser Leu Arg Leu Ser Ser Gln Tyr Ser Ser Ser Leu Tyr Gln
                165                 170                 175

Leu Ile Arg Lys His Tyr Ser Asn Phe Lys Lys Asn Tyr Phe Ile
            180                 185                 190

Ile Ser Val Asp Glu Leu Lys Glu Glu Leu Ile Ala Tyr Thr Phe Asp
        195                 200                 205

Lys Asp Gly Asn Ile Glu Tyr Lys Tyr Pro Asp Phe Pro Ile Phe Lys
    210                 215                 220

Arg Asp Val Leu Asn Lys Ala Ile Ala Glu Ile Lys Lys Thr Glu
225                 230                 235                 240

Ile Ser Phe Val Gly Phe Thr Val His Glu Lys Glu Gly Arg Lys Ile
                245                 250                 255

Ser Lys Leu Lys Phe Glu Phe Val Val Asp Glu Asp Glu Phe Ser Gly
            260                 265                 270

Asp Lys Asp Asp Glu Ala Phe Phe Met Asn Leu Ser Glu Ala Asp Ala
        275                 280                 285

Ala Phe Leu Lys Val Phe Asp Glu Thr Val Pro Pro Lys Lys Ala Lys
    290                 295                 300
```

Gly
305

<210> SEQ ID NO 15
<211> LENGTH: 297
<212> TYPE: PRT
<213> ORGANISM: Artificial Sequence
<220> FEATURE:
<223> OTHER INFORMATION: Description of Artificial Sequence: ColE2 Rep
      protein (wild type)

<400> SEQUENCE: 15

Met Ser Ala Val Leu Gln Arg Phe Arg Glu Lys Leu Pro His Lys Pro
1               5                   10                  15

Tyr Cys Thr Asn Asp Phe Ala Tyr Gly Val Arg Ile Leu Pro Lys Asn
            20                  25                  30

Ile Ala Ile Leu Ala Arg Phe Ile Gln Gln Asn Gln Pro His Ala Leu
        35                  40                  45

Tyr Trp Leu Pro Phe Asp Val Asp Arg Thr Gly Ala Ser Ile Asp Trp
    50                  55                  60

Ser Asp Arg Asn Cys Pro Ala Pro Asn Ile Thr Val Lys Asn Pro Arg
65                  70                  75                  80

Asn Gly His Ala His Leu Leu Tyr Ala Leu Ala Leu Pro Val Arg Thr
                85                  90                  95

Ala Pro Asp Ala Ser Ala Ser Ala Leu Arg Tyr Ala Ala Ala Ile Glu
            100                 105                 110

Arg Ala Leu Cys Glu Lys Leu Gly Ala Asp Val Asn Tyr Ser Gly Leu
        115                 120                 125

Ile Cys Lys Asn Pro Cys His Pro Glu Trp Gln Glu Val Glu Trp Arg
    130                 135                 140

Glu Glu Pro Tyr Thr Leu Asp Glu Leu Ala Asp Tyr Leu Asp Leu Ser
145                 150                 155                 160

Ala Ser Ala Arg Arg Ser Val Asp Lys Asn Tyr Gly Leu Gly Arg Asn
                165                 170                 175

Tyr His Leu Phe Glu Lys Val Arg Lys Trp Ala Tyr Arg Ala Ile Arg
            180                 185                 190

Gln Gly Trp Pro Val Phe Ser Gln Trp Leu Asp Ala Val Ile Gln Arg
        195                 200                 205

Val Glu Met Tyr Asn Ala Ser Leu Pro Val Pro Leu Ser Pro Ala Glu
    210                 215                 220

Cys Arg Ala Ile Gly Lys Ser Ile Ala Lys Tyr Thr His Arg Lys Phe
225                 230                 235                 240

Ser Pro Glu Gly Phe Ser Ala Val Gln Ala Ala Arg Gly Arg Lys Gly
                245                 250                 255

Gly Thr Lys Ser Lys Arg Ala Ala Val Pro Thr Ser Ala Arg Ser Leu
            260                 265                 270

Lys Pro Trp Glu Ala Leu Gly Ile Ser Arg Ala Thr Tyr Tyr Arg Lys
        275                 280                 285

Leu Lys Cys Asp Pro Asp Leu Ala Lys
    290                 295

<210> SEQ ID NO 16
<211> LENGTH: 297
<212> TYPE: PRT
<213> ORGANISM: Artificial Sequence
<220> FEATURE:
<223> OTHER INFORMATION: Description of Artificial Sequence: ColE2 Rep
      protein mut (G194D)

<400> SEQUENCE: 16

Met Ser Ala Val Leu Gln Arg Phe Arg Glu Lys Leu Pro His Lys Pro
1               5                   10                  15

Tyr Cys Thr Asn Asp Phe Ala Tyr Gly Val Arg Ile Leu Pro Lys Asn
            20                  25                  30

Ile Ala Ile Leu Ala Arg Phe Ile Gln Gln Asn Gln Pro His Ala Leu
        35                  40                  45

Tyr Trp Leu Pro Phe Asp Val Asp Arg Thr Gly Ala Ser Ile Asp Trp
    50                  55                  60

Ser Asp Arg Asn Cys Pro Ala Pro Asn Ile Thr Val Lys Asn Pro Arg
65              70                  75                  80

Asn Gly His Ala His Leu Leu Tyr Ala Leu Ala Leu Pro Val Arg Thr
                85                  90                  95

Ala Pro Asp Ala Ser Ala Ser Ala Leu Arg Tyr Ala Ala Ala Ile Glu
            100                 105                 110

Arg Ala Leu Cys Glu Lys Leu Gly Ala Asp Val Asn Tyr Ser Gly Leu
        115                 120                 125

Ile Cys Lys Asn Pro Cys His Pro Glu Trp Gln Glu Val Glu Trp Arg
    130                 135                 140

Glu Glu Pro Tyr Thr Leu Asp Glu Leu Ala Asp Tyr Leu Asp Leu Ser
145                 150                 155                 160

Ala Ser Ala Arg Arg Ser Val Asp Lys Asn Tyr Gly Leu Gly Arg Asn
                165                 170                 175

Tyr His Leu Phe Glu Lys Val Arg Lys Trp Ala Tyr Arg Ala Ile Arg
            180                 185                 190

Gln Asp Trp Pro Val Phe Ser Gln Trp Leu Asp Ala Val Ile Gln Arg
        195                 200                 205

Val Glu Met Tyr Asn Ala Ser Leu Pro Val Pro Leu Ser Pro Ala Glu
    210                 215                 220

Cys Arg Ala Ile Gly Lys Ser Ile Ala Lys Tyr Thr His Arg Lys Phe
225                 230                 235                 240

Ser Pro Glu Gly Phe Ser Ala Val Gln Ala Ala Arg Gly Arg Lys Gly
                245                 250                 255

Gly Thr Lys Ser Lys Arg Ala Ala Val Pro Thr Ser Ala Arg Ser Leu
            260                 265                 270

Lys Pro Trp Glu Ala Leu Gly Ile Ser Arg Ala Thr Tyr Tyr Arg Lys
        275                 280                 285

Leu Lys Cys Asp Pro Asp Leu Ala Lys
    290                 295

<210> SEQ ID NO 17
<211> LENGTH: 4706
<212> TYPE: DNA
<213> ORGANISM: Artificial Sequence
<220> FEATURE:
<223> OTHER INFORMATION: Description of Artificial Sequence: pINT pR pL
      R6K Rep piP42L-P106L-F107S (P3-)

<400> SEQUENCE: 17
ctgcaggtga tgattatcag ccagcagaga ttaaggaaaa cagacaggtt tattgagcgc    60
ttatctttcc ctttattttt gctgcggtaa gtcgcataaa accattcttc ataattcaa    120 tccatttact atgttatgtt ctgaggggag tgaaaattcc cctaattcga tgaagattct    180
tgctcaattg ttatcagcta tgcgccgacc agaacacctt gccgatcagc caaacgtctc    240

-continued

```
ttcaggccac tgactagcga taactttccc cacaacggaa caactctcat tgcatgggat      300
cattgggtac tgtgggttta gtggttgtaa aaacacctga ccgctatccc tgatcagttt      360
cttgaaggta aactcatcac ccccaagtct ggctatgcag aaatcacctg gctcaacagc      420
ctgctcaggg tcaacgagaa ttaacattcc gtcaggaaag cttggcttgg agcctgttgg      480
tgcggtcatg gaattacctt caacctcaag ccagaatgca gaatcactgg cttttttggt      540
tgtgcttacc catctctccg catcaccttt ggtaaaggtt ctaagcttag gtgagaacat      600
ccctgcctga acatgagaaa aaacagggta ctcatactca cttctaagtg acggctgcat      660
actaaccgct tcatacatct cgtagatttc tctggcgatt gaagggctaa attcttcaac      720
gctaactttg agaattttttg taagcaatgc ggcgttataa gcatttaatg cattgatgcc      780
attaaataaa gcaccaacgc ctgactgccc catccccatc ttgtctgcga cagattcctg      840
ggataagcca agttcatttt tcttttttttc ataaattgct ttaaggcgac gtgcgtcctc      900
aagctgctct tgtgttaatg gtttcttttt tgtgctcata cgttaaatct atcaccgcaa      960
gggataaata tctaacaccg tgcgtgttga ctatttttacc tctggcggtg ataatggttg     1020
catgtactaa ggaggttgta tggaacaacg cataaccctg aaagattatg caatgcgctt     1080
tgggcaaacc aagacagcta agatctctc acctaccaaa caatgccccc ctgcaaaaaa      1140
taaattcata taaaaaacat acagataacc atctgcggtg ataaattatc tctggcggtg     1200
ttgacataaa taccactggc ggtgatactg agcacatcag caggacgcac tgaccaccat     1260
gaaggtgacg ctcttaaaaa ttaagccctg aagaagggca gcattcaaag cagaaggctt     1320
tggggtgtgt gatacgaaac gaagcattgg gatccagaag gagatataca tatgagactc     1380
aaggtcatga tggacgtgaa caaaaaaacg aaaattcgcc accgaaacga gctaaatcac     1440
accctggctc aacttccttt gcccgcaaag cgagtgatgt atatggcgct tgctctcatt     1500
gatagcaaag aacctcttga acgagggcga gttttcaaaa ttagggctga agaccttgca     1560
gcgctcgcca aaatcacccc atcgcttgct tatcgacaat taaaagaggg tggtaaatta     1620
cttggtgcca gcaaaatttc gctaagaggg gatgatatca ttgctttagc taagagctt      1680 aacctgctgt ctactgctaa aaactcccct gaagagttag atcttaacat tattgagtgg     1740
atagcttatt caaatgatga aggatacttg tctttaaaat tcaccagaac catagaacca     1800
tatatctcta gccttattgg gaaaaaaaat aaattcacaa cgcaattgtt aacggcaagc     1860
ttacgcttaa gtagccagta ttcatcttct ctttatcaac ttatcaggaa gcattactct     1920
aattttaaga agaaaaatta ttttattatt tccgttgatg agttaaagga gagttaata      1980 gcttatactt ttgataaaga tggaaatatt gagtacaaat accctgactt tcctattttt     2040
aaaagggatg tgttaaataa agccattgct gaaattaaaa agaaaacaga atatcgttt      2100 gttggcttca ctgttcatga aaaagaaggg agaaaaatta gtaagctgaa gttcgaattt     2160
gtcgttgatg aagatgaatt ttctggcgat aaagatgatg aagcttttttt tatgaattta     2220 tctgaagctg atgcagcttt tctcaaggta tttgatgaaa ccgtacctcc caaaaaagct     2280 aagggggtgag aattctcatg tttgacagct tatcactgat cagtgaatta atggcgatga     2340
cgcatcctca cgataatatc cgggtaggcg caatcacttt cgtctctact ccgttacaaa     2400
gcgaggctgg gtatttcccg gcctttctgt tatccgaaat ccactgaaag cacagcggct     2460
ggctgaggag ataaataata aacgaggggc tgtatgcaca aagcatcttc tgttgagtta     2520
agaacgagta tcgagatggc acatagcctt gctcaaattg gaatcaggtt tgtgccaata     2580
ccagtagaaa cagacgaaga agctagctaa tgctctgtct caggtcacta atactatcta     2640
```

```
agtagttgat tcatagtgac tggatatgtt gcgttttgtc gcattatgta gtctatcatt    2700
taaccacaga ttagtgtaat gcgatgattt ttaagtgatt aatgttattt tgtcatcctt    2760
taggtgaata agttgtatat ttaaaatctc tttaattatc agtaaattaa tgtaagtagg    2820
tcattattag tcaaaataaa atcatttgtc gatttcaatt ttgtcccatg ctaattccc     2880
atgtcagccg ttaagtgttc ctgtgtcact caaaattgct tgagaggct ctaagggctt     2940
ctcagtgcgt tacatccctg gcttgttgtc cacaaccgtt aaaccttaaa agctttaaaa    3000
gccttatata ttcttttttt tcttataaaa cttaaaacct tagaggctat ttaagttgct    3060
gatttatatt aattttattg ttcaaacatg agagcttagt acgtgaaaca tgagagctta    3120
gtacgttagc catgagagct tagtacgtta gccatgaggg tttagttcgt taaacatgag    3180
agcttagtac gttaaacatg agagcttagt acgtgaaaca tgagagctta gtacgtacta    3240
tcaacaggtt gaactgctga tcttcagatc ctctacgccg gacgcatcgt ggccggatct    3300
tgcggccgct cggcttgaac gaattgttag acattatttg ccgactacct tggtgatctc    3360
gcctttcacg tagtggacaa attcttccaa ctgatctgcg cgcgaggcca agcgatcttc    3420
ttcttgtcca agataagcct gtctagcttc aagtatgacg ggctgatact gggccggcag    3480
gcgctccatt gcccagtcgg cagcgacatc cttcggcgcg attttgccgg ttactgcgct    3540
gtaccaaatg cgggacaacg taagcactac atttcgctca tcgccagccc agtcgggcgg    3600
cgagttccat agcgttaagg tttcatttag cgcctcaaat agatcctgtt caggaaccgg    3660
atcaaagagt tcctccgccg ctggacctac caaggcaacg ctatgttctc ttgcttttgt    3720
cagcaagata gccagatcaa tgtcgatcgt ggctggctcg aagatacctg caagaatgtc    3780
attgcgctgc cattctccaa attgcagttc gcgcttagct ggataacgcc acggaatgat    3840
gtcgtcgtgc acaacaatgg tgacttctac agcgcggaga atctcgctct ctccagggga    3900
agccgaagtt tccaaaaggt cgttgatcaa agctcgccgc gttgtttcat caagccttac    3960
ggtcaccgta accagcaaat caatatcact gtgtggcttc aggccgccat ccactgcgga    4020
gccgtacaaa tgtacggcca gcaacgtcgg ttcgagatgg cgctcgatga cgccaactac    4080
ctctgatagt tgagtcgata cttcggcgat caccgcttcc ctcatgatgt ttaactttgt    4140
tttagggcga ctgccctgct gcgtaacatc gttgctgctc cataacatca aacatcgacc    4200
cacggcgtaa cgcgcttgct gcttggatgc ccgaggcata gactgtaccc caaaaaaaca    4260
gtcataacaa gccatgaaaa ccgccactgc gccgttacca ccgctgcgtt cggtcaaggt    4320
tctgaccag ttgcgtgagc gcatacgcta cttgcattac agcttacgaa ccgaacaggc     4380
ttatgtccac tgggttcgtg ccttcatccg tatcgatggc ccccgatggt agtgtggggt    4440
ctccccatgc gagagtaggg aactgccagg catcaaataa aacgaaaggc tcagtcgaaa    4500
gactgggcct ttcgttttat ctgttgtttg tcggtgaacg ctctcctgag taggacaaat    4560
ccgccgggag cggatttgaa cgttgcgaag caacggcccg gagggtggcg gcaggacgc     4620
ccgccataaa ctgccaggca tcaaattaag cagaaggcca tcctgacgga tggcctttt     4680
gcgtggccag tgccaagctt gcatgc                                         4706
```

<210> SEQ ID NO 18
<211> LENGTH: 4685
<212> TYPE: DNA
<213> ORGANISM: Artificial Sequence
<220> FEATURE:
<223> OTHER INFORMATION: Description of Artificial Sequence: pINT pR pL ColE2 Rep protein mut (G194D)

<400> SEQUENCE: 18

```
ctgcaggtga tgattatcag ccagcagaga ttaaggaaaa cagacaggtt tattgagcgc      60
ttatctttcc ctttattttt gctgcggtaa gtcgcataaa aaccattctt cataattcaa     120
tccatttact atgttatgtt ctgaggggag tgaaaattcc cctaattcga tgaagattct     180
tgctcaattg ttatcagcta tgcgccgacc agaacacctt gccgatcagc caaacgtctc     240
ttcaggccac tgactagcga taactttccc cacaacggaa caactctcat tgcatgggat     300
cattgggtac tgtgggttta gtggttgtaa aaacacctga ccgctatccc tgatcagttt     360
cttgaaggta aactcatcac ccccaagtct ggctatgcag aaatcacctg gctcaacagc     420
ctgctcaggg tcaacgagaa ttaacattcc gtcaggaaag cttggcttgg agcctgttgg     480
tgcggtcatg gaattacctt caacctcaag ccagaatgca gaatcactgg cttttttggt     540
tgtgcttacc catctctccg catcaccttt ggtaaaggtt ctaagcttag gtgagaacat     600
ccctgcctga acatgagaaa aaacagggta ctcatactca cttctaagtg acggctgcat     660
actaaccgct tcatacatct cgtagatttc tctggcgatt gaagggctaa attcttcaac     720
gctaactttg agaattttg taagcaatgc ggcgttataa gcatttaatg cattgatgcc     780
attaaataaa gcaccaacgc ctgactgccc catccccatc ttgtctgcga cagattcctg     840
ggataagcca agttcatttt tcttttttc ataaattgct ttaaggcgac gtgcgtcctc     900
aagctgctct tgtgttaatg gtttctttt tgtgctcata cgttaaatct atcaccgcaa     960
gggataaaata tctaacaccg tgcgtgttga ctattttacc tctggcgtg ataatggttg    1020
catgtactaa ggaggttgta tggaacaacg cataaccctg aaagattatg caatgcgctt    1080
tgggcaaacc aagacagcta agatctctc acctaccaaa caatgccccc ctgcaaaaaa    1140
taaattcata taaaaaacat acagataacc atctgcggtg ataaattatc tctggcggtg    1200
ttgacataaa taccactggc ggtgatactg agcacatcag caggacgcac tgaccaccat    1260
gaaggtgacg ctcttaaaaa ttaagccctg aagaagggca gcattcaaag cagaaggctt    1320
tggggtgtgt gatacgaaac gaagcattgg gatccagaag gagatataca tatgagtgcc    1380
gtacttcagc gcttcaggga aaaattaccg cacaaaccgt actgtacgaa cgatttcgcg    1440
tacgcgttc gcattctgcc gaaaaacatt gccattcttg cccgtttcat ccagcagaac    1500
cagccacatg cactgtactg gcttcccttt gacgtggacc ggacggggc atcaatcgac    1560
tggagcgacc ggaattgtcc ggccccgaac atcaccgtaa aaaatccccg taacgggcac    1620
gcgcatctgc tctacgcgct cgcccttcct gtgagaactg cgccggatgc atcggcttcg    1680
gcgctcagat acgctgccgc tattgagcgt gcgttgtgtg aaaaactggg cgcggatgtg    1740
aattacagcg gcctgatctg caaaaatccg tgccaccctg aatggcagga agtggaatgg    1800
cgcgaggaac cctacactct cgacgaactg gctgattatc tcgatttgag cgcctcagcg    1860
cgccgtagcg tcgataaaaa ttacgggctg ggcgaaact accatctgtt cgaaaaggtc    1920
cgtaaatggg cctacagagc gattcgtcag gactggcctg tattctcaca atggcttgat    1980
gccgtgatcc agcgtgtcga aatgtacaac gcatcgcttc ccgttccgct ttctccggct    2040
gaatgtcggg ctattggcaa gagcattgcg aaatatacac acaggaaatt ctcaccgagg    2100
ggatttccg ctgtacaggc cgctcgaggt cgcaagggcg aactaaatc taagcgcgca    2160
gcagttccta catcagcacg ttcgctgaag ccgtgggagg cattagggat cagtcgagcg    2220
acgtactacc gaaaattaaa atgtgatcca gatctcgcaa aatgataaga attctcatgt    2280
```

```
ttgacagctt atcactgatc agtgaattaa tggcgatgac gcatcctcac gataatatcc    2340
gggtaggcgc aatcactttc gtctctactc cgttacaaag cgaggctggg tatttcccgg    2400
cctttctgtt atccgaaatc cactgaaagc acagcggctg gctgaggaga taaataataa    2460
acgaggggct gtatgcacaa agcatcttct gttgagttaa gaacgagtat cgagatggca    2520
catagccttg ctcaaattgg aatcaggttt gtgccaatac cagtagaaac agacgaagaa    2580
gctagctaat gctctgtctc aggtcactaa tactatctaa gtagttgatt catagtgact    2640
ggatatgttg cgttttgtcg cattatgtag tctatcattt aaccacagat tagtgtaatg    2700
cgatgatttt taagtgatta atgttatttt gtcatccttt aggtgaataa gttgtatatt    2760
taaaatctct ttaattatca gtaaattaat gtaagtaggt cattattagt caaaataaaa    2820
tcatttgtcg atttcaattt tgtcccatgg ctaattccca tgtcagccgt taagtgttcc    2880
tgtgtcactc aaaattgctt tgagaggctc taagggcttc tcagtgcgtt acatccctgg    2940
cttgttgtcc acaaccgtta aaccttaaaa gctttaaaag ccttatatat tcttttttt    3000 cttataaaac ttaaaacctt agaggctatt taagttgctg atttatatta attttattgt    3060
tcaaacatga gagcttagta cgtgaaacat gagagcttag tacgttagcc atgagagctt    3120
agtacgttag ccatgagggt ttagttcgtt aaacatgaga gcttagtacg ttaaacatga    3180
gagcttagta cgtgaaacat gagagcttag tacgtactat caacaggttg aactgctgat    3240
cttcagatcc tctacgccgg acgcatcgtg gccggatctt gcggccgctc ggcttgaacg    3300
aattgttaga cattatttgc cgactacctt ggtgatctcg cctttcacgt agtggacaaa    3360
ttcttccaac tgatctgcgc gcgaggccaa gcgatcttct tcttgtccaa gataagcctg    3420
tctagcttca gtatgacgg gctgatactg ggccggcagg cgctccattg cccagtcggc    3480
agcgacatcc ttcggcgcga ttttgccggt tactgcgctg taccaaatgc gggacaacgt    3540
aagcactaca tttcgctcat cgccagccca gtcgggcggc gagttccata gcgttaaggt    3600
ttcatttagc gcctcaaata gatcctgttc aggaaccgga tcaaagagtt cctccgccgc    3660
tggacctacc aaggcaacgc tatgttctct tgcttttgtc agcaagatag ccagatcaat    3720
gtcgatcgtg gctggctcga agatacctgc aagaatgtca ttgcgctgcc attctccaaa    3780
ttgcagttcg cgcttagctg gataacgcca cggaatgatg tcgtcgtgca acaatggtt   3840 gacttctaca gcgcggagaa tctcgctctc tccaggggaa gccgaagttt ccaaaaggtc    3900
gttgatcaaa gctcgccgcg ttgtttcatc aagccttacg gtcaccgtaa ccagcaaatc    3960
aatatcactg tgtggcttca ggccgccatc cactgcggag ccgtacaaat gtacggccag    4020
caacgtcggt tcgagatggc gctcgatgac gccaactacc tctgatagtt gagtcgatac    4080
ttcggcgatc accgcttccc tcatgatgtt taactttgtt ttagggcgac tgccctgctg    4140
cgtaacatcg ttgctgctcc ataacatcaa acatcgaccc acggcgtaac gcgcttgctg    4200
cttggatgcc cgaggcatag actgtacccc aaaaaaacag tcataacaag ccatgaaaac    4260
cgccactgcg ccgttaccac cgctgcgttc ggtcaaggtt ctggaccagt tgcgtgagcg    4320
catacgctac ttgcattaca gcttacgaac cgaacaggct tatgtccact gggttcgtgc    4380
cttcatccgt atcgatggcc cccgatggta gtgtggggtc tccccatgcg agagtaggga    4440
actgccaggc atcaaataaa acgaaaggct cagtcgaaag actgggcctt tcgttttatc    4500
tgttgtttgt cggtgaacgc tctcctgagt aggacaaatc cgccgggagc ggatttgaac    4560
gttgcgaagc aacggcccgg agggtggcgg gcaggacgcc cgccataaac tgccaggcat    4620
caaattaagc agaaggccat cctgacggat ggcctttttg cgtggccagt gccaagcttg    4680
``` catgc                                                             4685

<210> SEQ ID NO 19
<211> LENGTH: 466
<212> TYPE: DNA
<213> ORGANISM: Artificial Sequence
<220> FEATURE:
<223> OTHER INFORMATION: Description of Artificial Sequence: NTC9385R
      and NTC9685R Bacterial region [NheI site-trpA terminator-R6K
      Origin-RNA-OUT-KpnI site]

<400> SEQUENCE: 19
gctagcccgc ctaatgagcg ggcttttttt tggcttgttg tccacaaccg ttaaaccttaa     60 aaagctttaa aagccttata tattctttt tttcttataa aacttaaaac cttagaggct     120
atttaagttg ctgatttata ttaatttat tgttcaaaca tgagagctta gtacgtgaaa     180
catgagagct tagtacgtta gccatgagag cttagtacgt tagccatgag ggtttagttc     240
gttaaacatg agagcttagt acgttaaaca tgagagctta gtacgtacta tcaacaggtt     300
gaactgctga tccacgttgt ggtagaattg gtaaagagag tcgtgtaaaa tatcgagttc     360
gcacatcttg ttgtctgatt attgattttt ggcgaaacca tttgatcata tgacaagatg     420
tgtatctacc ttaacttaat gattttgata aaatcatta ggtacc                    466

<210> SEQ ID NO 20
<211> LENGTH: 281
<212> TYPE: DNA
<213> ORGANISM: Artificial Sequence
<220> FEATURE:
<223> OTHER INFORMATION: Description of Artificial Sequence: NTC9385C
      and NTC9685C Bacterial region [NheI site-ssiA-ColE2 Origin
      (+7)-RNA-OUT-KpnI site]

<400> SEQUENCE: 20
gctagctaca atggctcatg tggaaaaacc attggcagaa aaacacctgc caacagtttt      60
accacaattg ccacttaacc cacaaaaggg cgctgttatc tgataaggct tatctggtct     120
cattttgcac gttgtggtag aattggtaaa gagagtcgtg taaatatcg agttcgcaca     180 tcttgttgtc tgattattga ttttggcga aaccatttga tcatatgaca agatgtgtat     240
ctaccttaac ttaatgattt tgataaaaat cattaggtac c                        281

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: NTC9385C
      and NTC9685C CpG free ssiA [from plasmid R6K]

<400> SEQUENCE: 21
tacaatggct catgtggaaa aaccattggc agaaaaacac ctgccaacag ttttaccaca      60
attgccactt aaccca                                                     76

<210> SEQ ID NO 22
<211> LENGTH: 260
<212> TYPE: DNA
<213> ORGANISM: Artificial Sequence
<220> FEATURE:
<223> OTHER INFORMATION: Description of Artificial Sequence: CpG free
      R6K origin

<400> SEQUENCE: 22

```
aaaccttaaa acctttaaaa gccttatata ttctttttt tcttataaaa cttaaaacct     60
tagaggctat ttaagttgct gatttatatt aattttattg ttcaaacatg agagcttagt   120
acatgaaaca tgagagctta gtacattagc catgagagct tagtacatta gccatgaggg   180
tttagttcat taaacatgag agcttagtac attaaacatg agagcttagt acatactatc   240
aacaggttga actgctgatc                                               260
```

```
<210> SEQ ID NO 23
<211> LENGTH: 137
<212> TYPE: DNA
<213> ORGANISM: Artificial Sequence
<220> FEATURE:
<223> OTHER INFORMATION: Description of Artificial Sequence: RNA-OUT
      Selectable Marker from NTC9385C, NTC9685C, NTC9385R, NTC9685R

<400> SEQUENCE: 23
```

```
agaattggta aagagagtcg tgtaaaatat cgagttcgca catcttgttg tctgattatt    60
gatttttggc gaaaccattt gatcatatga caagatgtgt atctaccttta acttaatgat  120 tttgataaaa atcatta                                                  137
```

```
<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: RNA-OUT
      Sense strand RNA from NTC9385C, NTC9685C, NTC9385R, NTC9685R,
      NTC9385Ra

<400> SEQUENCE: 24
```

```
ttcgcacatc ttgttgtctg attattgatt tttggcgaaa ccatttgatc atatgacaag    60
atgtgtatct                                                           70
```

```
<210> SEQ ID NO 25
<211> LENGTH: 87
<212> TYPE: DNA
<213> ORGANISM: Artificial Sequence
<220> FEATURE:
<223> OTHER INFORMATION: Description of Artificial Sequence: TPA
      secretion sequence

<400> SEQUENCE: 25
```

```
atggatgcaa tgaagagagg gctctgctgt gtgctgctgc tgtgtggagc agtcttcgtt    60
tcgcccagcg gtaccggatc cgtcgac                                        87
```

```
<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: PCR primer
      15061101

<400> SEQUENCE: 26
```

```
ggaacgggat ccagaaggag atatacatat gagtgccgta cttcagcgct tcaggga       57
```

```
<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: PCR primer
      15061102
```

-continued

<400> SEQUENCE: 27
ggaacggaat tcttatcatt ttgcgagatc tggatcacat                                40

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: ColE2 core
      replication origin

<400> SEQUENCE: 28
ggcgctgtta tctgataagg cttatctggt ct                                       32

<210> SEQ ID NO 29
<211> LENGTH: 121
<212> TYPE: DNA
<213> ORGANISM: Artificial Sequence
<220> FEATURE:
<223> OTHER INFORMATION: Description of Artificial Sequence: +7(CpG
      free)-ssiA ColE2 origin

<400> SEQUENCE: 29
tacaatggct catgtggaaa aaccattggc agaaaaacac ctgccaacag ttttaccaca         60
attgccactt aacccacaaa aggggctgt tatctgataa ggcttatctg gtctcatttt         120
g                                                                       121

<210> SEQ ID NO 30
<211> LENGTH: 228
<212> TYPE: DNA
<213> ORGANISM: Artificial Sequence
<220> FEATURE:
<223> OTHER INFORMATION: Description of Artificial Sequence: HTLV-
      IR-Rabbit Beta globin hybrid intron

<400> SEQUENCE: 30
aggtaagttt aaagctcagg tcgagaccgg gcctttgtcc ggcgctccct tggagcctac         60
ctagactcag ccggctctcc acgctttgcc tgaccctgct tgctcaactc tagttctctc        120
gttaacttaa tgagacagat agaaactggt cttgtagaaa cagagtagtc gcctgctttt        180
ctgccaggtg ctgacttctc tcccctgggc ttttttcttt ttctcagg                     228

<210> SEQ ID NO 31
<211> LENGTH: 108
<212> TYPE: DNA
<213> ORGANISM: Artificial Sequence
<220> FEATURE:
<223> OTHER INFORMATION: Description of Artificial Sequence: pMB1 RNAI
      antisense repressor RNA (origin antisense partner of RNAII)

<400> SEQUENCE: 31
acagtatttg gtatctgcgc tctgctgaag ccagttacct tcggaaaaag agttggtagc         60
tcttgatccg gcaaacaaac caccgctggt agcggtggtt ttttttgtt                    108

<210> SEQ ID NO 32
<211> LENGTH: 156
<212> TYPE: DNA
<213> ORGANISM: Artificial Sequence
<220> FEATURE:
<223> OTHER INFORMATION: Description of Artificial Sequence: pMB1 RNAI
      selectable Marker, RNAI RNA (Sense strand)

<400> SEQUENCE: 32

```
ttgaagtggt ggcctaacta cggctacact agaagaacag tatttggtat ctgcgctctg    60
ctgaagccag ttaccttcgg aaaaagagtt ggtagctctt gatccggcaa acaaaccacc   120
gctggtagcg gtggtttttt tgtttgcaag cagcag                             156
```

<210> SEQ ID NO 33
<211> LENGTH: 73
<212> TYPE: DNA
<213> ORGANISM: Artificial Sequence
<220> FEATURE:
<223> OTHER INFORMATION: Description of Artificial Sequence: IncB RNAI
      antisense repressor RNA (IncB plasmid origin RNAII antisense
      partner)

<400> SEQUENCE: 33

```
gtattctgtg aggcccccat tatttttctg cgttccgcca agttcgagga aaaatagtgg    60
gggttttcct tta                                                       73
```

<210> SEQ ID NO 34
<211> LENGTH: 124
<212> TYPE: DNA
<213> ORGANISM: Artificial Sequence
<220> FEATURE:
<223> OTHER INFORMATION: Description of Artificial Sequence: IncB RNAI
      selectable Marker. DraIII-KpnI restriction fragment.

<400> SEQUENCE: 34

```
cacgttgtgt tgaatctctg gtacggtttc atatatactt atcccgtatt ctgtgaggcc    60
cccattattt ttctgcgttc cgccaagttc gaggaaaaat agtgggggtt ttcctttagg   120
tacc                                                                124
```

<210> SEQ ID NO 35
<211> LENGTH: 362
<212> TYPE: DNA
<213> ORGANISM: Artificial Sequence
<220> FEATURE:
<223> OTHER INFORMATION: Description of Artificial Sequence: IncB
      RNAII-SacB. PstI-MamI restriction fragment

<400> SEQUENCE: 35

```
ctgcagttca aagcggtgga aaaggggtat attgcggatc gttattcagt ggcttttggg    60
atcctcgcgg tccggaaagc cagaaaacgg cagaatgcgc cataaggcat tcaggacgta   120
tggcagaaac gacggcagtt tgccggtgcc ggaaggctga aaaaagtttc agaagaccat   180
aaaggaaaac ccccactatt tttcctcgaa cttggcggaa cgcagaaaaa taatgggggc   240
ctcacagaat acgggatagg gcccatgaaa ccgtaccaga gattgggccc tgtgcagtgt   300
ataaatacac ggcacaatcg ctccgccata agcgacagct tgtggcaggt ctgatgaaca   360
tc                                                                  362
```

<210> SEQ ID NO 36
<211> LENGTH: 159
<212> TYPE: DNA
<213> ORGANISM: Artificial Sequence
<220> FEATURE:
<223> OTHER INFORMATION: Description of Artificial Sequence: CpG free
      RNA-OUT selection marker - flanked by KpnI and BglII- EcoRI sites

<400> SEQUENCE: 36

```
ggtacctggt agaattggta agagagttg tgtaaaatat tgagttagca catcttgttg    60
tctgattatt gatttttggg gaaaccattt gatcatatga caagatgtgt atctacctta   120
```

```
acttaatgat tttgataaaa atcattaaga tctgaattc                          159
```

<210> SEQ ID NO 37
<211> LENGTH: 432
<212> TYPE: DNA
<213> ORGANISM: Artificial Sequence
<220> FEATURE:
<223> OTHER INFORMATION: Description of Artificial Sequence: CpG free
      R6K gamma - RNA-OUT bacterial region (CpG free R6K origin-CpG free
      RNA-OUT selection marker)-flanked by EcoRI-SphI and BglII-EcoRI
      sites

<400> SEQUENCE: 37

```
gaattcagca tgcaaacctt aaaaccttta aaagccttat atattctttt ttttcttata    60
aaacttaaaa ccttagaggc tatttaagtt gctgatttat attaatttta ttgttcaaac   120
atgagagctt agtacatgaa acatgagagc ttagtacatt agccatgaga gcttagtaca   180
ttagccatga gggtttagtt cattaaacat gagagcttag tacattaaac atgagagctt   240
agtacatact atcaacaggt tgaactgctg atcggtacct ggtagaattg gtaaagagag   300
ttgtgtaaaa tattgagtta gcacatcttg ttgtctgatt attgattttt ggggaaacca   360
tttgatcata tgacaagatg tgtatctacc ttaacttaat gattttgata aaatcatta    420 agatctgaat tc                                                       432
```

<210> SEQ ID NO 38
<211> LENGTH: 292
<212> TYPE: DNA
<213> ORGANISM: Artificial Sequence
<220> FEATURE:
<223> OTHER INFORMATION: Description of Artificial Sequence: CpG free
      ColE2 bacterial region (CpG free ssiA-CpG free ColE2 origin-CpG
      free RNA-OUT selection marker)- - flanked by EcoRI-SphI and
      BglII-EcoRI sites

<400> SEQUENCE: 38

```
gaattcagca tgctacaatg gctcatgtgg aaaaaccatt ggcagaaaaa cacctgccaa    60
cagttttacc acaattgcca cttaacccac aaaaggggc tgttatctga taaggcttat    120
ctggtctcat tttggtacct ggtagaattg gtaaagagag ttgtgtaaaa tattgagtta   180
gcacatcttg ttgtctgatt attgattttt ggggaaacca tttgatcata tgacaagatg   240
tgtatctacc ttaacttaat gattttgata aaatcatta agatctgaat tc            292
```

<210> SEQ ID NO 39
<211> LENGTH: 1660
<212> TYPE: DNA
<213> ORGANISM: Artificial Sequence
<220> FEATURE:
<223> OTHER INFORMATION: Description of Artificial Sequence:
      NTC9385Ra-O2 vector backbone

<400> SEQUENCE: 39

```
ccgcctaatg agcgggcttt ttttggctt gttgtccaca accgttaaac cttaaaagct     60
ttaaaagcct tatatattct tttttttctt ataaaactta aaaccttaga ggctatttaa   120
gttgctgatt tatattaatt ttattgttca acatgagag cttagtacgt gaaacatgag    180
agcttagtac gttagccatg agagcttagt acgttagcca tgagggttta gttcgttaaa   240
catgagagct tagtacgtta acatgagag cttagtacgt actatcaaca ggttgaactg    300
ctgatccacc ccggctctag ttattaatag taatcaatta cggggtcatt agttcatagc   360
ccatatatgg agttccgcgt tacataactt acggtaaatg gcccgcctgg ctgaccgccc   420
```

```
aacgaccccc gcccattgac gtcaataatg acgtatgttc ccatagtaac gccaatagggg    480 actttccatt gacgtcaatg ggtggagtat ttacggtaaa ctgcccactt ggcagtacat    540
caagtgtatc atatgccaag tacgccccct attgacgtca atgacggtaa atggcccgcc    600
tggcattatg cccagtacat gaccttatgg actttccta cttggcagta catctacgta    660
ttagtcatcg ctattaccat ggtgatgcgg ttttggcagt acatcaatgg gcgtggatag    720
cggtttgact cacggggatt tccaagtctc cacccccattg acgtcaatgg gagtttgttt    780
tggcaccaaa atcaacggga ctttccaaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgcccta cct gaggccgcca   1020 tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctccccttg   1140 gagcctacct agactcagcc ggctctccac gctttgcctg accctgcttg ctcaactcta   1200
gttctctcgt tctaatgatt tttatcaaaa tcattaagtt aaggtagata cacatcttgt   1260
catatgatca aatggttcg ccaaaaatca ataatcagac aacaagatgt gcgaactcga   1320 tatttttacac gactctcttt accaattcta ccacaactta atgagacaga tagaaactgg   1380
tcttgtagaa acagagtagt cgcctgcttt tctgccaggt gctgacttct ctcccctggg   1440
ctttttcctt tttctcaggt tgaaaagaag aagacgaaga agacgaagaa gacaaaccgt   1500
cgtcgacaga tcttttttccc tctgccaaaa attatgggga catcatgaag ccccttgagc   1560
atctgacttc tggctaataa aggaaattta ttttcattgc aatagtgtgt tggaatttt    1620 tgtgtctctc actcggaagg acataagggc ggccgctagc                        1660
```

<210> SEQ ID NO 40
<211> LENGTH: 1660
<212> TYPE: DNA
<213> ORGANISM: Artificial Sequence
<220> FEATURE:
<223> OTHER INFORMATION: Description of Artificial Sequence:
      NTC9385Ra-O1 vector backbone

<400> SEQUENCE: 40

```
ccgcctaatg agcgggcttt tttttggctt gttgtccaca accgttaaac cttaaaagct    60

ttaaaagcct tatatattct ттттттттcтт ataaaactta aaaccttaga ggctatttaa   120
gttgctgatt tatattaatt ttattgttca aacatgagag cttagtacgt gaaacatgag   180
agcttagtac gttagccatg agagcttagt acgttagcca tgagggttta gttcgttaaa   240
catgagagct tagtacgtta aacatgagag cttagtacgt actatcaaca ggttgaactg   300
ctgatccacc ccggctctag ттаттаатад таатсaaттa cggggтcaтт agttcatagc   360 ccatatatgg agttccgcgt tacataactt acggtaaatg gcccgcctgg ctgaccgccc   420
aacgaccccc gcccattgac gtcaataatg acgtatgttc ccatagtaac gccaataggg   480
actttccatt gacgtcaatg ggtggagtat ttacggtaaa ctgcccactt ggcagtacat   540
caagtgtatc atatgccaag tacgccccct attgacgtca atgacggtaa atggcccgcc   600
tggcattatg cccagtacat gaccttatgg actttccta cttggcagta catctacgta   660
ttagtcatcg ctattaccat ggtgatgcgg ttttggcagt acatcaatgg gcgtggatag   720
cggtttgact cacggggatt tccaagtctc саcccccaттg acgtcaatgg gagtttgttt   780
```

```
tggcaccaaa atcaacggga cttttccaaaa tgtcgtaaca actccgcccc attgacgcaa    840
atgggcggta ggcgtgtacg gtgggaggtc tatataagca gagctcgttt agtgaaccgt    900
cagatcgcct ggagacgcca tccacgctgt tttgacctcc atagaagaca ccgggaccga    960
tccagcctcc gcggctcgca tctctccttc acgcgcccgc cgccctacct gaggccgcca   1020
tccacgccgg ttgagtcgcg ttctgccgcc tcccgcctgt ggtgcctcct gaactgcgtc   1080
cgccgtctag gtaagtttaa agctcaggtc gagaccgggc ctttgtccgg cgctcccttg   1140
gagcctacct agactcagcc ggctctccac gctttgcctg accctgcttg ctcaactcta   1200
gttctctcgt tgtggtagaa ttggtaaaga gagtcgtgta aaatatcgag ttcgcacatc   1260
ttgttgtctg attattgatt tttggcgaaa ccatttgatc atatgacaag atgtgtatct   1320
accttaactt aatgattttg ataaaaatca ttagaactta atgagacaga tagaaactgg   1380
tcttgtagaa acagagtagt cgcctgcttt tctgccaggt gctgacttct ctcccctggg   1440
ctttttcctt tttctcaggt tgaaaagaag aagacgaaga agacgaagaa gacaaaccgt   1500
cgtcgacaga tcttttcccc tctgccaaaa attatgggga catcatgaag ccccttgagc   1560
atctgacttc tggctaataa aggaaattta ttttcattgc aatagtgtgt tggaattttt   1620
tgtgtctctc actcggaagg acataagggc ggccgctagc                         1660
```

<210> SEQ ID NO 41
<211> LENGTH: 1763
<212> TYPE: DNA
<213> ORGANISM: Artificial Sequence
<220> FEATURE:
<223> OTHER INFORMATION: Description of Artificial Sequence: NTC9385R-BE
      vector backbone

<400> SEQUENCE: 41

```
ccgcctaatg agcgggcttt ttttggctt gttgtccaca accgttaaac cttaaaagct     60
ttaaaagcct tatatattct ttttttttctt ataaaactta aaaccttaga ggctatttaa   120
gttgctgatt tatattaatt ttattgttca acatgagag cttagtacgt gaaacatgag    180
agcttagtac gttagccatg agagcttagt acgttagcca tgagggttta gttcgttaaa   240
catgagagct tagtacgtta aacatgagag cttagtacgt actatcaaca ggttgaactg   300
ctgatccacg ttgtggtaga attggtaaag agagtcgtgt aaaatatcga gttcgcacat   360
cttgttgtct gattattgat ttttggcgaa accatttgat catatgacaa gatgtgtatc   420
taccttaact taatgattt gataaaaatc attaggtacc ccggctctag atggccattg   480
catacgttgt atccatatca taatatgtac atttatattg gctcatgtcc aacattaccg   540
ccatgttgac attgattatt gactagttat taatagtaat caattacggg gtcattagtt   600
catagcccat atatggagtt ccgcgttaca taacttacgg taaatggccc gcctggctga   660
ccgcccaacg acccccgccc attgacgtca ataatgacgt atgttcccat agtaacgcca   720
atagggactt tccattgacg tcaatgggtg gagtatttac ggtaaactgc ccacttggca   780
gtacatcaag tgtatcatat gccaagtacg ccccctattg acgtcaatga cggtaaatgg   840
cccgcctggc attatgccca gtacatgacc ttatgggact ttcctacttg gcagtacatc   900
tacgtattag tcatcgctat taccatggtg atgcggtttt ggcagtacat caatgggcgt   960
ggatagcggt ttgactcacg gggatttcca agtctccacc ccattgacgt caatgggagt  1020
ttgttttggc accaaaatca acgggacttt ccaaaatgtc gtaacaactc cgccccattg  1080
acgcaaatgg gcggtaggcg tgtacggtgg gaggtctata taagcagagc tcgtttagtg  1140
```

```
aaccgtcaga tcgcctggag acgccatcca cgctgttttg acctccatag aagacaccgg   1200
gaccgatcca gcctccgcgg ctcgcatctc tccttcacgc gcccgccgcc ctacctgagg   1260
ccgccatcca cgccggttga gtcgcgttct gccgcctccc gctgtggtg cctcctgaac    1320 tgcgtccgcc gtctaggtaa gtttaaagct caggtcgaga ccgggccttt gtccggcgct   1380
cccttggagc ctacctagac tcagccggct ctccacgctt tgcctgaccc tgcttgctca   1440
actctagttc tctcgttaac ttaatgagac agatagaaac tggtcttgta gaaacagagt   1500
agtcgcctgc ttttctgcca ggtgctgact tctctcccct gggcttttt cttttctca     1560 ggttgaaaag aagaagacga agaagacgaa gaagacaaac cgtcgtcgac agatcttttt   1620
ccctctgcca aaaattatgg ggacatcatg aagccccttg agcatctgac ttctggctaa   1680
taaaggaaat ttattttcat tgcaatagtg tgttggaatt ttttgtgtct ctcactcgga   1740
aggacataag ggcggccgct agc                                           1763

<210> SEQ ID NO 42
<211> LENGTH: 678
<212> TYPE: DNA
<213> ORGANISM: Artificial Sequence
<220> FEATURE:
<223> OTHER INFORMATION: Description of Artificial Sequence: Pmin
      minimal pUC replication origin

<400> SEQUENCE: 42
cgcgttgctg gcgttttca taggctccgc cccctgacg agcatcacaa aaatcgacgc      60
tcaagtcaga ggtggcgaaa cccgacagga ctataaagat accaggcgtt tccccctgga   120
agctccctcg tgcgctctcc tgttccgacc ctgccgctta ccggatacct gtccgccttt   180
ctcccttcgg gaagcgtggc gctttctcat agctcacgct gtaggtatct cagttcggtg   240
taggtcgttc gctccaagct gggctgtgtg cacgaacccc ccgttcagcc cgaccgctgc   300
gccttatccg gtaactatcg tcttgagtcc aacccggtaa gacacgactt atcgccactg   360
gcagcagcca ctggtaacag gattagcaga gcgaggtatg taggcggtgc tacagagttc   420
ttgaagtggt ggcctaacta cggctacact agaagaacag tatttggtat ctgcgctctg   480
ctgaagccag ttaccttcgg aaaaagagtt ggtagctctt gatccggcaa acaaaccacc   540
gctggtagcg gtggttttt tgtttgcaag cagcagatta cgcgcagaaa aaaggatct    600 caagaagatc ctttgatctt ttctacgggg tctgacgctc agtggaacga aaactcacgt   660
taagggattt tggtcatg                                                 678

<210> SEQ ID NO 43
<211> LENGTH: 866
<212> TYPE: DNA
<213> ORGANISM: Artificial Sequence
<220> FEATURE:
<223> OTHER INFORMATION: Description of Artificial Sequence: pUC (0.85)
      Bacterial region [NheI site- trpA terminator-Pmin pUC replication
      origin (minimal)-RNA-OUT-KpnI site]

<400> SEQUENCE: 43
gctagcccgc ctaatgagcg ggcttttttt tcttaggcct cgcgttgctg gcgttttca    60 taggctccgc cccctgacg agcatcacaa aaatcgacgc tcaagtcaga ggtggcgaaa   120
cccgacagga ctataaagat accaggcgtt tccccctgga agctccctcg tgcgctctcc   180
tgttccgacc ctgccgctta ccggatacct gtccgccttt ctcccttcgg gaagcgtggc   240
gctttctcat agctcacgct gtaggtatct cagttcggtg taggtcgttc gctccaagct   300
```

```
gggctgtgtg cacgaacccc ccgttcagcc cgaccgctgc gccttatccg gtaactatcg    360
tcttgagtcc aacccggtaa gacacgactt atcgccactg gcagcagcca ctggtaacag    420
gattagcaga gcgaggtatg taggcggtgc tacagagttc ttgaagtggt ggcctaacta    480
cggctacact agaagaacag tatttggtat ctgcgctctg ctgaagccag ttaccttcgg    540
aaaaagagtt ggtagctctt gatccggcaa acaaaccacc gctggtagcg gtggtttttt    600
tgtttgcaag cagcagatta cgcgcagaaa aaaggatct caagaagatc ctttgatctt     660
ttctacgggg tctgacgctc agtggaacga aaactcacgt taagggattt tggtcatggt    720
ggtagaattg gtaaagagag tcgtgtaaaa tatcgagttc gcacatcttg ttgtctgatt    780
attgattttt ggcgaaacca tttgatcata tgacaagatg tgtatctacc ttaacttaat    840
gattttgata aaaatcatta ggtacc                                         866

<210> SEQ ID NO 44
<211> LENGTH: 146
<212> TYPE: DNA
<213> ORGANISM: Artificial Sequence
<220> FEATURE:
<223> OTHER INFORMATION: Description of Artificial Sequence: PL promoter
      with locations of the PL promoter OL1, OL2 and OL3 repressor
      binding sites, -10 and -35 promoter elements for PL1 and PL2
      promoters

<400> SEQUENCE: 44
agcaattcag atctctcacc taccaaacaa tgcccccctg caaaaaataa attcatataa     60
aaaacataca gataaccatc tgcggtgata aattatctct ggcggtgttg acataaatac    120
cactggcggt gatactgagc acatca                                         146
```

DNA PLASMIDS WITH IMPROVED EXPRESSION

CROSS REFERENCE TO RELATED APPLICATIONS

This application is a division of U.S. application Ser. No. 14/422,865, filed Feb. 20, 2015, which is a 371 U.S. National Phase application of PCT/US2013/000068, filed Mar. 14, 2013 which claim the benefit of U.S. Provisional Application Ser. No. 61/743,219, filed Aug. 29, 2012 entitled "DNA Plasmids With Improved Expression". The entire disclosures of each of the above-identified applications are incorporated herein by reference.

Applicants submit herewith a computer readable form (CRF) of the Sequence Listing for entry into this application. The content of the Sequence Listing information recorded in computer readable form includes no new matter beyond the scope of the published International Application.

STATEMENT REGARDING FEDERALLY SPONSORED RESEARCH OR DEVELOPMENT

This invention was supported in part with government support under Grant No. R44GM080768, awarded by the National Institutes of Health. The government has certain rights in this invention.

FIELD OF THE INVENTION

The present invention relates to a family of eukaryotic expression plasmids useful for gene therapy, obtaining improved genetic immunization, natural interferon production, and more particularly, for improving the expression of plasmid encoded antigens, therapeutic proteins and RNAs.

The present invention also relates to the production of covalently closed circular (ccc) recombinant DNA molecules such as plasmids, cosmids, bacterial artificial chromosomes (BACs), bacteriophages, viral vectors and hybrids thereof, and more particularly to strain modifications that improve production yield of said DNA molecules in fermentation culture.

Such recombinant DNA molecules are useful in biotechnology, transgenic organisms, gene therapy, therapeutic vaccination, agriculture and DNA vaccines.

BACKGROUND OF THE INVENTION

E. coli plasmids have long been an important source of recombinant DNA molecules used by researchers and by industry. Today, plasmid DNA is becoming increasingly important as the next generation of biotechnology products (e.g., gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to the patient.

Therapeutic plasmids often contain a pMB1, ColE1 or pBR322 derived replication origin. Common high copy number derivatives have mutations affecting copy number regulation, such as ROP (Repressor of primer gene) deletion, with a second site mutation that increases copy number (e.g. pMB1 pUC G to A point mutation, or ColE1 pMM1). Higher temperature (42° C.) can be employed to induce selective plasmid amplification with pUC and pMM1 replication origins.

U.S. Pat. No. 7,943,377 (Carnes, A E and Williams, J A, 2011) disclose methods for fed-batch fermentation, in which plasmid-containing E. coli cells were grown at a reduced temperature during part of the fed-batch phase, during which growth rate was restricted, followed by a temperature upshift and continued growth at elevated temperature in order to accumulate plasmid; the temperature shift at restricted growth rate improved yield and purity of plasmid. Other fermentation processes for plasmid production are described in Carnes A. E. 2005 BioProcess Intl; 3:36-44, which is incorporated herein by reference in its entirety.

The art teaches that one of the limitations of application of plasmid therapies and plasmid vaccines is regulatory agency (e.g. Food and Drug Administration, EMEC) safety concerns regarding 1) plasmid transfer and replication in endogenous bacterial flora, or 2) plasmid encoded selection marker expression in human cells, or endogenous bacterial flora. Additionally, regulatory agency guidances recommend removal of all non essential sequences in a vector. Plasmids containing a pMB1, ColE1 or pBR322 derived replication origin can replicate promiscuously in E. coli hosts. This presents a safety concern that a plasmid therapeutic gene or antigen will be transferred and replicated to a patient's endogenous flora. Ideally, a therapeutic or vaccine plasmid would be replication incompetent in endogenous E. coli strains. This requires replacement of the pMB1, ColE1 or pBR322 derived replication origin with a conditional replication origin that requires a specialized cell line for propagation. As well, regulatory agencies such as the EMEA and FDA are concerned with utilization of antibiotic resistance or alternative protein markers in gene therapy and gene vaccine vectors, due to concerns that the gene (antibiotic resistance marker or protein marker) may be expressed in a patients cells. Ideally, plasmid therapies and plasmid vaccines would be 1) replication incompetent in endogenous E. coli strains, 2) would not encode a protein based selection marker and 3) be minimalized to eliminate all non essential sequences.

The art further teaches that one of the limitations of application of plasmid therapies and vaccines is that antigen expression is generally very low. Vector modifications that improve antigen expression (e.g. codon optimization of the gene, inclusion of an intron, use of the strong constitutive CMV or CAGG promoters versus weaker or cell line specific promoter) are highly correlative with improved in vivo expression and, where applicable, immune responses (reviewed in Manoj S, Babiuk L A, van Drunen Little-van den Hurk S. 2004 Crit Rev Clin Lab Sci 41: 1-39). A hybrid CMV promoter (CMV/R), which increased antigen expression, also improved cellular immune responses to HIV DNA vaccines in mice and nonhuman primates (Barouch D H, Yang Z Y, Kong W P, Korioth-Schmitz B, Sumida S M, Truitt D M, Kishko M G, Arthur J C, Miura A, Mascola J R, Letvin N L, Nabel G J. 2005 J Virol. 79: 8828-8834). A plasmid containing the woodchuck hepatitis virus posttranscriptional regulatory element (a 600 bp element that increases stability and extranuclear transport of RNA resulting in enhanced levels of mRNA for translation) enhanced antigen expression and protective immunity to influenza hemagglutinin (HA) in mice (Garg S, Oran A E, Hon H, Jacob J. 2004 J Immunol. 173: 550-558). These studies teach that improvement in expression beyond that of current CMV based vectors may generally improve immunogenicity and, in the case of gene therapeutics, efficacy.

SUMMARY OF THE INVENTION

The present invention relates to a family of minimalized eukaryotic expression plasmids that are replication incompetent in endogenous flora and have dramatically improved in vivo expression. These vectors are useful for gene therapy, genetic immunization and or interferon therapy.

The present invention also relates generally to methods of increasing production yield of covalently closed supercoiled plasmid DNA.

Improved vectors that utilize novel replication origins that unexpectedly improve antigen expression are disclosed.

One object of the invention is to provide improved expression plasmid vectors. Yet another object of the invention is to provide methods for improving plasmid copy number.

According to one object of the invention, a method of increasing expression from an expression plasmid vector comprises modifying the plasmid DNA to replace the pMB1, ColE1 or pBR322 derived replication origin and selectable marker with an alternative replication origin selected from the group consisting of an minimal pUC origin, a R6K gamma replication origin, a ColE2-P9 replication origin, and a ColE2-P9 related replication origin and an RNA selectable marker; transforming the modified plasmid DNA into a bacterial cell line rendered competent for transformation; and isolating the resultant transformed bacterial cells. The resultant plasmid surprisingly has higher in vivo expression levels than the parent pMB1, ColE1 or pBR322 derived replication origin expression plasmid vector.

According to one object of the invention, a composition for construction of a eukaryotic expression vector comprises an R6K origin with at least 90% sequence identity to the sequence set forth as SEQ ID NO: 1, and a RNA selectable marker, wherein said R6K origin is operably linked to said RNA selectable marker and a eukaryotic region. According to another object of the invention, said R6K origin-RNA selectable marker improves said vector expression in vivo compared to a corresponding vector containing a pMB1, ColE1 or pBR322 derived replication origin. According to still another object of the invention, said vector has at least 95% sequence identity to a sequence selected from the group consisting of: SEQ ID NO: 2, SEQ ID NO: 3, SEQ ID NO:41.

According to one object of the invention, a composition for construction of a eukaryotic expression vector comprises a ColE2-P9 origin with at least 90% sequence identity to the sequence set forth as SEQ ID NO: 4, 5, 6, or 7, and a a RNA selectable marker, wherein said ColE2-P9 origin—a RNA selectable marker is operably linked to a eukaryotic region. According to another object of the invention, said ColE2-P9 origin-RNA selectable marker improves said vector expression in vivo compared to a corresponding vector containing a pMB1, ColE1 or pBR322 derived replication origin. According to still another object of the invention, said vector has at least 95% sequence identity to a sequence selected from the group consisting of: SEQ ID NO: 8, SEQ ID NO: 9. According to still another object of the invention, a primosomal assembly site (ssiA) is optionally incorporated into the vector adjacent to the ColE2-P9 origin.

According to another object of the invention, production cell lines are disclosed that improve plasmid yield in shake flask and or fermentation culture with said R6K gamma replication origin, ColE2-P9 replication origin, or ColE2-P9 related replication origin plasmid vectors of the current invention.

According to another object of the invention, production cell lines providing heat inducible induction of R6K gamma replication origin, ColE2-P9 replication origin, or ColE2-P9 related replication origin plasmid vectors for DNA production are disclosed. These cell lines contain one or more copies of the corresponding R6K gamma replication origin, ColE2-P9 replication origin, or ColE2-P9 related replication protein integrated into the genome and expressed from the group consisting of: the heat inducible $P_L$ promoter (SEQ ID NO: 10), the heat inducible $P_L$ promoter incorporating the OL1-G deletion (SEQ ID NO: 11), the heat inducible $P_L$ promoter incorporating the OL1-G to T substitution (SEQ ID NO: 12).

According to another object of the invention, mutant R6K replication proteins that improve heat inducible induction of R6K gamma replication origin vectors are disclosed. These cell lines contain one or more copies of the mutant R6K gamma replication origin replication protein integrated into the genome and expressed from the group consisting of: the heat inducible $P_L$ promoter (SEQ ID NO: 10), the heat inducible $P_L$ promoter incorporating the OL1-G deletion (SEQ ID NO: 11), the heat inducible $P_L$ promoter incorporating the OL1-G to T substitution (SEQ ID NO: 12). The mutant R6K gamma replication origin replication protein are selected from the group consisting of: P42L-P113S (SEQ ID NO: 13), P42L-P106L-F107S (SEQ ID NO: 14).

According to another object of the invention, a mutant ColE2-P9 replication protein that improve heat inducible induction of ColE2-P9 replication origin vectors is disclosed. These cell lines contain one or more copies of the mutant ColE2-P9 replication origin replication protein integrated into the genome and expressed from the group consisting of: the heat inducible $P_L$ promoter (SEQ ID NO: 10), the heat inducible $P_L$ promoter incorporating the OL1-G deletion (SEQ ID NO: 11), the heat inducible $P_L$ promoter incorporating the OL1-G to T substitution (SEQ ID NO: 12). The mutant ColE2-P9 replication origin replication protein is ColE2-P9 Rep mut G194D (SEQ ID NO: 16).

Further objects and advantages of the invention will become apparent from a consideration of the drawings and ensuing description.

Figure 1:
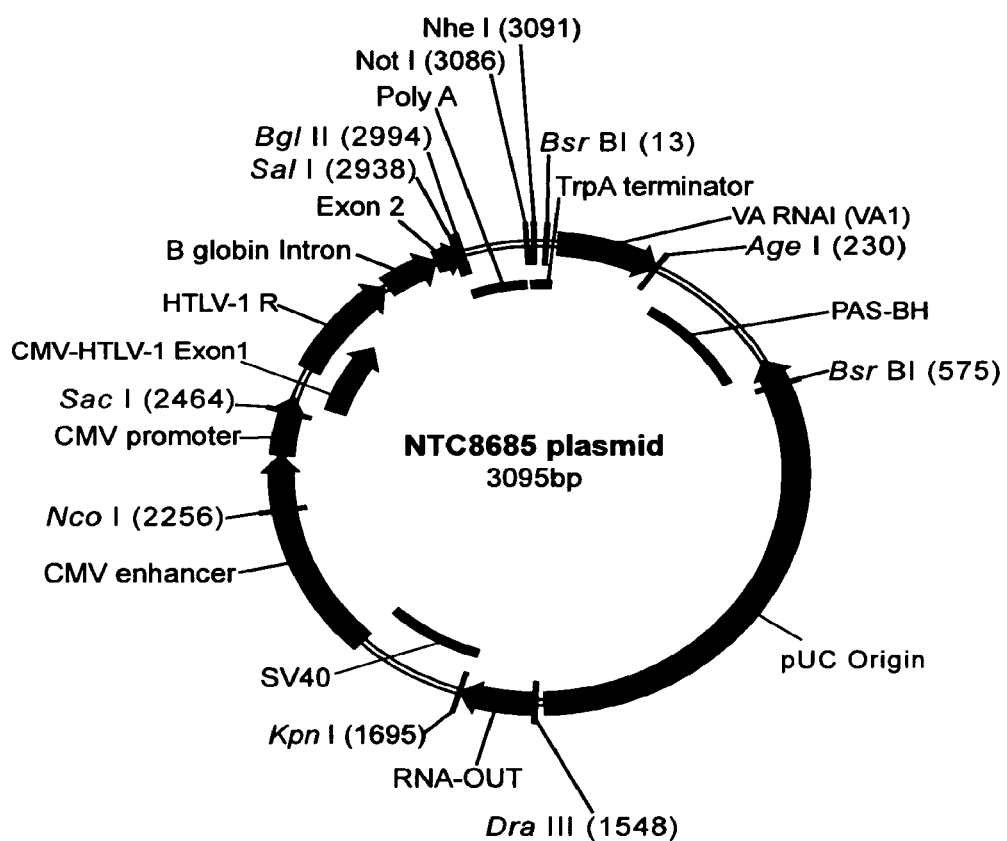
FIG. 1 depicts the NTC8685 pUC origin expression vector.

Table 1: P$_L$ promoter with OL1 mutations OL1-G and OL1-G to T improve plasmid yields in HyperGRO fermentation Table 2: NTC9385R-EGFP LB media shake flask production yields in R6K production strains Table 3: NTC9385C-Luc plasmid performance in different processes and production cell lines Table 4: ColE2 Origin EGFP vector production in NTC701131 ColE2 production cell line Table 5: NTC9382C, NTC9385C, NTC9382R, NTC9385R, NTC9682C, NTC9685C, NTC9682R, and NTC9685R vectors Table 6: gWIZ and NTC9385C Nanoplasmid expression compared to NTC8685

Table 7: SR vector expression in vitro and in vivo

Table 8: RNA Pol III Nanoplasmid vector expression

Table 9: High level expression is obtained with pMB1 RNAI or RNA-OUT antisense RNA vectors SEQ ID NO:1: R6K gamma Origin
SEQ ID NO:2: NTC9385R vector backbone
SEQ ID NO:3: NTC9685R vector backbone
SEQ ID NO:4: ColE2 Origin (+7)
SEQ ID NO:5: ColE2 Origin (+7, CpG free)
SEQ ID NO:6: ColE2 Origin (Min)
SEQ ID NO:7: ColE2 Origin (+16)
SEQ ID NO:8: NTC9385C vector backbone
SEQ ID NO:9: NTC9685C vector backbone
SEQ ID NO:10: P$_L$ Promoter (−35 to −10)
SEQ ID NO:11: P$_L$ Promoter OL1-G (−35 to −10)
SEQ ID NO:12: P$_L$ Promoter OL1-G to T(−35 to −10)
SEQ ID NO:13: R6K Rep protein P42L-P113S
SEQ ID NO:14: R6K Rep protein P42L-P106L-F107S
SEQ ID NO:15: ColE2 Rep protein (wild type)
SEQ ID NO:16: ColE2 Rep protein mut (G194D)
SEQ ID NO:17: pINT pR pL R6K Rep piP42L-P106L-F107S (P3−)
SEQ ID NO:18: pINT pR pL ColE2 Rep protein mut (G194D)
SEQ ID NO:19: NTC9385R and NTC9685R Bacterial region. [NheI site-trpA terminator-R6K Origin-RNA-OUT-KpnI site]
SEQ ID NO:20: NTC9385C and NTC9685C Bacterial region. [NheI site-ssiA-ColE2 Origin (+7)-RNA-OUT-KpnI site]
SEQ ID NO:21: NTC9385C and NTC9685C CpG free ssiA [from plasmid R6K]
SEQ ID NO:22: CpG free R6K origin
SEQ ID NO:23: RNA-OUT selectable marker from NTC9385C, NTC9685C, NTC9385R, and NTC9685R
SEQ ID NO:24: RNA-OUT Sense strand RNA from NTC9385C, NTC9685C, NTC9385R, NTC9685R, and NTC9385Ra
SEQ ID NO:25: TPA secretion sequence
SEQ ID NO:26: PCR primer 15061101
SEQ ID NO:27: PCR primer 15061102
SEQ ID NO:28: ColE2 core replication origin
SEQ ID NO:29: +7(CpG free)-ssiA ColE2 origin
SEQ ID NO:30: HTLV-IR-Rabbit β globin hybrid intron
SEQ ID NO:31: pMB1 RNAI antisense repressor RNA (origin antisense partner of RNAII)
SEQ ID NO:32: pMB1 RNAI selectable Marker, RNAI RNA (Sense strand)
SEQ ID NO:33: IncB RNAI antisense repressor RNA (IncB plasmid origin RNAII antisense partner)
SEQ ID NO:34: IncB RNAI selectable Marker. DraIII-KpnI restriction fragment
SEQ ID NO:35: IncB RNAII-SacB. PstI-MamI restriction fragment
SEQ ID NO:36: CpG free RNA-OUT selection marker—flanked by KpnI and BglII-EcoRI sites
SEQ ID NO:37: CpG free R6K gamma—RNA-OUT bacterial region (CpG free R6K origin-CpG free RNA-OUT selection marker)—flanked by EcoRI-SphI and BglII-EcoRI sites
SEQ ID NO:38: CpG free ColE2 bacterial region (CpG free ssiA-CpG free ColE2 origin-CpG free RNA-OUT selection marker)-flanked by EcoRI-SphI and BglII-EcoRI sites
SEQ ID NO:39: NTC9385Ra-O2 vector backbone
SEQ ID NO:40: NTC9385Ra-O1 vector backbone
SEQ ID NO:41: NTC9385R-BE vector backbone
SEQ ID NO:42: P$_{min}$ minimal pUC replication origin
SEQ ID NO:43: pUC (0.85) Bacterial region [NheI site—trpA terminator-P$_{min}$ pUC replication origin (minimal)-RNA-OUT-KpnI site]
SEQ ID NO:44: artificial sequence including a P$_L$ promoter Definition of Terms A$_{405}$: Absorbance at 405 nanometers
AF: Antibiotic-free
APC: Antigen Processing Cell, for example, langerhans cells, plasmacytoid or conventional dendritic cells
Approximately: As used herein, the term "approximately" or "about," as applied to one or more values of interest, refers to a value that is the same or similar to a stated reference value
BAC: Bacterial artificial chromosome
Bacterial region: Region of a plasmid vector required for propagation and selection in the bacterial host
BE: Boundary element: Eukaryotic sequence that that blocks the interaction between enhancers and promoters. Also referred to as insulator element. An example is the AT-rich unique region upstream of the CMV enhancer SpeI site that can function as an insulator/boundary element (Angulo A, Kerry D, Huang H, Borst E M, Razinsky A, Wu J et al. 2000 *J Virol* 74: 2826-2839)
bp: basepairs
ccc: Covalently Closed Circular
cI: Lambda repressor
cITs857: Lambda repressor further incorporating a C to T (Ala to Thr) mutation that confers temperature sensitivity. cITs857 is a functional repressor at 28-30° C., but is mostly inactive at 37-42° C. Also called cI857
Cm$^R$: Chloramphenicol resistance
cmv: Cytomegalovirus
CMV promoter boundary element: AT-rich region of the human cytomegalovirus (CMV) genome between the UL127 open reading frame and the major immediate-early (MIE) enhancer. Also referred to as unique region (Angulo et al. Supra, 2000)
ColE2-P9 replication origin: a region which is specifically recognized by the plasmid-specified Rep protein to initiate DNA replication. Includes but not limited to ColE2-P9 replication origin sequences disclosed in SEQ ID NO:4: ColE2 Origin (+7), SEQ ID NO:5: ColE2 Origin (+7, CpG free), SEQ ID NO:6: ColE2 Origin (Min) and SEQ ID NO:7: ColE2 Origin (+16) and replication functional mutations as disclosed in Yagura et al 2006, *J Bacteriol* 188:999-1010 included herein by reference ColE2 related replication origin: The ColE2-P9 origin is highly conserved across the ColE2-related plasmid family. Fifteen ColE2 related plasmid members including ColE3 are compared in Hiraga et al 1994, *J Bacteriol.* 176:7233 and 53 ColE2 related plasmid members including ColE3 are compared in Yagura et al Supra, 2006. These sequences are included herein by reference ColE2-P9 plasmid: a circular duplex DNA molecule of about 7 kb that is maintained at about 10 to 15 copies per host chromosome. The plasmid encodes an initiator protein (Rep protein), which is the only plasmid-specified trans-acting factor essential for ColE2-P9 plasmid replication ColE2-P9 replication origin RNA-OUT bacterial region: Contains a ColE2-P9 replication origin for propagation and the RNA-OUT selection marker. Optionally includes a PAS, for example, the R6K plasmid CpG free ssiA primosomal assembly site (SEQ ID NO:21) or alternative ØX174 type or ABC type primosomal assembly sites, such as those disclosed in Nomura et al 1991 *Gene* 108:15

ColE2 plasmid: NTC9385C and NTC9685C vectors disclosed herein, as well as modifications and alternative vectors containing a ColE2-P9 replication origin delivery methods: Methods to deliver gene vectors [e.g. poly(lactide-co-glycolide) (PLGA), ISCOMs, liposomes, niosomes, virosomes, chitosan, and other biodegradable polymers, electroporation, piezoelectric permeabilization, sonoporation, ultrasound, corona plasma, plasma facilitated delivery, tissue tolerable plasma, laser microporation, shock wave energy, magnetic fields, contactless magneto-permeabilization, gene gun, microneedles, naked DNA injection, hydrodynamic delivery, high pressure tail vein injection, needle free biojector, liposomes, microparticles, microspheres, nanoparticles, virosomes, bacterial ghosts, bacteria, attenuated bacteria, etc] as known in the art and included herein by reference DNA replicon: A genetic element that can replicate under its own control; examples include plasmids, cosmids, bacterial artificial chromosomes (BACs), bacteriophages, viral vectors and hybrids thereof E. coli: *Escherichia coli*, a gram negative bacteria EGFP: Enhanced green fluorescent protein EP: Electroporation Eukaryotic expression vector: A vector for expression of mRNA, protein antigens, protein therapeutics, shRNA, RNA or microRNA genes in a target organism Eukaryotic region: The region of a plasmid that encodes eukaryotic sequences and/or sequences required for plasmid function in the target organism. This includes the region of a plasmid vector required for expression of one or more transgenes in the target organism including RNA Pol II enhancers, promoters, transgenes and polyA sequences. A eukaryotic region may express protein or RNA genes using one or more RNA Pol II promoters, or express RNA genes using one or more RNA Pol III promoters or encode both RNA Pol II and RNA Pol III expressed genes. Additional functional eukaryotic region sequences include RNA Pol I or RNA Pol III promoters, RNA Pol I or RNA Pol III expressed transgenes or RNAs, transcriptional terminators, S/MARs, boundary elements, etc FU: Fluorescence units g: Gram, kg for kilogram Hr(s): Hour(s)

HTLV-I R: HTLV-I R 5' untranslated region (UTR). Sequences and compositions were disclosed in Williams, J A 2008 World Patent Application WO2008153733 and included herein by reference IM: Intramuscular immune response: Antigen reactive cellular (e.g. antigen reactive T cells) or antibody (e.g. antigen reactive IgG) responses IncB RNAI: plasmid pMU720 origin encoded RNAI (SEQ ID NO: 33) that represses RNA II regulated targets (Wilson I W, Siemering K R, Praszkier J, Pittard A J. 1997. J Bacteriol 179:742)

kan: Kanamycin kanR: Kanamycin Resistance gene

Figure 7:
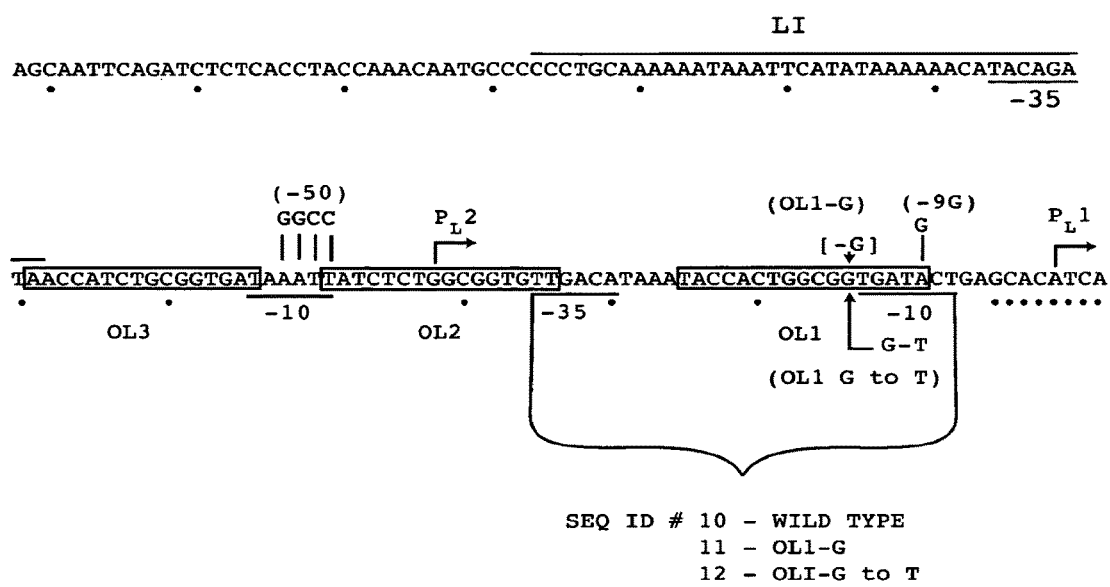
FIG. 7 depicts SEQ ID NO: 44, which includes the $P_L$ promoter with OL1 mutations OL1-G and OL1-G to T.

Kd: Kilodalton kozak sequence: Optimized sequence of consensus DNA sequence gccRccATG (R=G or A) immediately upstream of an ATG start codon that ensures efficient tranlation initiation. A SalI site (GTCGAC) immediately upstream of the ATG start codon (GTCGACATG) is an effective Kozak sequence Minicircle: Covalently closed circular plasmid derivatives in which the bacterial region has been removed from the parent plasmid by in vivo or in vitro intramolecular (cis-) site specific recombination or in vitro restriction digestion/ligation mSEAP: Murine secreted alkaline phosphatase Nanoplasmid vector: Vector combining an RNA selection marker with a R6K or ColE2 related replication origin. For example, NTC9385C, NTC9685C, NTC9385R, NTC9685R, NTC9385R-BE, NTC9385Ra-O1 and NTC9385Ra-O2 vectors described herein and modifications thereof NTC7382 promoter: A chimeric promoter comprising the CMV enhancer-CMV promoter-HTLV R-synthetic rabbit β globin 3' intron acceptor-exon 2-SRF protein binding site-kozak sequence, with or without an upstream SV40 enhancer. The creation and application of this chimeric promoter is disclosed in Williams J A Supra, 2008 and included herein by reference NTC8385: NTC8385 and NTC8685 plasmids are antibiotic-free vectors that contain a short RNA (RNA-OUT) selection marker in place of the antibiotic resistance marker (kanR) The creation and application of these RNA-OUT based antibiotic-free vectors are disclosed in Williams, J A Supra, 2008 and included herein by reference NTC8685: NTC8685 (FIG. 1) is an antibiotic-free vector that contains a short RNA (RNA-OUT) selection marker in place of the antibiotic resistance marker (kanR) The creation and application of NTC8685 is disclosed in Williams, J A 2010 US Patent Application 20100184158 and included herein by reference OL1: Lambda repressor binding site in the $P_L$ promoter (FIG. 7). Repressor binding to OL1 is altered by mutations in OL1, such as OL1-G (FIG. 7; this is a single base deletion that also reduces the distance between the $P_L$ promoter −35 and −10 boxes from optimal 17 bp to 16 bp) and OL1-G to T (FIG. 7; this is a G to T substitution that maintains the distance between the $P_L$ promoter −35 and −10 boxes at the optimal 17 bp; this is the V2 mutation described by Bailone A and Galibert F, 1980. *Nucleic Acids Research* 8:2147)

$OD_{600}$: optical density at 600 nm

PAS: Primosomal assembly site. Priming of DNA synthesis on a single stranded DNA ssi site. ØX174 type PAS: DNA hairpin sequence that binds priA, which, in turn, recruits the remaining proteins to form the preprimosome [priB, dnaT, recruits dnaB (delivered by dnaC)], which then also recruits primase (dnaG), which then, finally, makes a short RNA substrate for DNA polymerase I. ABC type PAS: DNA hairpin binds dnaA, recruits dnaB (delivered by dnaC) which then also recruits primase (dnaG), which then, finally, makes a short RNA substrate for DNA polymerase I. See Masai et al, 1990 *J Biol Chem* 265:15134. For example, the R6K plasmid CpG free ssiA primosomal assembly site (SEQ ID NO:21) or alternative ØX174 type or ABC type primosomal assembly sites, such as those disclosed in Nomura et al Supra, 1991

PAS-BH: Primosomal assembly site on the heavy (leading) strand

PAS-BH region: pBR322 origin region between ROP and PAS-BL (approximately pBR322 2067-2351)

PAS-BL: Primosomal assembly site on the light (lagging) strand

PBS: Phosphate buffered Saline

PCR: Polymerase Chain Reaction pDNA: Plasmid DNA pINT pR pL vector: The pINT pR pL integration expression vector is disclosed in Luke et al 2011 *Mol Biotechnol* 47:43 and included herein by reference. The target gene to be expressed is cloned downstream of the pL1 promoter (FIG. 7). The vector encodes the temperature inducible cI857 repressor, allowing heat inducible target gene expression.

$P_L$ promoter: Lambda promoter left (FIG. 7). $P_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues Plasmid: An extra chromosomal DNA molecule separate from the chromosomal DNA which is capable of replicating independently from the chromosomal DNA pMB1 RNAI: pMB1 plasmid origin encoded RNAI that represses RNAII regulated targets (SEQ ID NO: 31; SEQ ID NO:32) that represses RNAII regulated targets such as those described in Grabherr R, Pfaffenzeller I. 2006 US patent application US20060063232 and Cranenburgh R M. 2009; U.S. Pat. No. 7,611,883

$P_{min}$: Minimal 678 bp pUC replication origin SEQ ID NO:42 and functional variants with base substitutions and/or base deletions. Vectors described herein incorporating $P_{min}$ include NTC8385-Min and NTC8885MP-U6

Pol: Polymerase polyA: Polyadenylation signal or site. Polyadenylation is the addition of a poly(A) tail to an RNA molecule. The polyadenylation signal is the sequence motif recognized by the RNA cleavage complex. Most human polyadenylation sites contain an AAUAAA motif and conserved sequences 5' and 3' to it. Commonly utilized polyA sites are derived from the rabbit β globin (NTC8685; FIG. 1), bovine growth hormone (gWIZ; pVAX1), SV40 early, or 5V40 late polyA signals pUC replication origin: pBR322-derived replication origin, with G to A transition that increases copy number at elevated temperature and deletion of the ROP negative regulator pUC plasmid: Plasmid containing the pUC origin R6K plasmid: NTC9385R, NTC9685R, NTC9385Ra-O1 and RNA9385Ra-O2 vectors disclosed herein, as well as modifications, and alternative R6K vectors known in the art including but not limited to pCOR vectors (Gencell), pCpG-free vectors (Invivogen), and CpG free University of Oxford vectors including pGM169

R6K replication origin: a region which is specifically recognized by the plasmid-specified Rep protein to initiate DNA replication. Includes but not limited to R6K replication origin sequence disclosed as SEQ ID NO:1: R6K Origin, and CpG free versions (SEQ ID NO:22) as disclosed in Drocourt et al U.S. Pat. No. 7,244,609 and incorporated herein by reference R6K replication origin-RNA-OUT bacterial region: Contains a R6K replication origin for propagation and the RNA-OUT selection marker Rep: Replication Rep protein dependent plasmid: A plasmid in which replication is dependent on a replication (Rep) protein provided in Trans. For example, R6K replication origin, ColE2-P9 replication origin and ColE2 related replication origin plasmids in which the Rep protein is expressed from the host strain genome. Numerous additional Rep protein dependent plasmids are known in the art, many of which are summarized in del Solar et al 1998 *Microbiol. Mol. Biol. Rev* 62:434-464 which is included herein by reference RNA-IN: Insertion sequence 10 (IS10) encoded RNA-IN, an RNA complementary and antisense to RNA-OUT. When RNA-IN is cloned in the untranslated leader of a mRNA, annealing of RNA-IN to RNA-OUT reduces translation of the gene encoded downstream of RNA-IN RNA-IN regulated selection marker: A genomically expressed RNA-IN regulated selectable marker. In the presence of plasmid borne RNA-OUT, expression of a protein encoded downstream of RNA-IN is repressed. An RNA-IN regulated selection marker is configured such that RNA-IN regulates either 1) a protein that is lethal or toxic to said cell per se or by generating a toxic substance (e.g. SacB), or 2) a repressor protein that is lethal or toxic to said bacterial cell by repressing the transcription of a gene that is essential for growth of said cell (e.g. murA essential gene regulated by RNA-IN tetR repressor gene). For example, genomically expressed RNA-IN-SacB cell lines for RNA-OUT plasmid propagation are disclosed in Williams, J A Supra, 2008 (SEQ ID NO:23) and included herein by reference. Alternative selection markers described in the art may be substituted for SacB RNA-OUT: Insertion sequence 10 (IS10) encoded RNA-OUT (SEQ ID NO:24), an antisense RNA that hybridizes to, and reduces translation of, the transposon gene expressed downstream of RNA-IN. The sequence of the core RNA-OUT sequence (SEQ ID NO:24) and complementary RNA-IN SacB genomically expressed RNA-IN-SacB cell lines can be modified to incorporate alternative functional RNA-IN/RNA-OUT binding pairs such as those disclosed in Mutalik et al. 2012 *Nat Chem Biol* 8:447, including, but not limited to, the RNA-OUT A08/RNA-IN S49 pair, the RNA-OUT A08/RNA-IN S08 pair, and CpG free modifications of RNA-OUT A08 that modify the CG in the RNA-OUT 5' TT CGCT sequence to a non-CpG sequence RNA-OUT Selectable marker: An RNA-OUT selectable marker DNA fragment including *E. coli* transcription promoter and terminator sequences flanking an RNA-OUT RNA. An RNA-OUT selectable marker, utilizing the RNA-OUT promoter and terminator sequences, that is flanked by DraIII and KpnI restriction enzyme sites, and designer genomically expressed RNA-IN-SacB cell lines for RNA-OUT plasmid propagation, are disclosed in Williams, J A Supra, 2008 (SEQ ID NO:23) and included herein by reference. The RNA-OUT promoter and terminator sequences flanking the RNA-OUT RNA may be replaced with heterologous promoter and terminator sequences. For example, the RNA-OUT promoter may be substituted with a CpG free promoter known in the art, for example the I-EC2K promoter or the P5/6 5/6 or P5/6 6/6 promoters disclosed in Williams, J A Supra, 2008 and included herein by reference RNA selectable marker: also RNA selection marker. An RNA selectable marker is a plasmid borne expressed non translated RNA that regulates a chromosomally expressed target gene to afford selection. This may be a plasmid borne nonsense suppressing tRNA that regulates a nonsense suppressible selectable chromosomal target as described by Crouzet J and Soubrier F 2005 U.S. Pat. No. 6,977,174 included herein by reference. This may also be a plasmid borne antisense repressor RNA, a non limiting list included herein by reference includes RNA-OUT that represses RNA-IN regulated targets, pMB1 plasmid origin encoded RNAI that represses RNAII regulated targets (SEQ ID NO: 31; SEQ ID NO:32; Grabherr and, Pfaffenzeller Supra, 2006; Cranenburgh R M. Supra, 2009), IncB plasmid pMU720 origin encoded RNAI that represses RNA II regulated targets (SEQ ID NO: 33; SEQ ID NO:34; Wilson et al Supra, 1997), ParB locus Sok of plasmid R1 that represses Hok regulated targets, Flm locus FlmB of F plasmid that represses flmA regulated targets (Morsey M A, 1999 U.S. Pat. No. 5,922,583). An RNA selectable marker may be another natural antisense repressor RNAs known in the art such as those described in Wagner E G H, Altuvia S, Romby P. 2002. *Adv Genet* 46:361 and Franch T, and Gerdes K. 2000. *Current Opin Microbiol* 3:159. An RNA selectable marker may also be an engineered repressor RNAs such as synthetic small RNAs expressed SgrS, MicC or MicF scaffolds as described in Na D, Yoo S M, Chung H, Park H, Park J H, Lee S Y. 2013. *Nat Biotechnol* 31:170

ROP: Repressor of primer sacB: Structural gene encoding *Bacillus subtilis* levansucrase. Expression of sacB in gram negative bacteria is toxic in the presence of sucrose SEAP: Secreted alkaline phosphatase shRNA: Short hairpin RNA SR: Spacer region. As used herein, spacer region is the region linking the 5' and 3' ends of the eukaryotic region sequences. The eukaryotic region 5' and 3' ends are typically separated by the replication origin and selection marker. In simple single RNA Pol II transcription vectors this will be between the RNA Pol II promoter region (5' to a promoter, enhancer, boundary element, S/MAR) and the RNA Pol II polyA region (3' to a polyA sequence, eukaryotic transcriptional terminator sequence, boundary element, S/MAR). For example, in NTC9385R (FIG. 5) the spacer region is region between NheI site at 1663 and KpnI site at 460. In dual RNA Pol II transcription vectors, the eukaryotic sequences separated by the spacer will depend on the orientation of the two transcription elements. For example, with divergent or convergent RNA Pol II transcription units, the spacer region may separate two polyA sequences or two enhancers respectively. In RNA Pol II, RNA Pol III dual expression vectors, the spacer region may separate an RNA Pol II enhancer and a RNA Pol III promoter. The spacer region may encode bacterial or eukaryotic selectable markers, bacterial transcription terminators, eukaryotic transcription terminators, boundary elements, S/MARs, RNA Pol I or RNA Pol III expressed sequences or other functionalities ssi: Single stranded initiation sequences SV40 enhancer: Region containing the 72 bp and optionally the 21 bp repeats target antigen: Immunogenic protein or peptide epitope, or combination of proteins and epitopes, against which an immune response can be mounted. Target antigens may by derived from a pathogen for infectious disease applications, or derived from a host organism for applications such as cancer, allergy, or autoimmune diseases. Target antigens are well defined in the art. Some examples are disclosed in Williams, Supra, 2008 and are included herein by reference TE buffer: A solution containing approximately 10 mM Tris pH 8 and 1 mM EDTA Transcription terminator: Bacterial: A DNA sequence that marks the end of a gene or operon for transcription. This may be an intrinsic transcription terminator or a Rho-dependent transcriptional terminator. For an intrinsic terminator, such as the trpA terminator, a hairpin structure forms within the transcript that disrupts the mRNA-DNA-RNA polymerase ternary complex. Alternatively, Rho-dependent transcriptional terminators require Rho factor, an RNA helicase protein complex, to disrupt the nascent mRNA-DNA-RNA polymerase ternary complex. Eukaryotic: PolyA sites are not 'terminators', instead internal cleavage at PolyA sites leaves an uncapped 5' end on the 3'UTR RNA for nuclease digestion. Nuclease catches up to RNA Pol II and causes termination. Termination can be promoted within a short region of the poly A site by introduction of RNA Pol II pause sites (eukaryotic transcription terminator). Pausing of RNA Pol II allows the nuclease introduced into the 3' UTR mRNA after PolyA cleavage to catch up to RNA Pol II at the pause site. A nonlimiting list of eukaryotic transcription terminators know in the art include the C2x4 terminator (Ashfield R, Patel A J, Bossone S A, Brown H, Campbell R D, Marcu K B, Proudfoot N J. 1994. *EMBO J* 13:5656) and the gastrin terminator (Sato K, Ito R, Baek K H, Agarwal K, 1986. *Mol. Cell. Biol.* 6:1032). Terminator element may stabilize mRNA by enhancing proper 3'-end processing of mRNA (Kim D, Kim J D, Baek K, Yoon Y, Yoon J. 2003. *Biotechnol Prog* 19:1620)

Transgene: Target antigen or protein or RNA gene that is cloned into a vector ts: Temperature sensitive μg: microgram μl: microliter UTR: Untranslated region of a mRNA (5' or 3' to the coding region)

VARNA: Adenoviral virus associated RNA, including VARNAI (VAI or VA1) and or VARNAII (VAII or VA2) from any Adenovirus serotype, for example, serotype 2, serotype 5 or hybrids thereof VARNAI: Adenoviral virus associated RNAI, also referred to as VAI, or VA1, from any Adenovirus serotype, for example, serotype 2, serotype 5 or hybrids thereof Vector: A gene delivery vehicle, including viral (e.g. alphavirus, poxvirus, lentivirus, retrovirus, adenovirus, adenovirus related virus, etc) and nonviral (e.g. plasmid, midge, transcriptionally active PCR fragment, minicircles, bacteriophage, etc) vectors. These are well known in the art and are included herein by reference Vector backbone: Eukaryotic region and bacterial region of a vector, without the transgene or target antigen coding region

DETAILED DESCRIPTION OF THE PREFERRED EMBODIMENTS

The invention relates generally to plasmid DNA compositions and methods to improve plasmid expression and plasmid production. The invention can be practiced to improve expression of vectors such as eukaryotic expression plasmids useful for gene therapy, genetic immunization and or interferon therapy. The invention can be practiced to improve the copy number of vectors such as eukaryotic expression plasmids useful for gene therapy, genetic immunization and or interferon therapy. It is to be understood that all references cited herein are incorporated by reference in their entirety.

According to one preferred embodiment, the present invention provides for method of increasing in vivo expression of transgene from covalently closed super-coiled plasmid DNA, which comprises modifying the plasmid DNA to replace the pMB1, ColE1 or pBR322 derived replication origin and selectable marker with a replication origin selected from the group consisting of an $P_{min}$ minimal pUC replication origin, ColE2-P9 replication origin, ColE2 related replication origin, and R6K replication origin and a RNA selectable marker; transforming the modified plasmid DNA into a Rep protein producing bacterial cell line rendered competent for transformation; and isolating the resultant transformed bacterial cells. The modified plasmid produced from these cells has increased transgene expression in the target organism.

In one preferred embodiment, the spacer region encoded pMB1, ColE1 or pBR322 derived replication origin is replaced with a CpG free ColE2 origin. In another preferred embodiment, a primosome assembly site is incorporated into a ColE2 plasmid DNA backbone to improve plasmid copy number. In yet another preferred embodiment, the pMB1, ColE1 or pBR322 derived replication origin is replaced with a CpG free R6K origin.

The methods of plasmid modification of the present invention have been surprisingly found to improve plasmid expression in the target organism. Increased expression vectors may find application to improve the magnitude of DNA vaccination mediated antigen reactive B or T cell responses for preventative or therapeutic vaccination, increase RNA and or protein transgene levels to improve gene replacement therapy or gene knockdown therapy, increase plasmid based expression levels of DNA vector expressed therapeutic antibodies that neutralize infectious diseases such as influenza, HIV, malaria, hepatitis C virus, tuberculosis, etc.

Plasmid encoded transgene expression in the target organism is preferably increased by employing specific constructs or compositions incorporated in a vector. According to one preferred embodiment, the present invention provides a composition for construction of a vector, comprising a ColE2 origin with at least 90% sequence identity to the sequences set forth as SEQ ID NO: 4, SEQ ID NO: 5, SEQ ID NO: 6, SEQ ID NO: 7, and a RNA selectable marker and a eukaryotic region, wherein the ColE2 origin is operably linked to the RNA selectable marker and eukaryotic region. It has been surprisingly found that this ColE2 origin-RNA selectable marker improves plasmid encoded transgene expression in the target organism. According to another preferred embodiment, the resultant vector of the invention has at least 95% sequence identity to a sequence selected from the group consisting of: SEQ ID NO: 8, SEQ ID NO: 9.

According to another preferred embodiment, the present invention provides a composition for construction of a vector, comprising an R6K origin with at least 90% sequence identity to the sequences set forth as SEQ ID NO: 1, SEQ ID NO: 22, and a RNA selectable marker and a eukaryotic region, wherein the R6K origin is operably linked to the RNA selectable marker and eukaryotic region. It has been surprisingly found that this R6K origin-RNA selectable marker improves plasmid encoded transgene expression in the target organism. According to another preferred embodiment, the resultant vector of the invention has at least 95% sequence identity to a sequence selected from the group consisting of: SEQ ID NO: 2, SEQ ID NO: 3, SEQ ID NO: 39, SEQ ID NO: 40, SEQ ID NO: 41.

As used herein, the term "sequence identity" refers to the degree of identity between any given query sequence, e.g., SEQ ID NO: 2, and a subject sequence. A subject sequence may, for example, have at least 90 percent, at least 95 percent, or at least 99 percent sequence identity to a given query sequence. To determine percent sequence identity, a query sequence (e.g., a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., 2003 *Nucleic Acids Res.*, 31:3497-500. In a preferred method, the sequence alignment program (e.g., ClustalW) calculates the best match between a query and one or more subject sequences, and aligns them so that identities, similarities, and differences can be determined Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

According to another preferred embodiment, the present invention provides methods and compositions for production of a Rep protein dependent plasmid vector. Production cell lines providing improved heat inducible $P_L$ promoter expression of a Rep protein integrated into the genome and expressed from the heat inducible $P_L$ promoter incorporating the OL1-G deletion (SEQ ID NO: 11), or the heat inducible $P_L$ promoter incorporating the OL1-G to T substitution (SEQ ID NO: 12). It has been surprisingly found that these promoter modifications improves Rep protein dependent plasmid vector copy number in shake flask and fermentation cultures.

Turning now to the drawings, FIG. 1. shows an annotated map of the antibiotic free NTC8685 pUC origin expression vector with the locations of the pUC origin, PAS-BH primosomal assembly site, SV40 enhancer and other key elements indicated. The replication origin (PAS-BH and pUC origin) is from the AgeI (230) site to the DraIII (1548) site (1318 bp total). The antibiotic free RNA-OUT selection marker is between the DraIII (1548) and KpnI (1695) sites (147 bp total). The spacer region encoded bacterial region (replication and selection) of this vector is 1465 bp.

Figure 2:
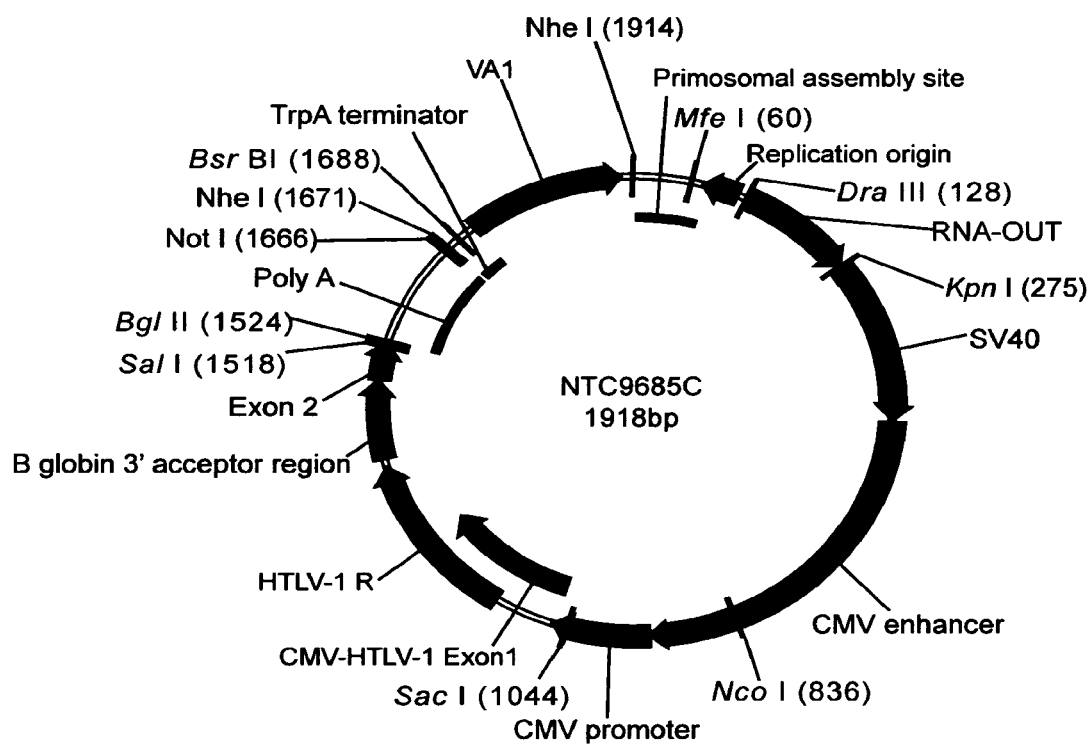
FIG. 2 depicts the NTC9685C ColE2 origin expression vector.

FIG. 2 shows an annotated map of the antibiotic-free NTC9685C ColE2 origin expression vector with the locations of the primosomal assembly site, ColE2 Replication origin (Replication origin) and other key elements indicated. The spacer region encoded bacterial region (replication and selection) of this vector is 281 bp [NheI site-ssiA-ColE2 Origin (+7)-RNA-OUT-KpnI site] (SEQ ID NO:20).

Figure 3:
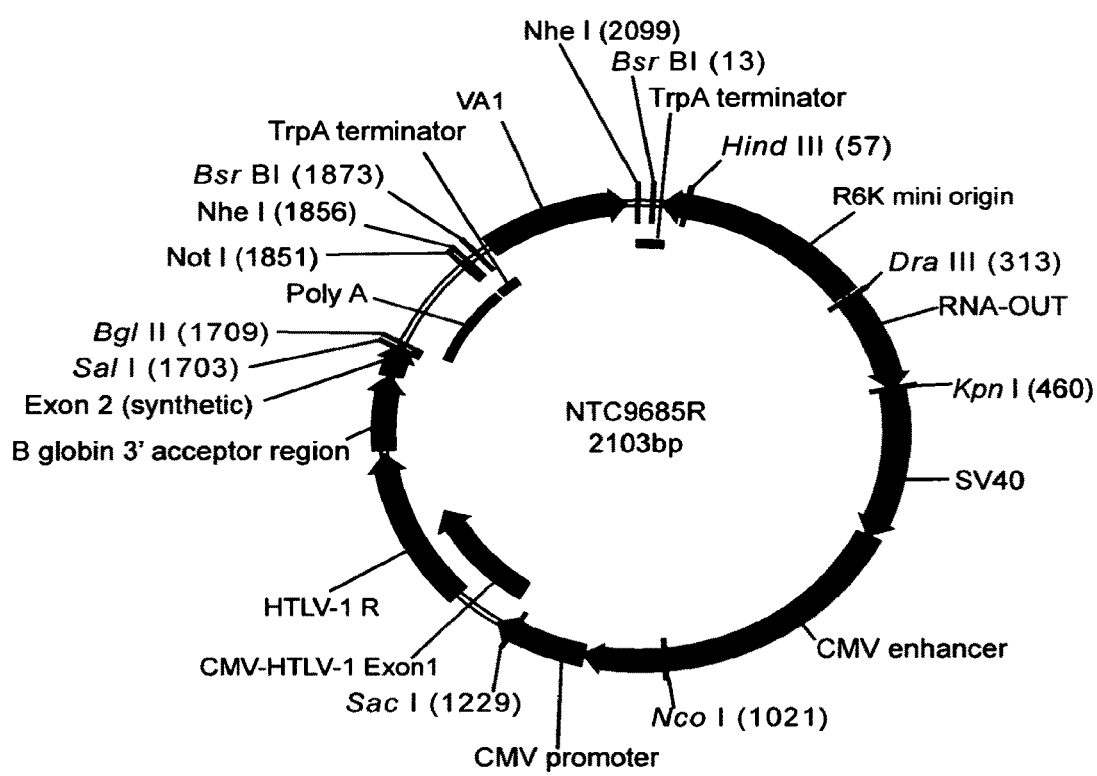
FIG. 3 depicts the NTC9685R R6K origin expression vector.

FIG. 3 shows an annotated map of the antibiotic-free NTC9685R R6K origin expression vector with the locations of the primosomal assembly site, R6K Replication origin (R6K mini-origin) and other key elements indicated. The spacer region encoded bacterial region (replication and selection) of this vector is 466 bp [NheI site-trpA terminator-R6K Origin-RNA-OUT-KpnI site] (SEQ ID NO:19).

Figure 4:
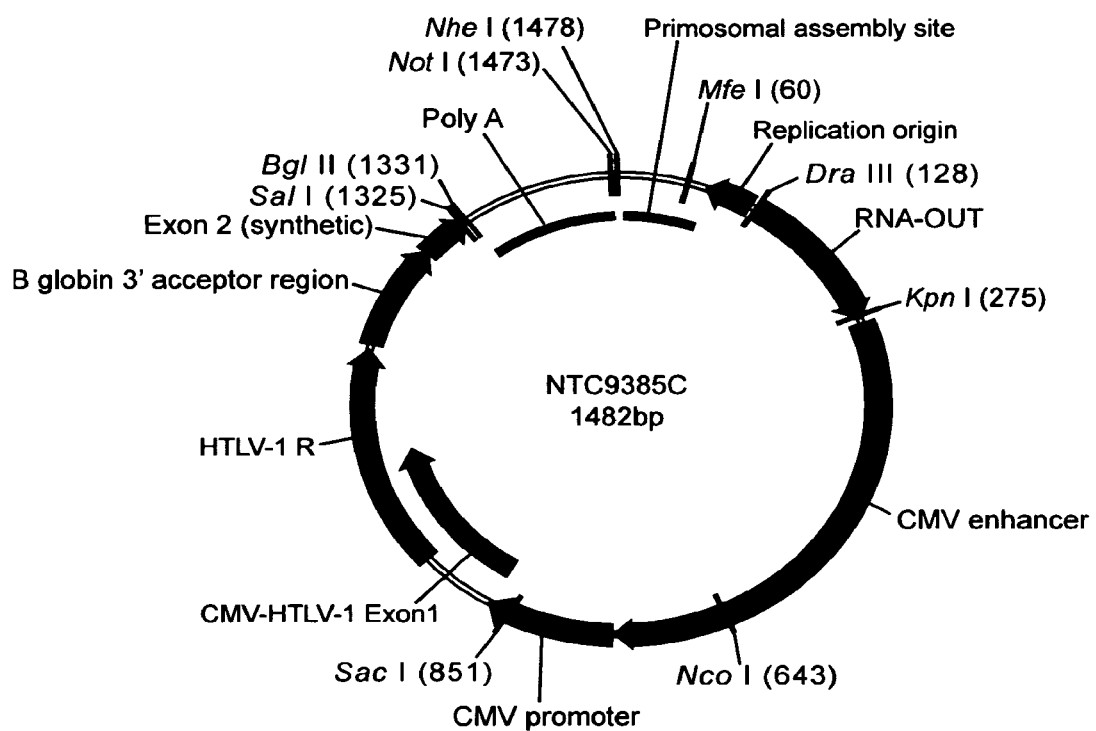
FIG. 4 depicts the NTC9385C ColE2 origin expression vector.

FIG. 4 shows an annotated map of the antibiotic-free NTC9385C ColE2 origin expression vector with the locations of the primosomal assembly site, ColE2 Replication origin (Replication origin) and other key elements indicated. The spacer region encoded bacterial region (replication and selection) of this vector is 281 bp [NheI site-ssiA-ColE2 Origin (+7)-RNA-OUT-KpnI site] (SEQ ID NO:20). This vector differs from NTC9685C in that the VA1 RNA and SV40 enhancer are not present.

Figure 5:
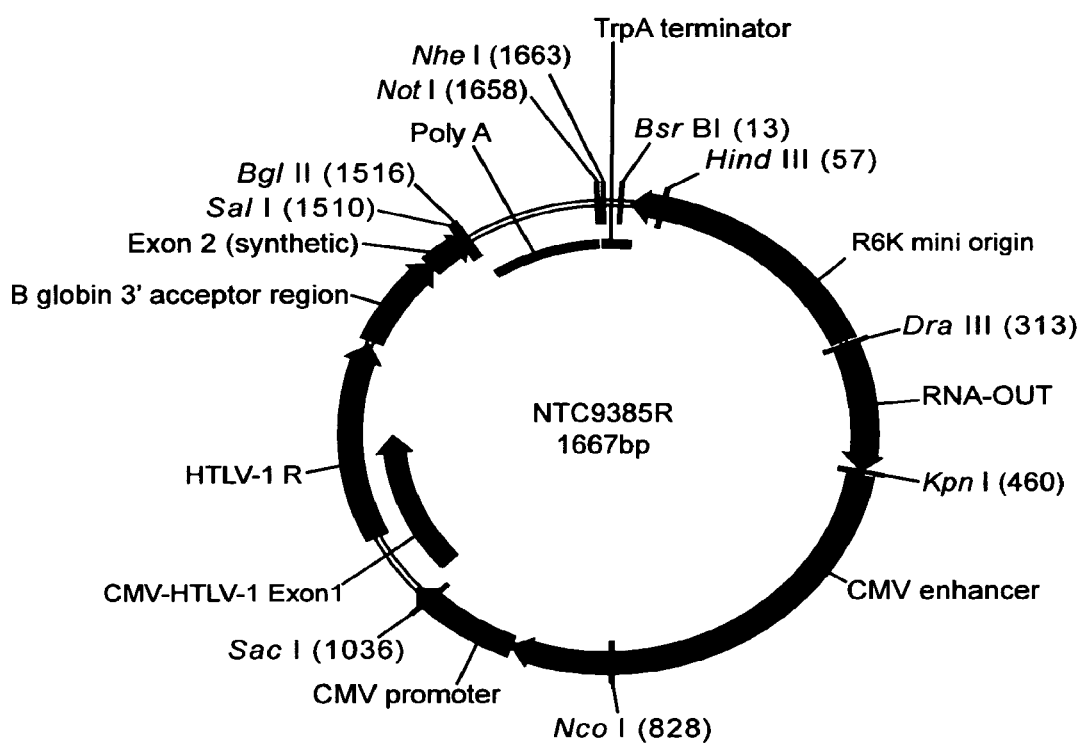
FIG. 5 depicts the NTC9385R R6K origin expression vector.

FIG. 5 shows an annotated map of the antibiotic-free NTC9385R R6K origin expression vector with the locations of the primosomal assembly site, R6K Replication origin (R6K mini-origin) and other key elements indicated. The spacer region encoded bacterial region (replication and selection) of this vector is 466 bp [NheI site-trpA terminator-R6K Origin-RNA-OUT-KpnI site] (SEQ ID NO:19). This vector differs from NTC9685R in that the VA1 RNA and SV40 enhancer are not present.

Figure 6:
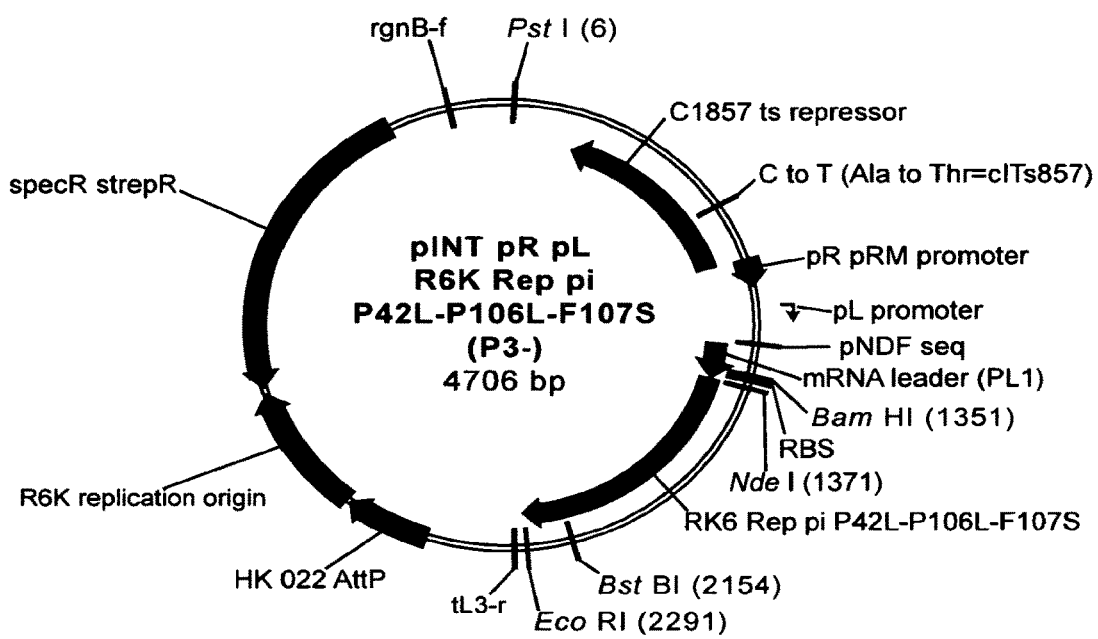
FIG. 6 depicts the pINT pR pL R6K Rep pi P42L-P106L-F107S (P3−) integration vector.

FIG. 6 shows an annotated map of the pINT pR pL R6K Rep pi P42L-P106L-F107S (P3−) integration vector; key features such as the cI857 is repressor, $P_L$ promoter, R6K Rep protein, HK022 phage attachment site for site specific integration into the *E. coli* genome, R6K replication origin and spectinomycin/streptomycin resistance marker (SpecR StrepR) are shown.

FIG. 7 show an annotated sequence of the $P_L$ promoter with locations of the $P_L$ promoter OL1, OL2 and OL3 repressor binding sites, −10 and −35 promoter elements for $P_L1$ and $P_L2$ promoters. The OL1 mutations OL1-G and OL1-G to T alterations are shown.

Figure 8:
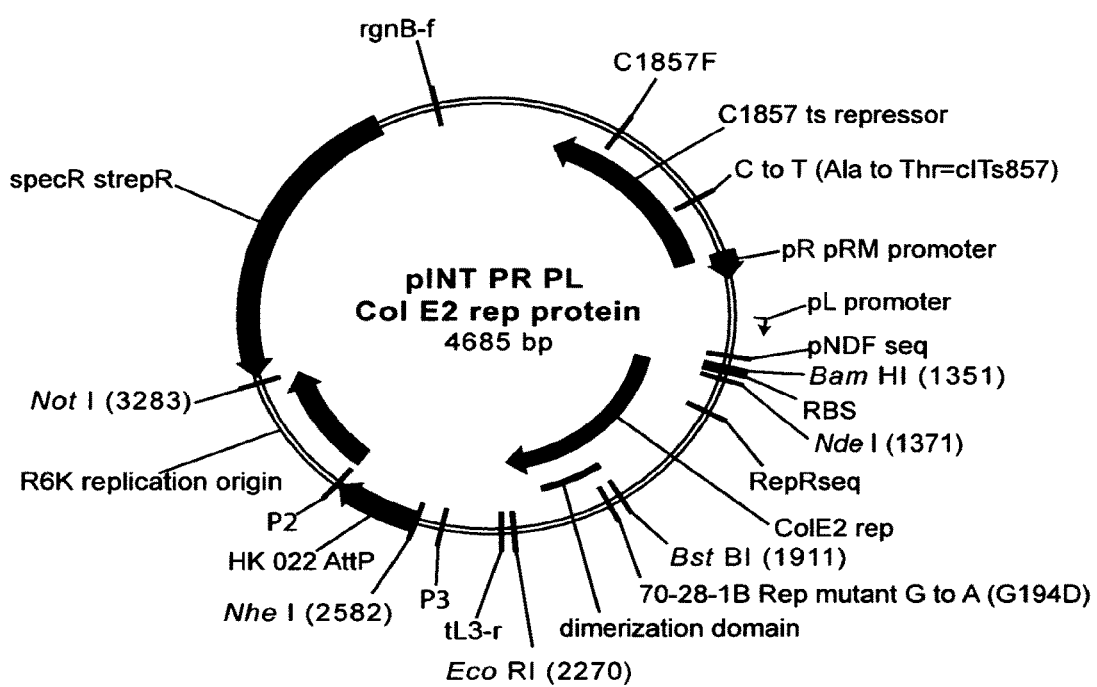
FIG. 8 depicts the pINT pR pL ColE2 Rep protein integration vector.

FIG. 8 shows an annotated map of the pINT pR pL ColE2 Rep protein integration vector; key features such as the cI857 is repressor, $P_L$ promoter, ColE2 Rep protein, HK022 phage attachment site for site specific integration into the *E. coli* genome, R6K replication origin and spectinomycin/streptomycin resistance marker (SpecR StrepR) are shown.

Figure 9:
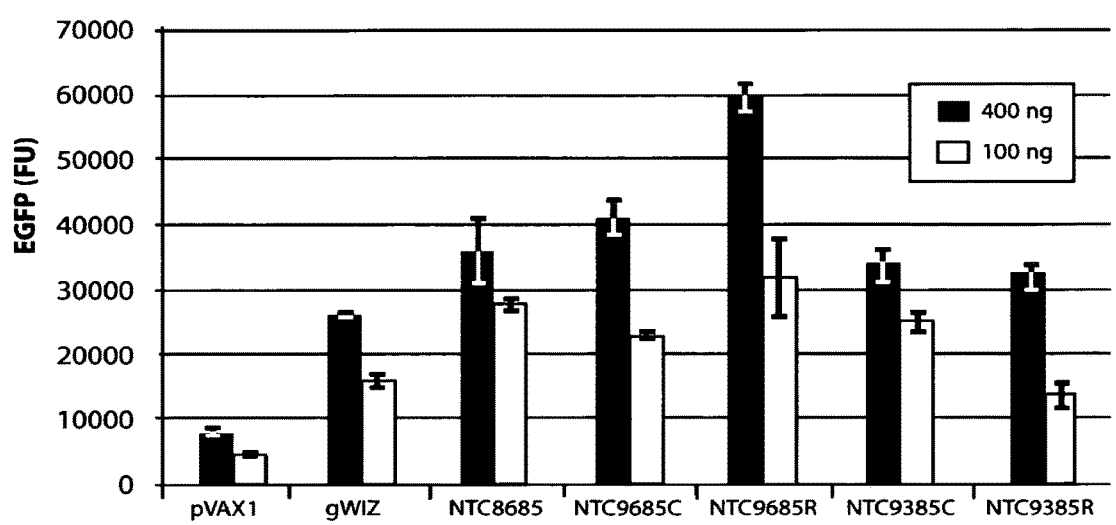
FIG. 9 shows Nanoplasmid expression in vitro after lipofectamine transfection of HEK293 cell line.

FIG. 9 shows Nanoplasmid expression in vitro after lipofectamine transfection of HEK293 cell line of various EGFP transgene encoding vectors.

Figure 10:
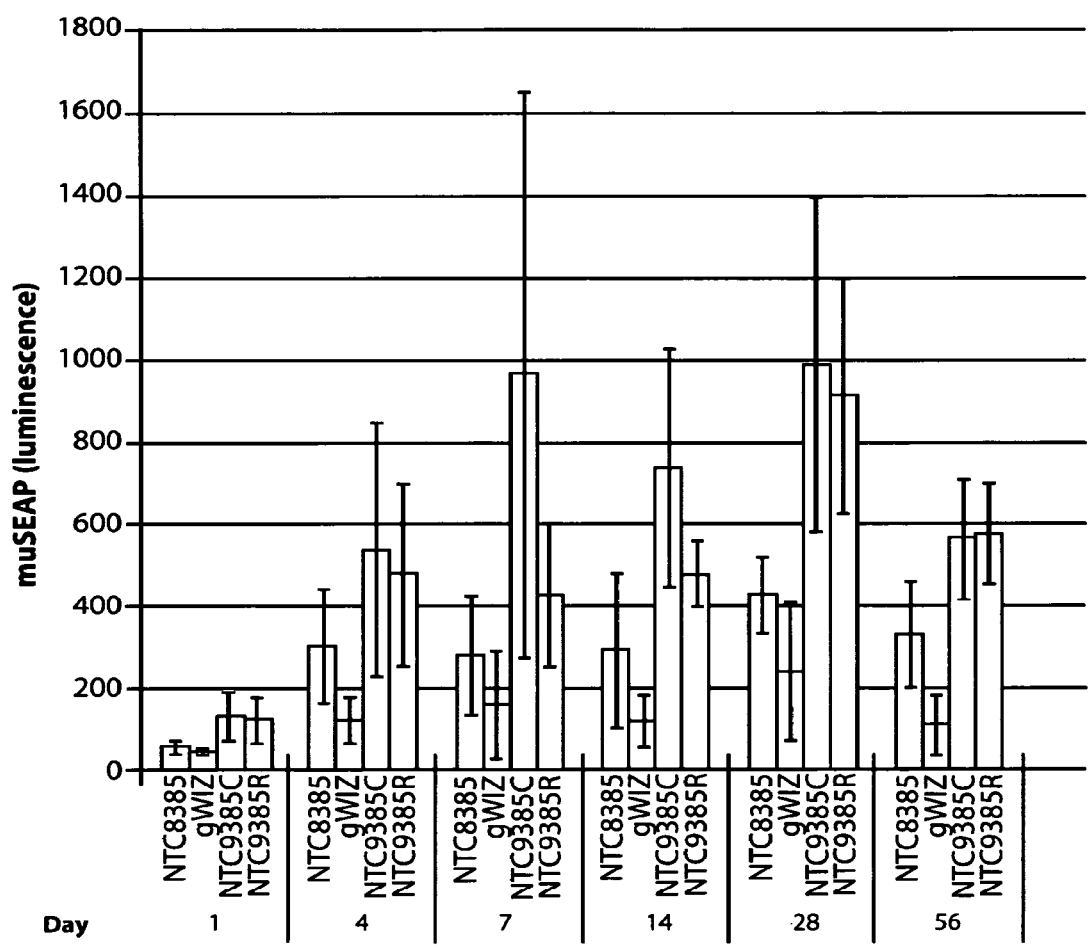
FIG. 10 shows Nanoplasmid expression in vivo after intramuscular injection with EP.

FIG. 10 shows Nanoplasmid expression in vivo after intramuscular injection with EP of various muSEAP transgene encoding vectors.

Figure 11:
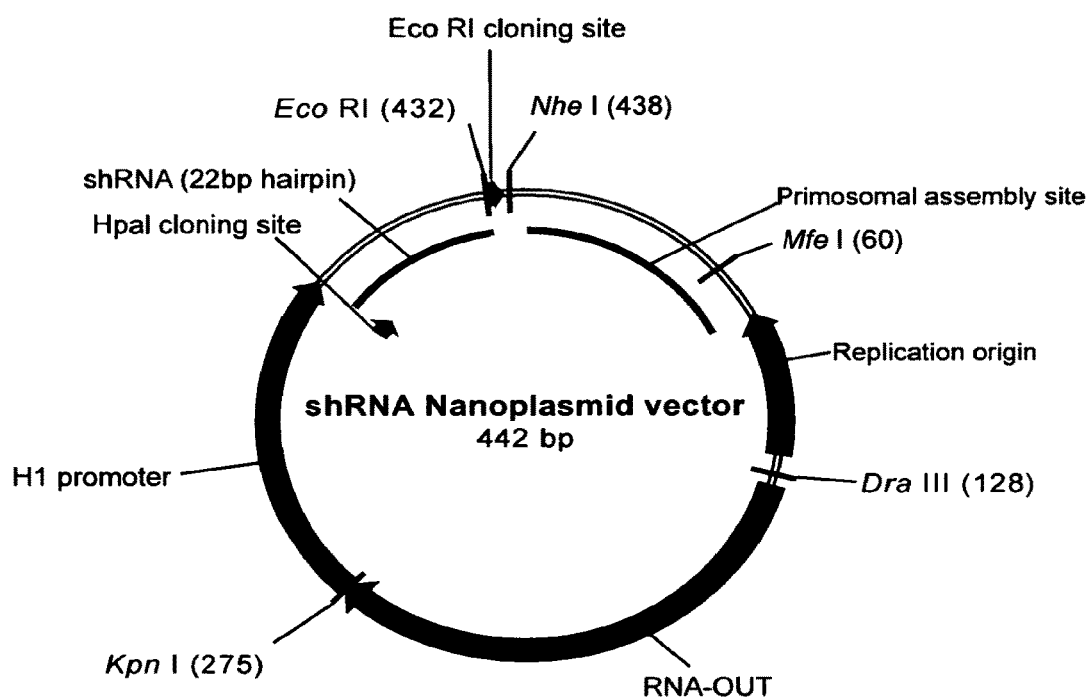
FIG. 11 depicts a ColE2 origin Nanoplasmid shRNA expression vector.

FIG. 11 shows a ColE2 origin Nanoplasmid shRNA expression vector. In this vector, a 22 bp shRNA is expressed from the RNA Polymerase III H1 promoter, with a TTTTTT terminator. The bacterial region is the NTC9385C and NTC9685C Bacterial region (SEQ ID NO:20).

Figure 12:
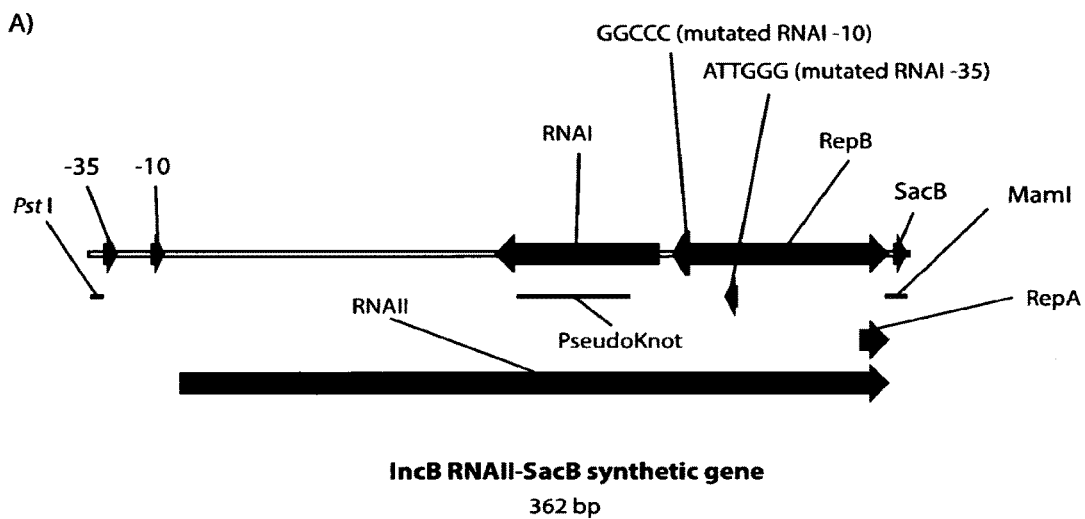
FIG. 12 depicts an IncB RNAI based RNA selectable marker.
Figure 12:
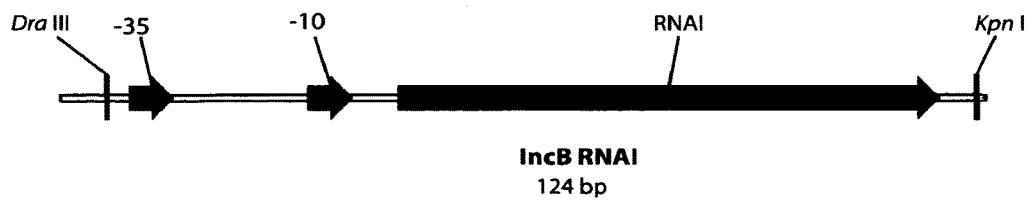

FIG. 12 shows an IncB RNAI based RNA selection marker. A) Genomically expressed target of IncB RNAI RNA selection marker (SEQ ID NO: 35). Plasmid expressed RNAI binding to the pseudoknot in the complementary genomically expressed RNAII target prevents translation of the downstream SacB gene, conferring sucrose resistance. The RNAI −10 and −35 promoter elements are mutated to prevent RNAI expression. B) Structure of plasmid expressed IncB RNAI RNA selection marker (SEQ ID NO: 34) encoding the IncB RNAI antisense repressor (SEQ ID NO: 33).

The invention also relates to compositions and methods for producing high expression level plasmids. The present invention provides sequences that, when introduced into a vector backbone, increase plasmid expression.

The surprising observation that a ColE2 replication origin-RNA selection marker or R6K replication origin-RNA selection marker can be utilized as a plasmid expression enhancer is disclosed.

As described herein, plasmid expression is increased by replacement of the pMB1, ColE1 or pBR322 derived origin-selection marker bacterial region with an R6K origin-RNA selection marker in the plasmid backbone. In yet another preferred embodiment, the R6K origin is CpG free. In yet another preferred embodiment, the R6K origin is included with an RNA-OUT selection marker. In yet another preferred embodiment, the R6K origin is included with an pMB1 RNAI selection marker. In yet another preferred embodiment, the R6K origin is included with an IncB RNAI selection marker.

In yet another preferred embodiment, plasmid expression is increased by replacement of the pMB1, ColE1 or pBR322 derived origin-selection marker bacterial region with a ColE2 origin-RNA selection marker in the plasmid backbone. In yet another preferred embodiment, the ColE2 origin is CpG free. In yet another preferred embodiment, the ColE2 origin is included with an RNA-OUT selection marker. In yet another preferred embodiment, the ColE2 origin is included with an pMB1 RNAI selection marker. In yet another preferred embodiment, the ColE2 origin is included with an IncB RNAI selection marker. In yet another preferred embodiment, the ColE2 origin is included with a primosome assembly site.

In yet another preferred embodiment, plasmid expression is increased by replacement of the pMB1, ColE1 or pBR322 derived origin-selection marker with a $P_{min}$ minimal pUC, ColE2 or a R6K origin in the plasmid backbone spacer region and an RNA selection marker in an intron. In yet another preferred embodiment, the R6K or ColE2 origin is CpG free. In yet another preferred embodiment, the RNA selection marker is the RNA-OUT selection marker. In yet another preferred embodiment, the RNA selection marker is the pMB1 RNAI selection marker. In yet another preferred embodiment, the RNA selection marker is the IncB RNAI selection marker.

EXAMPLES

The methods of the invention are further illustrated by the following examples. These are provided by way of illustration and are not intended in any way to limit the scope of the invention.

Example 1: Heat Inducible R6K Replication Origin Plasmid Production

Fermentation:

Fermentations were performed using proprietary fed-batch media (NTC3019, HyperGRO media) in New Brunswick BioFlo 110 bioreactors as described (Carnes and Williams, Supra, 2011). The seed cultures were started from glycerol stocks or colonies and streaked onto LB medium agar plates containing 6% sucrose. The plates were grown at 30-32° C.; cells were resuspended in media, and used to provide approximately 0.1% inoculums for the fermentations that contained 0.5% sucrose to select for RNA-OUT plasmids.

Antibiotic-free RNA-OUT plasmid fermentations were performed in *E. coli* strain XL1Blue [recA1 endA1 gyrA96 thi-1 hsdR17 supE44 relA1 lac [F' proAB lacIqZΔM15 Tn10 (Tet$^r$)] (Stratagene, La Jolla, Calif.)] or GT115 [F—mcrA Δ(mrr-hsdRMS-mcrBC) φ801 acZΔM15 ΔlacX74 recA1 rspL (StrA) endA1 Δdcm uidA(ΔMluI)::pir-116 ΔsbcC-sbcD (Invivogen, San Diego)] strains containing chromosomally integrated pCAH63-CAT RNA-IN-SacB (P5/6 6/6) at the phage lambda integration site as disclosed in Williams, J A Supra, 2008. SacB (*Bacillus subtilis* levansucrase) is a counterselectable marker which is lethal to *E. coli* cells in the presence of sucrose. Translation of SacB from the RNA-IN-SacB transcript is inhibited by plasmid encoded RNA-OUT. This facilitates plasmid selection in the presence of sucrose, by inhibition of SacB mediated lethality.

Analytical Methods:

Culture samples were taken at key points and at regular intervals during all fermentations. Samples were analyzed immediately for biomass ($OD_{600}$) and for plasmid yield. Plasmid yield was determined by quantification of plasmid obtained from Qiagen Spin Miniprep Kit preparations as described (Carnes and Williams, Supra, 2011). Briefly, cells were alkaline lysed, clarified, plasmid was column purified, and eluted prior to quantification. Agarose gel electrophoresis analysis (AGE) was performed on 0.8-1% Tris/acetate/EDTA (TAE) gels as described in Carnes and Williams J A, Supra, 2011.

R6K Background:

The R6K gamma plasmid replication origin requires a single plasmid replication protein π that binds as a monomer to multiple repeated 'iteron' sites (seven core repeats containing TGAGNG consensus) and as a dimer to repressive sites [TGAGNG (dimer repress) as well as to iterons with reduced affinity]. Various host factors are used including IHF, DnaA, and primosomal assembly proteins DnaB, DnaC, DnaG (Abhyankar et al 2003 *J Biol Chem* 278: 45476-45484). The R6K core origin contains binding sites for DnaA and IHF that affect plasmid replication (π, IHF and DnaA interact to initiate replication).

Different versions of the R6K gamma replication origin have been utilized in various eukaryotic expression vectors, for example pCOR vectors (Soubrier et al 1999, *Gene Therapy* 6:1482) and a CpG free version in pCpGfree vectors (Invivogen, San Diego Calif.), and pGM169 (University of Oxford). Incorporation of the R6K replication origin does not improve expression levels compared to an optimized pUC origin vector (Soubrier et al Supra, 1999). However, use of a conditional replication origin such as R6K gamma that requires a specialized cell line for propagation adds a safety margin since the vector will not replicate if transferred to a patients endogenous flora.

A highly minimalized R6K gamma derived replication origin that contains core sequences required for replication (including the DnaA box and stb 1-3 sites; Wu et al, 1995. *J Bacteriol*. 177: 6338-6345), but with the upstream π dimer repressor binding sites and downstream π promoter deleted (by removing one copy of the iterons, as with pCpG; see map below) was designed (SEQ ID NO:1) and NTC9685R and NTC9385R expression vectors incorporating it constructed (see Example 3).

Typical R6K production strains incorporate the π protein derivative PIR116 that contains a P106L substitution that increases copy number (by reducing π dimerization; π monomers activate while π dimers repress). Fermentation results with pCOR (Soubrier et al., Supra, 1999) and pCpG plasmids (Hebel H L, Cai Y, Davies L A, Hyde S C, Pringle I A, Gill D R. 2008. *Mol Ther* 16: S110) were low, around 100 mg/L in PIR116 cell lines.

As expected, fermentation yields of the R6K expression vector NTC9685R-EGFP in R6K plasmid production cell line NTC641642 (GT115-SacB; GT115 modified for RNA-OUT AF vector selection by insertion of pCAH63-CAT RNA-IN-SacB (P5/6 6/6) into the genome. The GT115 genome encoded endogenous π gene P3 promoter constitutively expresses R6K replication protein π containing the pir-116 mutation; Metcalf et al, 1994; Gene 138; 1-7) were low (Table 1). Mutagenesis of the pir-116 replication protein and selection for increased copy number has been used to make new production strains. For example, the TEX2pir42 strain contains a combination of P106L and P42L. The P42L mutation interferes with DNA looping replication repression. The TEX2pir42 cell line improved copy number and fermentation yields with pCOR plasmids with reported yields of 205 mg/L (Soubrier F. 2004. World Patent Application WO2004033664). Methods to improve R6K origin yields are needed.

Other combinations of π copy number mutants have been shown to improve copy number. This includes 'P42L and P113S' and 'P42L, P106L and F107S' (Abhyankar et al 2004. *J Biol Chem* 279:6711-6719).

Two cell lines using the endogenous π gene P3 promoter to express π mutants 'P42L and P113S' (SEQ ID NO:13) (NTC640722 cell line) and 'P42L, P106L and F107S' (SEQ ID NO:14) were constructed and tested for copy number improvement with NTC9685R-EGFP. Two additional cell lines using the $P_L$ promoter in addition to the endogenous π gene P3 promoter to express π mutants 'P42L and P113S' (NTC641981 cell line) and 'P42L, P106L and F107S' (NTC641053 cell line) were made and tested for copy number improvement with NTC9685R-EGFP. R6K production cell lines were made in XL1-Blue SacB (XL1-Blue attλ:P5/6 6/6-RNAIN-SacB, CmR).

These cell lines were constructed as follows. The R6K replication proteins π were cloned into the pINT pR pL integration vectors as described in Luke et al Supra, 2011 and included herein by reference. Constructed R6K Rep protein vectors were integrated into the genome at the HK022 phage attachment site as described in Luke et al, Supra, 2011. Briefly the pINT pINT pR pL R6K Rep vectors were amplified by PCR to delete the R6K replication origin, ligated to form a circle, and integrated into the HK022 attachment site using the pAH69 helper plasmid as described.

The results (Table 1) demonstrated that constitutive expression of 'P42L and P113S' or 'P42L, P106L and F107S' resulted in much higher levels of NTC9685R-EGFP than the NTC641642 encoded P106L Rep protein. However, constitutive expression from P3 resulted in low overall biomass and plasmid multimerization with P42L, P106L and F107S (RF306, RF314), due to high plasmid levels and resultant metabolic burden during the growth phase.

TABLE 1

2.6 kb NTC9685R-EGFP R6K Nanoplasmid fermentation yields in R6K rep cell lines

| Ferm # | Cell line | Rep Gene | Promoter | Growth phase temp (C.) | Growth spec yield[a] | Induced phase temp (C.) | Induced spec yield[a] | Final $OD_{600}$ | Final plasmid yield (mg/L) | Plasmid multimerization |
|---|---|---|---|---|---|---|---|---|---|---|
| RF310 | NTC641642 | P106L | Const P3 | 37 | 1.1 | NA, 37 | 1.2 | 43 | 53 | |
| RF323 | NTC641642 | P106L | Const P3 | 37 | ND | NA, 37 | 0.9 | 54 | 49 | Monomer |
| RF305 | NTC640722 | P42L-P113S | Const P3 | 30 | 3.4 | 37 | 3.6 | 96 | 345 | Monomer |

TABLE 1-continued 2.6 kb NTC9685R-EGFP R6K Nanoplasmid fermentation yields in R6K rep cell lines

| Ferm # | Cell line | Rep Gene | Promoter | Growth phase temp (C.) | Growth spec yield[a] | Induced phase temp (C.) | Induced spec yield[a] | Final OD$_{600}$ | Final plasmid yield (mg/L) | Plasmid multimerization |
|---|---|---|---|---|---|---|---|---|---|---|
| RF321 | NTC641981 | P42L-P113S | pR PL & P3 | 32 | 4.4-5.0 | 42 | 2.8 | 93 | 259 | Monomer[b] |
| RF306 | NTC641053 | P42L-P106L-F107S | pR PL & P3 | 30 | 3.1 | 37 | 6.6 | 86 | 567 | Multimer |
| RF314 | NTC641053 | P42L-P106L-F107S | pR PL & P3 | 32 | 2.6-4.7 | 42 | 7.1 | 79 | 558 | Multimer |
| RF351 | NTC661135 | P42L-P106L-F107S | pR PL only | 32 | 0.4 | 42 | 1.45 | 88 | 128 | Monomer |
| RF326 | NTC661135-MUT | P42L-P106L-F107S | pR PL OL1 G | 32 | 0.64 | 42 | 6.7 | 81 | 545 | Monomer |
| RF358 | NTC711055 | P42L-P106L-F107S | pR PL OL1 G | 32 | 1 | 42 | 5.9 | 118 | 690 | Monomer |
| RF359 | NTC711231 | P42L-P106L-F107S | pR PL OL1 G to T | 30 | 1.8 | 42 | 8.5 | 82 | 695 | Monomer |

NTC640721 = NTC5402-P42L-P106L-F107S
NTC640722 = NTC5402-P42L-P113S
NTC641053 = NTC5402-pR pL P42L-P106L-F107S
NTC641642 = GT115-SacB (relA+) pir116 = P106L
NTC641981 = NTC5402-pR pL P42L-P113S
NTC661135 = NTC54208-pR pL P42L-P106L-F107S (P3-)
NTC661135-MUT = NTG54208-pR pL (OL1-G) P42L-P106L-F107S (P3-)
NTC661134 = NTC5402-pR pL P42L-P113S (P3-)
NTC711055 = NTC54208-pR pL (OL1-G) P42L-P106L-F107S (P3-)
NTC711231 = NTC54208-pR pL (OL1-G to T) P42L-P106L-F107S (P3-)
ND = Not determined
NA = Not applicable
[a]Specific Yield = mg plasmid/L/OD600
[b]Some dimer present
NTC5402 = XL1Blue, SacB
NTC54208 = XL1Blue, SacB, dcm- Heat inducible versions were then made by deletion of the P3 promoter to determine if $P_L$ promoter mediated replication protein induction in a temperature shift improved R6K plasmid production yields and quality by reduction of plasmid copy number and metabolic burden during the reduced temperature growth phase. A strain encoding a deletion of the P3 promoter expressing P42L, P106L and F107S (NTC661135, incorporating a single copy of the pINT pR pL R6K Rep pi P42L-P106L-F107S (P3-) integration vector; FIG. 6, SEQ ID NO:17) constructed as described above dramatically reduced copy number during the reduced temperature growth phase with copy number induction after temperature upshift (Table 1; RF351). However, the yield (128 mg/L) was overall lower than with the P3 promoter (567, 558 mg/L).

However, excellent results were obtained after fermentation with a second NTC661135 cell line (RF326) in which plasmid copy number was increased 10 fold by temperature shifting, resulting in excellent final plasmid yields of 545 mg/L. PCR amplification and sequencing of the P42L, P106L and F107S expression cassette from the RF326 cell line (NTC661135-MUT) and the RF351 cell line (NTC661135) demonstrated that NTC661135-MUT contained a mutation in the OL1 lambda repressor binding site in the $P_L$ promoter (FIG. 7; OL1-G this is a single base deletion that also reduces the distance between the $P_L$1 promoter -35 and -10 boxes from optimal 17 bp to 16 bp).

This mutation was introduced into the pINT pR pL R6K Rep pi P42L-P106L-F107S (P3-) integration vector by PCR mutagenesis and a sequence verified clone incorporating the OL1-G mutation integrated into the genome (NTC711055) as described above. Fermentation evaluation of this cell line with the NTC9685R-EGFP plasmid (Table 1; RF358) demonstrated similar dramatic 6 fold heat inducible plasmid copy number induction, resulting in excellent final plasmid yields of 690 mg/L.

Repressor binding to OL1 is altered by mutations in OL1, such as OL1-G (FIG. 7; SEQ ID NO:11) and V2 (OL1-G to T; FIG. 7; SEQ ID NO:12; this is a G to T substitution that maintains the distance between the $P_L$ promoter -35 and -10 boxes at the optimal 17 bp; this is the V2 mutation described by Bailone and Galibert, Supra, 1980).

The OL1-G to T (V2) mutation was introduced into the pINT pR pL R6K Rep pi P42L-P106L-F107S (P3-) integration vector by PCR mutagenesis and a sequence verified clone incorporating the OL1-G mutation integrated into the genome as described above to create NTC711231. Fermentation evaluation of this cell line with the NTC9685R-EGFP plasmid (Table 1; RF359) demonstrated, similar to OL1G, a dramatic 5 fold heat inducible plasmid copy number induction, resulting in excellent final plasmid yields of 695 mg/L.

Cell lines incorporating the pINT pR pL R6K Rep pi P42L-P106L-F107S (P3-) integration vector containing either the wildtype $P_L$ promoter (NTC661135, SEQ ID NO:10), the OL1-G mutation (NTC711055, SEQ ID NO:11) or the OL1-G to T mutation (NTC711231, SEQ ID NO:12) were transformed with the NTC9385R-EGFP plasmid and yields in shake flask determined (Table 2). The results demonstrated the OL1-G and OL1-G to T mutations dramatically improve temperature inducible R6K plasmid yields in shake flask culture. Improved yield with two different R6K plasmids (NTC9385R, Table 2; NTC9685R, Table 1) in either LB shake flask media or HyperGRO fermentation media demonstrates improved temperature inducible R6K plasmid is generic, and is not plasmid or growth media specific. Thus the invention can be utilized with a plurality of R6K origin vectors, in various plasmid growth media described in the art and various temperature induction profiles.

Likewise the pINT pR pL R6K Rep plasmids can be integrated into alternative E. coli strains to create production hosts. Any strain that is acceptable for plasmid production, such as JM108, BL21, DH5, DH1, DH5α, GT115, GT116, DH10B, EC100, can be converted to a high yield temperature inducible R6K plasmid production host by integration of a pINT pR pL R6K Rep plasmid into the genome. The pR pL R6K Rep expression cassette may alternatively be removed from the pINT vector backbone and directly integrated into the chromosome, for example, using Red Gam recombination cloning (for example, using the methods described in Datsenko and Wanner 2000 *Proc Natl Acad Sci USA* 97:6640-6645). The pR pL R6K Rep expression cassette may alternatively be transferred to a different vector backbone, such as integration vectors that target different phage attachment sites, for example, those described by Haldimann and Wanner 2001, *J Bacteriol* 183:6384-6393.

TABLE 2

NTC9385R-EGFP LB media shake flask production yields in R6K production strains

| Cell Line | Rep Gene | Rep Gene Promoter | 30° C. Spec yield$^a$ | 32° C. Spec yield$^a$ | 37° C. Spec yield$^a$ |
|---|---|---|---|---|---|
| NTC661135 | P42L-P106L-F107S | $P_R P_L$ | 1.2 | 2.1 | 0.6 |
| NTC711055 | P42L-P106L-F107S | $P_R P_L$ (OL1-G) | 0.5 | 1.3 | 9.1 |
| NTC711231 | P42L-P106L-F107S | $P_R P_L$ (OL1-G to T) | 1.3 | 7.0 | 9.3 |

$^a$Specific yield = mg plasmid/L/OD$_{600}$

These results are surprising since the art teaches that $P_L$ promoter mutations in the OL1 binding site such as V2 (OL1-G to T) are constitutively active due to an inability of the lambda repressor to stop expression from the $P_L$ promoter (Bailone and Galibert, Supra, 1980). While not limiting the application of the invention, it is possible that the lambda repressor is able to repress the $P_L$ promoter through binding to the OL2 and OL3 sites (FIG. 7) when the $P_L$ promoter is integrated in the genome; the lambda repressor may not be able to bind multiple copies of the mutated $P_L$ promoter as in a phage infection.

The application of two independent OL1 mutations (OL1-G and OL1-G to T) to create cell lines for high yield R6K plasmid production demonstrates the general utility of $P_L$ promoters incorporating OL1 mutations to improve heat inducible chromosomal expression of a target protein. Any OL1 mutation is contemplated for use in the current invention. New OL1 mutations can be defined by standard methods known in the art, for example error prone mutagenesis of the OL1 region, with subsequent selection of beneficial OL1 mutations by screening for heat inducible target protein production. The target protein can be a Rep protein as described herein, or a fluorescent marker, or any target protein or RNA. Thus application of $P_L$ promoters incorporating OL1 mutations is contemplated generally as a platform for improved heat inducible chromosomal expression of any recombinant protein or RNA. This can be applied to improve heat inducible chromosomal expression of any recombinant protein or RNA using either shake flask (Table 2) or fermentation (Table 1) culture.

These cell lines may also be used to produce alternative R6K plasmids, such as CpGfree vectors, pCOR vectors, pGM169, etc. $P_L$ promoter vectors with the OL1 mutations may be used to improve expression of alternative target proteins or mRNAs from the genome.

These cell lines may also be used to produce alternative Rep protein dependent plasmids, such as ColE2-P9 replication origin plasmids (Examples 2 and 3), ColE2 related replication origin plasmids, etc. Numerous additional Rep protein dependent plasmids known in the art may also be produced using the cell lines of the invention. Many Rep protein dependent plasmids are described in del Solar et al Supra, 1998 which is included herein by reference.

Heat inducible target protein production may be further improved, by further mutating OL1-G and OL1-G to T or an alternative OL1 mutation to incorporate a mutation in the $P_L$-10 GATACT sequence to make it more closely match the consensus TATAAT (−35 is already consensus TTGACA (FIG. 7).

Alternative temperature sensitive (ts) lambda repressors (cI) may be substituted for the cIts857 mutation utilized in the pINT vectors. Multiple alternative ts lambda repressors have been defined (for example, see Lieb M. 1979 *J Virol* 32:162 incorporated herein by reference) or new ts lambda repressors may be isolated by screening for temperature sensitive cI function.

Alternative integration methods rather than the described pINT pR pL integration vectors may be utilized such as integration of the pR pL expression cassette into the genome at defined sites using Red Gam recombination cloning (for example, using the methods described in Datsenko and Wanner Supra, 2000).

Example 2: ColE2-P9 Replication Origin Plasmid Production

Similar to plasmid R6K, the ColE2 replication origin is separate from the replication protein, so the ColE2 replication origin theoretically may be utilized to construct Rep protein dependent plasmids. Here application of the ColE2 replication origin, using ColE2-P9 as an example, to produce ColE2 Rep protein dependent plasmids is demonstrated (Example 3).

ColE2 Background:

The ColE2 replication origin (for example, ColE2-P9) is highly conserved across the ColE2-related plasmid family (15 members are compared in Hiraga et al Supra, 1994, and 53 ColE2 related plasmid members including ColE3 are compared in Yagura et al Supra, 2006, both references are included herein by reference). Plasmids containing this origin are normally 10 copies/cell (low copy #). For application in gene therapy or DNA vaccination vectors, the copy number of ColE2 replication origin vectors needs to be improved dramatically.

Expression of the ColE2-P9 replication (Rep) protein is regulated by antisense RNA (RNAI). Copy number mutations have been identified that interfere with this regulation and raise the copy number to 40/cell (Takechi et al 1994 *Mol Gen Genet* 244:49-56).

pINT pR pL ColE2 Rep Protein Cell Line NTC641711:

The ColE2 Rep protein (SEQ ID NO:15) was expressed using the heat inducible pINT pR pL vector as described in Example 1. The ColE2 RNAI region was removed and replaced with an optimal kozak-ATG region. This modification deletes the RNAI −10 promoter box. The Rep internal RNAI −35 box (Yasueda et al 1994 *Mol Gen Genet* 244: 41-48) was mutagenized (from (opposite strand) TTGAAG to CTGAAG) to lower the consensus. A high copy mutation in the Rep coding region (C139T; Nagase et al 2008 *Plasmid* 59:36-44) was also incorporated.

These changes do not alter the Rep protein amino acid sequence (SEQ ID NO:15).

The ColE2 Rep gene was PCR amplified from CGSC Strain #8203 with following primers 15061101:
(SEQ ID NO: 26)
ggaacgggatccagaaggagatatacatatgagtgccgtacttcagcgct tcaggga 15061102:
(SEQ ID NO: 27)
ggaacggaattcttatcattttgcgagatctggatcacat The 920 bp PCR product was digested with BamHI/EcoRI and cloned into BamHI/EcoRI digested pINT pR pL BamHI/EcoRI (3766, polylinker). Recombinant clones were selected by restriction digestion and sequence verified. The map of the resultant pINT pR pL CoE2 Rep integration vector is shown in FIG. 8. The integration plasmid was integrated into NTC54208 (XL1Blue-sacB [dcm–]) to create cell line NTC641711 as described in Example 1.

A kanR ColE2-P9 replication origin fluorescent reporter plasmid (pDNAVACCUltra5-C2-P5/6,4/6-T7RBS EGFP) was constructed to select for copy number improving mutations. The 1067 bp pUC replication origin was removed from the kanR pDNAVACCUltra5-P5/6,4/6-T7RBS EGFP vector (the pDNAVACCUltra5-EGFP vector disclosed in Williams J A, 2006 World patent application WO06078979, modified to express the EGFP reporter in *E. coli* utilizing the weak constitutive P5/6,4/6 promoter disclosed in Lissemore J L, Jankowski J T, Thomas C B, Mascotti D P, deHaseth P L. 2000. *Biotechniques* 28: 82-89 and included herein by reference) by NheI-DraIII digestion, and replaced with a 132 bp ColE2-P9 replication origin (+7-ssiA; see below). Recombinant clones were recovered in cell line NTC641711 and the ColE2 origin confirmed by restriction digestion and sequence verification. This demonstrates that the ColE2-P9 Rep protein cell line NTC641711 can be used to select and propagate ColE2 replication origin containing plasmids.

ColE2 Rep Protein Mutagenesis, Selection of Copy Number Increasing Mutants

Background:

The ColE2 Rep protein binds as a monomer to the ColE2 replication origin. However, Rep protein exists mostly as a dimer in solution; Rep dimerization will limit the amount of active monomeric Rep which is hypothesized will maintain ColE2 plasmid at a low copy number (Han M, Aoki K, Yagura M, Itoh T. 2007. *Biochem Biophys Res Commun* 353:306). Copy number autoregulation by Rep protein dimerization is a common copy number control mechanism. Significantly, R6K Rep protein mutations such as P106L (PIR116) utilized in Example 1 that interfere with dimer formation dramatically increase copy number (Abhyankar et al Supra, 2004). It was hypothesized that ColE2 plasmid copy number can also be increased with a dimerization deficient Rep mutation.

Mutagenesis:

ColE2 Rep protein functional domains have been mapped and a region responsible for dimerization defined (FIG. 8). The dimerization region was mutagenized using the GeneMorph II Random Mutagenesis Kit (Stratagene) as described (Lanza A M, Alper H S. 2011. Methods in Molecular Biology, Vol. 765, Strain Engineering: Methods and Protocols, Ed. J. A. Williams, Humana Press Inc., Totowa, N.J. pp 253-274). The Rep gene was error prone PCR amplified from the pINT pR pL ColE2 Rep vector with the kit enzyme. The mutagenized dimerization domain (359 bp BstB1/EcoRI fragment; FIG. 8) was cloned back into the pINT pR pL ColE2 Rep vector replacing the non mutagenized 359 bp BstB1/EcoRI fragment. An integrated pINT pR pL ColE2 Rep library was then made by mass genome integration without purification of the mutagenized plasmid pool into NTC54208 containing the pAH69 integration plasmid. The integrated Rep library was transformed with the kanR pDNAVACCUltra5-C2-P5/6,4/6-T7RBS EGFP fluorescent ColE2 reporter plasmid and transformants plated on LB+kanamycin agar plates and grown at 37° C. This EGFP reporter plasmid allows 1) visual selection of plasmid copy number improvement using a Dark Reader for agar plate illumination; and 2) quantitative copy number evaluation (fluorescence is linear with copy number) in liquid culture using a fluorometer (BioTek FLx800 microplate fluorescence reader).

Two colonies were isolated from 30,000 screened cells with significantly higher colony fluorescence. Both cell lines were verified to have improved pDNAVACCUltra5-C2-P5/6,4/6-T7RBS EGFP plasmid copy number in liquid culture demonstrating increased fluorescence corresponds to increased copy number.

The lambda repressor-$P_L$-ColE2 Rep regions from genomic DNA from these two cell lines were amplified by PCR and sequenced to determine the basis for improvement. One colony had a mutation in the lambda repressor which presumably reduces the activity of the repressor leading to Rep protein overexpression. This demonstrates that alternations to the vector backbone that increase $P_L$ promoter activity improve ColE2 plasmid copy number. Thus ColE2 copy number, like R6K plasmids, will be improved by making a cell line with the ColE2 Rep protein (or Rep protein copy number improving mutations) expressed from pINT pR pL vectors incorporating the lambda repressor binding site OL1 mutations (OL1-G and OL1-G to T) identified in Example 1.

The second colony had a mutation in the Rep protein (G194D; SEQ ID NO:16). This mutation was introduced back into the pINT pR pL ColE2 Rep vector to create the pINT pR pL ColE2 Rep protein mutant (G194D) (SEQ ID NO:18). The integration plasmid was integrated into NTC54208 (XL1Blue-sacB [dcm-]) to create cell line NTC701131 as described in Example 1. ColE2 plasmid production yields were improved in the ColE2 Rep protein mutant cell line NTC701131, compared to the parental ColE2 Rep protein cell line NTC641711 in both shake flask and fermentation culture (Table 3). This demonstrates that the ColE2 Rep protein, like the R6K Rep protein, can be mutagenized to create copy number improving variants.

Combining the ColE2 Rep protein G194D mutant with pINT pR pL vector incorporating the lambda repressor binding site OL1 OL1-G to T mutation identified in Example 1 further increased copy number (cell line NTC710351=NTC54208-pR pL (OL1-G to T) ColE2 rep G194D) and fermentation production yields (Example 3).

TABLE 3

NTC9385C-Luc plasmid performance in different processes and production cell lines[a]

| ColE2 Plasmid production cell line | LB shake flask (37 C.) | | | Plasmid + Shake flask (37 C.)[c] | | | HyperGRO fermentation | | |
|---|---|---|---|---|---|---|---|---|---|
| | $OD_{600}$ | mg/L | Spec yield[b] | $OD_{600}$ | mg/L | Spec yield[b] | $OD_{600}$ | mg/L | Spec yield[b] |
| NTC641711 | 3.4 | 1.4 | 0.4 | 13.0 | 12.3 | 0.93 | 148 | 61 | 0.4 |
| NTC701131 | 3.4 | 3.1 | 0.9 | 16.6 | 17.9 | 1.1 | 113 | 110 | 1.0 |
| Rep mutant | | | | | | | 140 | 142 | 1.0 |

[a] All plasmid preparations at harvest were high quality monomer.
[b] Specific yield = mg plasmid/L/$OD_{600}$
[c] Plasmid + media from Thomson Instruments Company Additional rounds of mutagenesis of the wild type Rep protein, or mutagenesis of mutant Rep protein such as G194D may be performed to further improve copy number. The entire Rep protein or subfragments can be mutagenized (e.g. BamH1-EcoRI fragment for entire Rep protein; FIG. 8). The ideal mutant will be similar to the R6K Rep protein mutants 'P42L and P113S' and 'P42L, P106L and F107S' (Example 1) with higher copy number at 37-42° C. (i.e. higher levels of replication inducing monomeric Rep protein are produced from the heat inducible $P_R$ $P_L$ promoters) to facilitate adaptation into NTC's inducible fermentation plasmid production process as in Example 1.

ColE2 Origin Vectors:

The following vectors containing the minimal ColE2-P9 origin (Yagura and Itoh 2006 *Biochem Biophys Res Commun* 345:872-877) and various origin region modifications were constructed.

+7-ssiA:

This combines the ColE2 origin (+7) (SEQ ID NO:4) with ssiA from plasmid R6K (SEQ ID NO:21). Thus ssiA vectors contain, in addition to the ColE2-P9 origin, a downstream primosome assembly site. Like most plasmid origins, the ColE2 origin contains a primosomal assembly site about 100 bp downstream of the origin (Nomura et al Supra, 1991). This site primes lagging strand DNA replication (Masai et al 1990 *J Biol Chem* 265:15124-15133) which may improve plasmid copy number or plasmid quality. The ColE2 PAS (ssiA) is similar to PAS-BH (ColE1 ssiA=PAS-BL Marians et al 1982 *J Biol Chem* 257:5656-5662) and both sites (and PAS-BH) are CpG rich ØX174 type PAS. A CpG free PAS (ssiA from R6K; Nomura et al Supra, 1991; SEQ ID NO:21) that acts as a dnaA, dnaB dnaC (ABC) primosome on a dnaA box hairpin sequence (Masai et al 1990 *J Biol Chem* 265:15134-15144) was selected for inclusion in the +7-ssiA vectors. Alternative ABC or ØX174 type PAS sequences are functionally equivalent to ssiA from R6K, and may be substituted for ssiA in these ColE2 replication origin vectors.

+7-ssiA vectors were constructed by replacing the pUC origin NheI-DraIII region (FIG. 1) with a NheI-DraIII compatible synthetic ssiA-+7 ColE2 origin restriction fragment (FIG. 2, FIG. 4). Plasmids were transformed into ColE2 plasmid production NTC641711. The correct ColE2 vectors were identified by restriction digestion and sequence verified.

+7 (No ssiA):

This deletes the ssiA sequence from +7-ssiA while retaining the ColE2 origin (+7) (SEQ ID NO:4). The ssiA sequence was removed by NheI-MfeI digestion, the sites blunted with Klenow and the vector religated to delete the 64 bp ssiA region. Plasmids were transformed into ColE2 plasmid production host NTC641711. The correct ColE2 vector was identified by restriction digestion and sequence verified.

+7 CpG-ssiA:

This combines the ColE2 replication origin (+7 CpG) (SEQ ID NO:5) with ssiA from plasmid R6K (SEQ ID NO:21). The single CpG in the ColE2 replication origin (Table 4) was removed from the vector by site directed mutagenesis. Plasmids were transformed into ColE2 plasmid production host NTC641711. The correct ColE2 vector was identified by restriction digestion and sequence verified.

+16-ssiA:

This combines the ColE2 replication origin (+16) (SEQ ID NO:7) with ssiA from plasmid R6K (SEQ ID NO:21). A 16 bp region of homology downstream of the ColE2-P9 replication origin is conserved with the ColE3 replication origin. This 16 bp region was added to the vector by site directed mutagenesis. Plasmids were transformed into ColE2 plasmid production host NTC641711. The correct ColE2 vector was identified by restriction digestion and sequence verified.

Min-ssiA:

This combines the ColE2 Min replication origin (SEQ ID NO:6) with ssiA from plasmid R6K (SEQ ID NO:21). This is the minimal 32 bp ColE2 sequence sufficient for replication defined by Yasueda et al 1989 *Mol Gen Genet* 215:209) (SEQ ID NO:28), extended by an additional 6 bp (Table 4). This vector was created by site directed mutagenesis of the +7-ssiA clone. Plasmids were transformed into ColE2 plasmid production host NTC641711. The correct ColE2 vector was identified by restriction digestion and sequence verified.

The series of plasmids were transformed into ColE2 plasmid production host NTC701131 (Rep mutant). The resultant cell lines were then used determine plasmid copy number and quality (Table 4). Two different backbones were evaluated with the +7-ssiA and +16-ssiA ColE2 replication origins to determine the effect of plasmid sequence alterations.

The results demonstrate that the four replication origin variants containing the ssiA sequence [+7-ssiA; +16-ssiA; +7 (CpG free) ssiA; Min-ssiA] are functional in NTC701131, replicating to a similar copy number (0.73-1×). All plasmids were high quality monomer. This demonstrates that any of these minimal ColE2 origin variants can function as a plasmid replication origin to produce high quality plasmid.

Yagura et al Supra, 2006 have demonstrated that the Min ColE2 Replication origin (SEQ ID NO:28, which is reverse complement of residues 7-38, in FIG. 1 of Yagura et al Supra, 2006) can be further deleted without eliminating replication function. Yagura et al, Supra, 2006, demonstrated that the core sequence is residues 8-35, with residues 5-36 are required for full activity. The +7 ColE2 Replication origin (SEQ ID NO:4; which is the reverse complement of residues 0-44 in FIG. 1 of Yagura et al Supra, 2006) could therefore be reduced to span residues 8-35 or 5-36 of FIG. 1 of Yagura et al Supra, 2006. Such vectors should replicate similarly to the disclosed vectors. As well, a number of base changes can be made within the core ColE2 origin 8-34 region that do not affect ColE2 replication (see changes to residues that retain function in Table 2 in Yagura et al Supra, 2006).

A surprising observation that is contrary to the teachings of Yagura et al Supra, 2006 is that the +7(CpG free)-ssiA ColE2 origin is fully functional. This origin contains a change of a G to C in residue 36 (FIG. 1 Yagura et al Supra, 2006). This change is predicted to reduce origin activity (Relative transformation frequency 5 fold reduced with 36 G-C to C-G; Table 2 in Yagura et al Supra, 2006). This may be due to the different context in the +7(CpG free)-ssiA ColE2 origin, or the longer origin fragment (0-44). Regardless, the 121 bp +7(CpG free)-ssiA ColE2 origin (SEQ ID NO 29) or +7(CpG free) ColE2 origin (SEQ ID NO 5) are smaller CpG free replication origin alternatives to the 260 bp CpG free R6K replication origins (SEQ ID NO:22). CpG free ColE2 origins may be utilized to construct CpG free plasmid vectors, or to retrofit the replication origin in existing vectors with a CpG free alternative replication origin. Combinations of a CpG free ColE2 or R6K replication origin with a CpG free RNA-OUT selection marker may be utilized to construct antibiotic free CpG free plasmid vectors, or to retrofit the selection marker-replication origin region in existing vectors with an antibiotic free-CpG free alternative selection marker-replication origin.

The ssiA sequence was not necessary for plasmid replication, although removal of ssiA in +7 (no ssiA) reduced copy number to 55% of +7 (ssiA). Thus inclusion of a primosomal assembly site is beneficial to ColE2 plasmid copy number.

TABLE 4

ColE2 Origin EGFP vector production in NTC701131 ColE2 production cell line [b]

| Origin[c] | Cell line ID# | OD600 | mg/L | Specific Yield (mg/L/ OD$_{600}$) | Relative copy number [a] |
|---|---|---|---|---|---|
| +7-ssiA (NTC9385C) | 071-020-2D | 13.5 11.4 12.5 | 20.7 20.4 27.2 | 2.3 1.8 2.2 (2.1 avg) | 1x |
| +16-ssiA | 071-029-1A | 19.6 16.5 13.1 | 23.5 20.9 24.8 | 1.2 1.3 1.9 (1.5 avg) | 0.70x |
| +7(CpG free)-ssiA | 071-020-3D | 10.5 8.4 10.1 | 25.1 11.6 14.1 | 2.4 1.4 1.4 (1.7 avg) | 0.83x |
| Min-ssiA | 071-020-4D | 11.3 15.9 13.3 | 13.7 37.2 14.8 | 1.2 2.3 1.1 (1.5 avg) | 0.73x |
| +7 (no ssiA) | 071-020-5D | 12.8 13.5 13.5 | 17.2 16.4 14.5 | 1.3 1.2 1.1 (1.2 avg) | 0.55x |
| +7-ssiA (NTC9685C) | 071-020-6D | 14.7 13.2 11.7 | 22.3 21.3 14.9 | 1.5 1.6 1.3 (1.5 avg) | 0.70x |
| +16-ssiA (VA1-SV40) | 071-020-7D | 13.5 11.9 13.2 | 26.9 17.7 18.8 | 1.9 1.5 1.4 (1.6 avg) | 0.76x |

[a] Average specific yield/+7-ssiA average specific yield (specific yield = mg plasmid/L/OD600)
[b] Plasmid + media, 37 °C. throughout growth conditions. All plasmid preparations at harvest were high quality monomer
[c] NTC ColE2 origin sequences
+7: caaaagggcgctgttatctgataaggcttatctggtctcattttg (SEQ ID NO: 4) Min bold underlined
+7 (CpG free): caaaagggGgctgttatctgataaggcttatctggtctcattttg (SEQ ID NO: 5)(C to G change in bold underlined core to eliminate CpG is uppercase double underlined)
Min: The 32 bp minimal origin defined by Yasueda et al Supra, 1989 (SEQ ID NO: 28) is Bold underlined: ggcgctgttatctgataaggcttatctggtctcatttt (SEQ ID NO: 6)
+16: CTGCTCAAAAAGACGC caaaag ggcgctgttatctgataaggcttatctggtctcattttg (SEQ ID NO: 7) Min bold underlined, additional 16 bp in +16 is uppercase Example 3: NTC9382C, NTC9385C, NTC9382R, NTC9385R, NTC9682C, NTC9685C, NTC9682R, and NTC9685R Vectors A series of AF eukaryotic expression vectors incorporating these novel ColE2-P9 derived vector origins were made. To replace the pUC origin, the +7 (ssiA) ColE2 origin from Example 2 was selected as well as the R6K origin (SEQ ID NO:1) from Example 1. The features of these vectors (NTC9382C, NTC9385C, NTC9382R, NTC9385R, NTC9682C, NTC9685C, NTC9682R, and NTC9685R) are summarized in Table 5.

NTC9682C, NTC9685C (FIG. 2), NTC9682R, NTC9685R (FIG. 3) are antibiotic-free RNA-OUT ColE2 origin (C) or R6K origin (R) versions of the pUC origin NTC8682, NTC8685 (FIG. 1) equivalents disclosed in Williams J A, Supra, 2010. These vectors contain the SV40 enhancer upstream of the CMV enhancer, and Adenoviral serotype 5 VA RNAI regulatory RNA (VARNAI).

NTC9382C, NTC9385C (FIG. 4), NTC9382R, NTC9385R (FIG. 5) are versions without the SV40 enhancer or VARNAI sequences.

NTC9682C, NTC9682R, NTC9382C, and NTC9382R all express the secreted transgene product as TPA fusion proteins while NTC9685C, NTC9685R, NTC9385C, and NTC9385R all express the native transgene product from a vector encoded ATG start codon.

The remainder of the vector sequences is identical between the different vectors, with the exception that the two R vectors NTC9682R and NTC9382R (FIG. 3, FIG. 5) contain the trpA bacterial terminator, which is absent in the two C vectors NTC9682C and NTC9382C (FIG. 2, FIG. 4).

An R6K gamma origin vector was constructed by swapping in the R6K gamma origin (SEQ ID NO:1) in a NotI-DraIII R6K origin synthetic gene for the corresponding NotI-DraIII pUC origin region in NTC8685. The NTC9682R, NTC9685R NTC9382R, NTC9385R vectors were made by standard restriction digestion mediated fragment swaps. The ColE2 origin vectors were constructed in a similar fashion, by swapping in the +7 ssiA ColE2 origin in a NheI-DraIII synthetic gene for the corresponding NheI-DraIII pUC origin region. The NTC9682C, NTC9685C, NTC9382C, NTC9385C vectors were made by standard restriction digestion mediated fragment swaps. The 466 bp Bacterial region [NheI site-trpA terminator-R6K Origin-RNA-OUT-KpnI site] for NTC9385R and NTC9685R is shown in SEQ ID NO:19. The 281 bp Bacterial region [NheI site-ssiA-ColE2 Origin (+7)-RNA-OUT-KpnI site] for NTC9385C and NTC9685C is shown in SEQ ID NO:20.

High fermentation yields in HyperGRO media are obtained with these vectors. For example 695 mg/mL with NTC9685R-EGFP in R6K production cell line NTC711231 (Table 1) and 672 mg/L with NTC9385C-EGFP in ColE2 production cell line NTC710351.

These are just a few possible nonlimiting vector configurations. Many alternative vector configurations incorporating the novel R6K or ColE2 origin vector modifications may also be made, including but not limited to vectors with alternative selection markers, alternative promoters, alternative terminators, and different orientations of the various vector-encoded elements or alternative R6K or ColE2 origins as described in Examples 1 and 2.

TABLE 5

NTC9382C, NTC9385C, NTC9382R, NTC9385R, NTC9682C, NTC9685C, NTC9682R, and NTC9685R vectors

| Vector | Origin | VA RNAI present | SV40 enhancer | Transgene targeting |
|---|---|---|---|---|
| NTC9382C | ColE2-P9 | No | No | Secretion (TPA) |
| NTC9382R | R6K | No | No | Secretion (TPA) |
| NTC9682C | ColE2-P9 | Yes | Yes | Secretion (TPA) |
| NTC9682R | R6K | Yes | Yes | Secretion (TPA) |
| NTC9385C (SEQ ID NO: 8) | ColE2-P9 | No | No | Native |
| NTC9385R (SEQ ID NO: 2) | R6K | No | No | Native |
| NTC9685C (SEQ ID NO: 9) | ColE2-P9 | Yes | Yes | Native |
| NTC9685R (SEQ ID NO: 3) | R6K | Yes | Yes | Native |

An example strategy for cloning into these vectors is outlined below.

```
GTCGACATG--------Gene of interest----Stop codon
  SalI

------AGATCT
      BglII
```

For the NTC9385C, NTC9685C, NTC9385R, and NTC9685R vectors, the ATG start codon (double underlined) is immediately preceded by a unique SalI site. The SalI site is an effective Kozak sequence for translational initiation. In NTC9382C, NTC9682C, NTC9382R, and NTC9682R, the SalI site is downstream in frame with the optimized TPA secretion sequence (SEQ ID NO:25). The TPA ATG start codon is double underlined and the SalI site single underlined. SEQ ID NO:25: TPA secretion sequence atggatgcaatgaagagagggctctgctgtgtgctgctgctgtgtggagcagtctt cgtttcgcccagcggtaccggatccgtcgac For precise cloning, genes are copied by PCR amplification from clones, cDNA, or genomic DNA using primers with SalI (5' end) and BglII (3' end) sites. Alternatively, genes are synthesized chemically to be compatible with the unique SalI/BglII cloning sites in these vectors.

For NTC9385C, NTC9685C, NTC9385R, and NTC9685R, the start codon ATG may immediately follow the SalI site (GTCGACATG) since the SalI site is a high function Kozak sequence. For all vectors one or two stop codons (preferably TAA or TGA) may be included after the open reading frame, prior to the BglII site. A PCR product or synthetic gene designed for NTC9385C, NTC9685C, NTC9385R, and NTC9685R is compatible with, and can also be cloned into, the NTC9382C, NTC9682C, NTC9382R, and NTC9682R vectors.

EGFP and muSEAP transgene versions NTC9385C, NTC9685C, NTC9385R, and NTC9685R were constructed by standard restriction fragment swaps. The muSEAP gene is secreted using its endogenous secretion signal, while EGFP is cell associated. Expression levels in vitro were determined using EGFP, while expression levels in vivo were determined using muSEAP. Expression levels were compared to the NTC8685 parent vector, the gWIZ vector, and a minicircle comparator.

Adherent HEK293 (human embryonic kidney), A549 (human lung carcinoma), cell lines were obtained from the American Type Culture Collection (Manassas, Va., USA). Cell lines were propagated in Dulbecco's modified Eagle's medium/F12 containing 10% fetal bovine serum and split (0.25% trypsin-EDTA) using Invitrogen (Carlsbad, Calif., USA) reagents and conventional methodologies. For transfections, cells were plated on 24-well tissue culture dishes. plasmids were transfected into cell lines using Lipofectamine 2000 following the manufacturer's instructions (Invitrogen).

Total cellular lysates for EGFP determination were prepared by resuspending cells in cell lysis buffer (BD Biosciences Pharmingen, San Diego, Calif., USA), lysing cells by incubating for 30 min at 37° C., followed by a freeze-thaw cycle at −80° C. Lysed cells were clarified by centrifugation and the supernatants assayed for EGFP by FLX800 microplate fluorescence reader (Bio-Tek, Winooski, Vt., USA). The results are summarized in FIG. 9 and Table 6.

Groups of five mice were injected with plasmid DNA in an IACUC-approved study. Five micrograms of muSEAP plasmid in 25 or 50 μL of phosphate-buffered saline (PBS) was injected intramuscularly (IM) into a tibialis cranialis muscles of female BALB/c mice or ND4 Swiss Webster mice (6 to 8 weeks old) followed by Ichor TriGrid electroporation. SEAP levels in serum were determined using the Phospha-light SEAP Reporter Gene Assay System from Applied Biosystems (Foster City, Calif.) according to the manufacturer's instructions. The results are summarized in FIG. 10 and Table 6.

The NTC9385C, NTC9685C, NTC9385R, and NTC9685R vectors had similar expression to the parent NTC8685 vector in vitro, and higher expression than the gWIZ comparator (FIG. 9). Thus substitution of the R6K or ColE2 replication origin for the pUC origin was not detrimental for eukaryotic cell expression. However, surprisingly, in vivo expression was dramatically improved compared to NTC8685 or gWIZ with the ColE2 and R6K origin vectors (FIG. 10). For example the NTC9385C vector was unexpectedly improved 1.5 to 3.8× that of NTC8385 (Table 6) or NTC8685 (not shown) after IM delivery with EP.

TABLE 6 gWIZ and NTC9385C Nanoplasmid expression compared to NTC8685

| Plasmid | % NTC8685 expression in vitro [a] | % NTC8685 expression T = 7 days BALB/c [b] | % NTC8685 expression T = 7 days ND4 [b] | % NTC8685 expression T = 28 days BALB/c [b] | % NTC8685 expression T = 28 days ND4 [b] |
|---|---|---|---|---|---|
| gWIZ | 58 | 59 | 57 | 21 | 57 |
| NTC8385 | NA | NA | 101 | NA | 101 |
| NTC9385C | 92 | 377 | 349 | 150 | 233 |
| Minicircle [c] | NA | 89 | NA | 40 | NA |

[a] 100 ng/well EGFP transgene vectors transfected with lipofectamine into HEK293 cells
[b] murine SEAP (muSEAP) transgene vectors in 8-10 week old BALB/c or ND4 Swiss Webster female mice, 5 μg dose with EP intramuscular into one anterior tibialis muscle followed by Ichor TriGrid electroporation. 25 μL dose for ND4 mice, 50 μL dose for BALB/c.
[c] Minicircle equivalent to NTC9385C or NTC9385R, with NheI-KpnI region containing the replication origin and RNA-OUT selection marker (bacterial region) removed from NTC8385-muSEAP by SpeI/NheI digestion, gel purification of the eukaryotic region, in vitro ligation and supercoiling with DNA gyrase. The SpeI site is the same site used to truncate the CMV promoter to make NTC8685 and the NTC9385C-muSEAP vector so the minicircle eukaryotic region is the same as NTC9385C-muSEAP, the difference being the C2 and RNA-OUT region including the KpnI site is deleted in the minicircle.
NA = Not assayed This improved in vivo expression was not specific to the CMV promoter. Versions of NTC8685-muSEAP and NTC9385C-muSEAP were constructed in which the murine creatine kinase (MCK) promoter (3 copies of the MCK Enhancer upstream of the MCK promoter and 50 bp of the MCK exon 1 leader sequence; Wang B, Li J, Fu F H, Chen C, Zhu X, Zhou L, Jiang X, Xiao X. 2008. *Gene Ther* 15:1489) was substituted for the CMV promoter. The swaps replaced the entire CMV enhancer CMV promoter-exon 1 leader (NTC8685: from a XbaI site immediately after the SV40 enhancer to a SacII site in the CMV derived exon 1 leader sequence FIG. 1; NTC9385C: from the KpnI site to a SacII site in the CMV derived exon 1 leader sequence FIG. 4) with the MCK enhancer, MCK promoter-exon 1 leader retaining the HTLV-I R portion of exon 1. Purified plasmid DNA from the resultant vectors, NTC8685-MCK-muSEAP (4847 bp) and NTC9385C-MCK-muSEAP (3203 bp), was injected IM into one anterior tibialis muscle of 8-10 week old BALB/c female mice (5 mice/group), 5 μg dose in 50 μL, followed by Ichor TriGrid electroporation as described in Table 6. SEAP levels in serum was determined on day 28 (T=28) post delivery. The NTC9385C-MCK-muSEAP vector (98.4±55.8) had 4.5× higher average expression than NTC8685-muSEAP (22.0±10.9). All 5 NTC9385C-MCK-muSEAP injected mice had higher muSEAP levels than any of the NTC8685-muSEAP mice. This demonstrates that improved in vivo expression with the Nanoplasmid vectors of the invention is not specific to the CMV promoter.

While the basis for expression improvement is unknown, it is not simply due to the size difference between the parent pUC origin vectors and the modified R6K origin-RNA selection marker or ColE2 origin-RNA selection marker vectors of the invention, since expression was not improved with a minicircle comparator vector that contains no bacterial region (Table 6). This demonstrates improved in vivo expression with the R6K origin-RNA selection marker or ColE2 origin-RNA selection marker vectors is not the result of simple elimination of a threshold amount of bacterial region sequences.

Reduction of the vector spacer region size as described herein by replacement of the spacer region replication origin and selection marker with the R6K, ColE2 origin-RNA selection marker vectors of the invention will also increase the duration of in vivo expression since expression duration is improved with plasmid vectors in which the bacterial region is removed (minicircle) or replaced with a spacer region of up to at least 500 bp (Lu J, Zhang F, Xu S, Fire A Z, Kay M A. 2012. *Mol Ther.* 20:2111-9). Thus the replicative minicircle vectors of the invention also have additional utility for applications requiring extended duration expression, such as: liver gene therapy using hydrodynamic delivery with transgenes such as α-1 antitrypsin (AAT) for AAT deficiency, Coagulation Factor VIII for Hemophilia A Therapy or Coagulation Factor IX for Hemophilia B Therapy etc: lung gene therapy with transgenes such as Cystic fibrosis transmembrane conductance regulator (CFTR) for cystic fibrosis etc; muscle gene therapy with transgenes such as the GNE gene for Hereditary inclusion body myopathies (HIBM), or dystrophin or dystrophin minigenes for duchenne muscular dystrophy (DMD).

Example 4: Spacer Region and Intron Modified Nanoplasmid Vectors

NTC8685 (SR=1465 bp) has much lower expression than NTC9385R (SR=466 bp) and NTC9385C (SR=281 bp). A minimal pUC origin vector was constructed with an 866 bp spacer region (NTC8385-Min; contains $P_{min}$ minimal pUC origin-RNA-OUT). These vectors were tested for expression in vitro (lipofectamine 2000 delivery) and in vivo after intradermal electroporation delivery. As with Intramuscular injection (Example 3), the results (Table 7) demonstrated ColE2 and R6K origin vector dramatically improved in vivo expression after intradermal delivery compared to NTC8685. For example the NTC9385C vector was unexpectedly improved 2.7 to 3.1× compared to NTC8685 while the NTC9385R vector was unexpectedly improved 5.3 to 6.3× that of NTC8685 (Table 7). The 866 bp minimal pUC origin vector also improved expression to 1.4-1.9× that of NTC8685. This demonstrates improved in vivo expression with the NTC9385C and NTC9385R vectors is not limited to muscle tissue, and is observed also after intradermal delivery. Inclusion of the C2×4 eukaryotic transcription terminator in the NTC9385C vector further improved in vivo expression to 2.9 to 4.1× compared to NTC8685. This demonstrates improved in vivo expression with Nanoplasmid vectors may be obtained with alternative/additional sequences flanking the bacterial region.

A NTC9385R derivative was made in which the RNA-OUT antibiotic free marker was transferred to the intron (NTC9385Ra-O2 SEQ ID NO:39; RNA-OUT SEQ ID NO:23) inserted into the unique HpaI site in the intron (SEQ ID NO: 30). This vector encodes the R6K replication origin in the spacer region (SR=306 bp). To determine splicing accuracy NTC9385Ra-O2-EGFP was transfected into the A549 cell line and cytoplasmic RNA isolated. The RNA was reverse transcribed using an EGFP specific primer, and PCR amplified using Exon 1 and Exon 2 specific primers. The resultant PCR product (a single band) was determined by sequencing to be the correct spliced exon1-exon2 fragment. This demonstrated that intronic RNA-OUT is accurately removed by splicing and does not interfere with splicing accuracy. NTC9385Ra-O2-EGFP also demonstrated improved in vivo expression compared to NTC8685 (Table 7: 1.6-3.5×). This demonstrates that Nanoplasmid vectors with improved expression of the current invention may encode the RNA selection marker in the intron rather than the spacer region.

The improved expression level after intradermal delivery demonstrates the application of Nanoplasmid vectors of the invention for cutaneous gene therapy applications, for example, for wound healing, burns, diabetic foot ulcer, or critical limb ischemia therapies using growth factors such as hypoxia inducible factor, hypoxia inducible factor 1α, keratinocyte growth factor, vascular endothelial growth factor (VEGF), fibroblast growth factor-1 (FGF-1, or acidic FGF), FGF-2 (also known as basic FGF), FGF-4, placental growth factor (P1GF), angiotensin-1 (Ang-1), hepatic growth factor (HGF), Developmentally Regulated Endothelial Locus (Del-1), stromal cell derived factor-1 (SDF-1), etc.

vectors <1.2 kb are highly resistant to shear forces used with gene therapy delivery formulation (Catanese et al 2012. *Gene Ther* 19:94-100).

RNA Pol III Nanoplasmid vectors were made by standard restriction digestion mediated fragment swaps to combine either U6 or H1 RNA Pol III promoter-target RNA-TTTTTT terminator (Eukaryotic region) with either the 466 bp Bacterial region [NheI site-trpA terminator-R6K Origin-RNA-OUT-KpnI site; SEQ ID NO:19] for NTC9385R-U6 and NTC9385RE-U6 vectors (Table 8) or the 281 bp Bacterial region [NheI site-ssiA-ColE2 Origin (+7)-RNA-OUT-KpnI site; SEQ ID NO:20] for NTC9385C-U6 and NTC9385CE-U6 vectors (Table 8). Versions were modified to express from the U6 promoter eRNA18, a single stranded RNA the expression of which can be quantified by Reverse transcriptase dependent RT-PCR. Vector performance (U6 promoter mediated eRNA18 RNA expression) was determined in total RNA extracted from HEK293 at either 25 or 48 hrs after lipofectamine 2000 mediated transfection as described (Luke J, Simon G G, Soderholm J, Errett J S, August J T, Gale M Jr, Hodgson C P, Williams J A. 2011. *J Virol.* 85:1370). These results (Table 9) demonstrate Nanoplasmid RNA Pol III vectors direct dramatically improved RNA expression relative to a plasmid RNA Pol III vector (NTC7485-U6-eRNA18) comparator.

TABLE 7

SR vector expression in vitro and in vivo

| muSEAP Vector [b] | SR [a] | SR (bp) | Intron [a] | A549 $(A_{405})$ [d] | HEK-293 $(A_{405})$ [d] | ID + EP [c] (pg/mL) T = 4 | ID + EP [c] (pg/mL) T = 7 | ID + EP [c] (pg/mL) T = 14 |
|---|---|---|---|---|---|---|---|---|
| NTC8685 | T-VA1-BH-P-AF→ | 1465 | HR- β | 0.240 ± 0.029 (1.0x) | 3.002 ± 0.188 (1.0x) | 1.9 ± 1.2 (1.0x) | 6.7 ± 4.1 (1.0x) | 5.0 ± 3.9 (1.0x) |
| NTC8385-Min[e] | T-P$_{min}$-AF→ | 866 | HR- β | 0.495 ± 0.027 (2.1x) | 2.713 ± 0.177 (0.9x) | 3.7 ± 2.7 (1.9 x) | 12.4 ± 8.1 (1.9 x) | 7.1 ± 5.2 (1.4 x) |
| NTC9385R (SEQ ID NO: 2) | T ←R- AF→ | 466 | HR- β | 0.604 ± 0.04 (2.5x) | 3.036 ± 0.169 (1.0x) | 12.0 ± 7.4 (6.3 x) | 35.5 ± 31.1 (5.3 x) | 29.9± 23.4 (6.0 x) |
| NTC9385C (SEQ ID NO: 8) | ←C - AF→ | 281 | HR- β | 0.267 ± 0.053 (1.1x) | 2.720 ± 0.228 (0.9x) | 5.8 ± 3.0 (3.1 x) | 20.8 ± 9.6 (3.1 x) | 13.5 ± 9.8 (2.7x) |
| NTC9385C C2x4 | ←C - AF→ | 281 | HR- β | 0.214 ± 0.017 (0.89x) | 2.472 ± 0.197 (0.82x) | 5.6 ± 2.3 (2.9 x) | 27.7 ± 20.3 (4.1 x) | 16.0 ± 14.3 (3.2x) |
| NTC9385R a-O2 (SEQ ID NO: 39) | T ←R AF→ | 306 | HR- ←AF- β | 0.524 ± 0.071 (2.2x) | 3.065 ± 0.220 (1.0x) | 3.6 ± 2.8 (1.9 x) | 23.4 ± 16.5 (3.5 x) | 7.8 ± 8.0 (1.6 x) |

[a] Prokaryotic terminator = T; HTLV-IR = HR; B globin 3' acceptor site = β; RNA-OUT = AF; pUC origin = P; minimal pUC origin = P$_{min}$; R6Kγ origin = R; ColE2-P9 origin = C; C2x4 eukaryotic transcription terminator = C2x4
[b] All plasmids produced in XL1Blue dcm- host strains. P vectors were produced in dcm- XL1Blue NTC54208; R vectors were produced in dcm- R6K rep cell line NTC711231 (OL1 G to T); C vectors were produced in dcm- ColE2 rep cell line NTC710351 (OL1 G to T).
[c] Dose = 50 μg in 50 μl saline injected intradermal (ID) with EP on day 0. 6 mice/group. Mean ± SD pg/mL muSEAP reported for day 4, 7 and 14. ( ) Mean muSEAP standardized to NTC8685
[d] muSEAP plasmid DNA transfected with Lipofectamine 2000. Mean ± SD A$_{405}$ reported 48 hrs post transfection. ( ) Mean A$_{405}$ standardized to NTC8685
[e] P$_{min}$ minimal pUC origin (SEQ ID NO: 42) and RNA-OUT (bacterial region = SEQ ID NO: 43)

Example 5: RNA Pol III Nanoplasmid Vectors

An example Nanoplasmid vector for RNA Pol III directed expression of RNA is shown in FIG. 11. This vector contains the human H1 RNA Pol III promoter, but an alternative promoter such as the murine U6 promoter can be substituted. This example vector expresses a 22 bp shRNA target RNA, but alternative RNAs may be expressed, including shorter or longer shRNAs, microRNAs, aptamer RNAs, hairpin RNAs, etc. This example vector is very small, with a monomer size of 442 bp. Small size is advantageous, since Random 22 bp shRNA (KP2F11) versions of NTC9385CE-U6 (903 bp NTC9385CE-U6-KP2F11 shRNA propagated in ColE2 rep cell line NTC710351) and NTC9385R-U6 (855 bp NTC9385R-U6-KP2F11 shRNA propagated in R6K rep cell line NTC711231) were fermented in HyperGRO media as described in Example 1 except fermentation and cultures for inoculations were grown at 37° C. throughout. Final yields were 149 mg/L (NTC9385CE-U6-KP2F11) and 216 mg/L (NTC9385R-U6-KP2F11 shRNA). This demonstrates that Nanoplasmid vectors for RNA Pol III expression (and RNA Pol II; Example 3) have superior manufacturing simplicity and yield compared to shRNA expressing minicircle vectors (Zhao et al 2011. *Gene Ther* 18:220-224). For example, optimal manufacture of minicircle vectors yields only 5 mg of minicircle per liter culture (Kay M A, He C Y, Chen Z Y. 2010. *Nat Biotechnol* 28:1287-1289).

TABLE 8

RNA Pol III Nanoplasmid vector expression

| Vector | Pol II Enhancer | Size (bp) | Transfection 1: RNA isolated 48 hr post transfection | | Transfection 2: RNA isolated 25 hr post transfection | |
|---|---|---|---|---|---|---|
| | | | HEK pg RNA/ 100 ng mRNA[a] | HEK Std[b] | HEK pg RNA/ 100 ng mRNA[a] | HEK Std[b] |
| NTC9385R-EGFP (negative control) | None | NA | 0.0 ± 0.0 | 0% | | |
| NTC8885MP-U6-eRNA18 | SV40 | 1578[c] | 62.2 ± 5.9 (1.3x) | 69% | | |
| NTC9385RE-U6-eRNA18 | SV40 | 1178 | 119.1 ± 13.9 (2.5x) | 98% | | |
| NTC9385R-U6-eRNA18 | None | 945[d] | 123.7 ± 8.0 (2.6x) | 82% | | |
| NTC9385CE-U6-eRNA18 | SV40 | 993 | 119.0 ± 13.9 (2.5x) | 83% | | |
| NTC9385C-U6-eRNA18 | None | 760[e] | 131.1 ± 10.5 (2.7x) | 70% | 57.3 ± 2.6 (5.0x) | 127% |
| NTC7485-U6-eRNA18 | SV40 | 2978 | 48.0 ± 1.3 (1x control) | 100% (100% control) | 11.5 ± 1.5 (1x) | 100% (control) |

[a]pg eRNA18 target/100 ng total RNA isolated post-transfection.
[b]Standardized mU6 expression compared to NTC7485-U6 shRNA eRNA18 vector (C) = test vector average pg RNA/C vector average pg RNA x test vector size (bp)/2978 x 100%
[c]$P_{min}$ minimal pUC origin (SEQ ID NO: 42) and RNA-OUT (bacterial region = SEQ ID NO: 43) with SV40 enhancer. H1 promoter version (with shRNA and no SV40) is 1035 bp
[d]R6K origin and RNA-OUT (bacterial region = SEQ ID NO: 19). H1 promoter version (with shRNA) is 635 bp
[e]C2 origin and RNA-OUT (bacterial region = SEQ ID NO: 20). H1 promoter version (with shRNA) is 442 bp (FIG. 11)

Example 6: Alternative RNA Selection Marker Nanoplasmid Vectors

Expression of Nanoplasmid vectors encoding RNA-OUT in the intron (both orientations of RNA-OUT SEQ ID NO:23 inserted into the unique HpaI site in the intron SEQ ID NO:30; NTC9385Ra-O1 dual and NTC9385Ra-O2 dual) demonstrated robust expression with RNA-OUT in either orientation in the intron (Table 9). Consistent with this, similarly high levels of expression are obtained with NTC9385Ra-O1 (SEQ ID NO:40) and NTC9385Ra-O2 (SEQ ID NO:39) which have opposite orientations of intronic RNA-OUT marker and the R6K origin in the spacer region. Nanoplasmid variants with the pMB1 antisense RNA RNAI (SEQ ID NO:31) with promoter and terminator region (RNAI selectable marker: SEQ ID NO:32 flanked by DraIII-KpnI restriction sites for cloning as described previously for RNA-OUT) substituted for RNA-OUT were constructed and tested for expression to determine if alternative selection markers may be utilized in place of RNA-OUT. The results (Table 9) demonstrate alternative RNA selection markers may be substituted for RNA-OUT. Substitution of RNAI for RNA-OUT in the vector backbone (NTC9385Ra-RNAI-O1) or in the intron in either orientation (NTC9385R-RNAI-O1 and NTC9385R-RNAI-O2) did not reduce expression relative to the corresponding RNA-OUT construct. To determine splicing accuracy, NTC9385R-RNAI-O1-EGFP and NTC9385R-RNAI-O2-EGFP were transfected into the A549 cell line and cytoplasmic RNA isolated from transfected HEK293 and A549 cells using the protein and RNA isolation system (PARIS kit, Ambion, Austin Tex.) and quantified by $A_{260}$. Samples were DNase treated (DNA-free DNase; Ambion, Austin Tex.) prior to reverse transcription using the Agpath-ID One step RT-PCR kit (Ambion, Austin Tex.) with a EGFP transgene specific complementary strand primer. Intron splicing was determined by PCR amplification of the reverse transcribed cytoplasmic RNA with the exon 1 and exon 2 specific primers. The resultant PCR product (a single band in each case) was determined by sequencing to be the correct spliced exon1-exon2 fragment. This demonstrated that, like intronic RNA-OUT, intronic RNAI in either orientation is accurately removed by splicing and does not interfere with splicing accuracy. This demonstrates that alternative RNA based selection markers could be substituted for RNA-OUT in the spacer region or the intron and that pMB1 RNAI is a preferred RNA based selection marker.

The RNAI transcription unit (SEQ ID NO: 32) may be substituted for the RNA-OUT selection marker (SEQ ID NO: 23) in any of the constructs described in Examples 1-6. Alternatively, the 108 bp RNAI antisense repressor RNA (SEQ ID NO: 31) may be substituted for the 70 bp RNA-OUT antisense repressor RNA (SEQ ID NO: 24) retaining the flanking RNA-OUT transcription control sequences in any of the constructs described in Examples 1-6. RNAI regulated vectors may be grown in RNAII-SacB regulated cell lines further expressing, as required, R6K, ColE2-P9, or ColE2 related rep protein. RNAII-SacB regulated cell lines may be made replacing the RNA-IN sequence in pCAH63-CAT RNA-IN-SacB (P5/6 6/6) with a RNAII target sequence as described in Williams, J A Supra, 2008 included herein by reference. Alternatively, RNAII regulated vectors may be grown in any of the RNAII regulated chromosomal selection marker cell lines disclosed in Grabherr and, Pfaffenzeller Supra, 2006; Cranenburgh Supra, 2009. These cell lines would be modified for expression, as required, of R6K, ColE2-P9, or ColE2 related rep protein.

Another preferred RNA based selection marker, IncB plasmid RNAI (SEQ ID NO:33; SEQ ID NO:34), is shown in FIG. 12. A cell line for antibiotic free sucrose selection of IncB RNAI expressing plasmid vectors is created by modification of the genomically expressed RNA-IN-SacB cell lines for RNA-OUT plasmid propagation disclosed in Williams, J A Supra, 2008 by replacement of the 68 bp RNA-IN regulator in a PstI-MamI restriction fragment with a 362 bp PstI-MamI IncB RNAII regulator (SEQ ID NO:35). Alternatively, RNA-OUT may be substituted with one of the many RNA based selection markers know in the art.

the numerous additional Rep protein dependent plasmids that are know in the art, for example the Rep protein dependent plasmids described in del Solar et al Supra, 1998 which is included herein by reference. Likewise, the vectors may encode a diversity of transgenes different from the examples provided herein, for example, antigen genes for a variety of pathogens, or therapeutic genes such as hypoxia inducible factor, keratinocyte growth factor, factor IX, factor VIII, etc, or RNA genes such as microRNAs or shRNA. Likewise, the eukaryotic region may express RNA from a RNA Pol III promoter as described herein. The orientation of the various vector-encoded elements may be changed relative to each other. The vectors may optionally contain additional functionalities, such as nuclear localizing

TABLE 9

High level expression is obtained with pMB1 RNAI or RNA-OUT antisense RNA vectors

| Vector (EGFP) | Spacer region [a] | SR (bp) | Intron [a] | A549 FU [b] (T = 48 hr mean + SD) | HEK293 FU [b] (T = 48 hr mean + SD) |
|---|---|---|---|---|---|
| NTC8685 | T-VA1-BH-P-AF-SV40 | 1465 | HR- β [c] | 8546 ± 1163 (1.0x) | 62068 ± 1760 (1.0x) |
| NTC8385 (0.85 kb) [d] | T-P$_{min}$-AF-BE | 866 | HR- β [c] | 9364 ± 966 (1.10x) | 31482 ± 1822 (0.51x) |
| NTC9385C (SEQ ID NO: 8) | ←C -AF→ | 281 | HR- β [c] | 8860 ± 382 (1.04x) | 33356 ± 1489 (0.54x) |
| NTC9385R (SEQ ID NO: 2) | ←R -AF→ | 466 | HR- β [c] | 16237 ± 2520 (1.90x) | 55919 ± 6371 (0.90x) |
| NTC9385Ra-O2 (SEQ ID NO: 39) | ←R | 306 | HR-←AF- β | 14510 ± 835 (1.70x) | 49526 ± 2179 (0.80x) |
| NTC9385Ra-O1 dual | ←R -AF→ | 466 | HR-AF→- β | 13929 ± 1291 (1.63x) | 56552 ± 2714 (0.91x) |
| NTC9385Ra-O2 dual | ←R -AF→ | 466 | HR-←AF- β | 12543 ± 245 (1.47x) | 54379 ± 1244 (0.89x) |
| NTC9385Ra-RNAI-O1 | ←R -RNAI→ | 488 | HR-AF→- β | 15773 ± 238 (1.85x) | 55468 ± 6619 (0.89x) |
| NTC9385R-RNAI-O1 | ←R -AF→ | 466 | HR-← RNAI - β | 14296 ± 287 (1.67x) | 60630 ± 2176 (0.98x) |
| NTC9385R-RNAI-O2 | ←R -AF→ | 466 | HR- RNAI →- β | 12271 ± 466 (1.44x) | 60691 ± 6482 (0.98x) |

[a] trpA term = T; HTLV-IR = HR; B globin 3' acceptor site = β; RNA-OUT sucrose selection marker = AF; pUC origin RNAI antisense RNA = RNAI; pUC origin = P; R6K origin = R; ColE2 origin = C; BH = PAS-BH UP = upstream pUC plasmid derived DNA.
[b] EGFP plasmid DNA transfected with Lipofectamine 2000. Fluorescence units (FU) reported. Mean FU standardized to NTC8685
[c] HR β intron is 225 bp
[d] P$_{min}$ minimal pUC origin (SEQ ID NO: 42) and RNA-OUT (bacterial region = SEQ ID NO: 43)

Thus, the reader will see that the improved expression vectors of the invention provide for a rational approach to improve plasmid expression.

While the above description contains many examples, these should not be construed as limitations on the scope of the invention, but rather should be viewed as an exemplification of preferred embodiments thereof. Many other variations are possible. For example, the RNA-OUT selectable marker may be substituted with an alternative RNA-OUT sequence variant that functionally binds RNA-IN to repress expression, for example, a CpG free RNA-OUT (SEQ ID NO:36). A CpG free R6K-RNA-OUT bacterial region (SEQ ID NO:37) or CpG free ColE2-RNA-OUT bacterial region (SEQ ID NO: 38) may be utilized. Likewise, the RNA-OUT promoter and/or terminator could be substituted with an alternative promoter and/or terminator. Likewise, the ColE2-P9 or R6K replication origin may be substituted with a ColE2 related replication origin, and propagated in a strain expressing the ColE2 related replication origin replication protein. Likewise, the ColE2-P9 or R6K origin may be substituted with an origin from one of sequences, and/or immunostimulatory RNA elements as disclosed in Williams, Supra, 2008. The vectors may include a boundary element between the bacterial region and the eukaryotic region, for example, the CMV promoter boundary element upstream of the CMV enhancer (or heterologous promoter enhancer) may be included in the vector design (e.g. NTC9385R-BE; SEQ ID NO: 41). The vectors may include a eukaryotic transcriptional terminator between the bacterial region and the eukaryotic region, for example, the 4×C2 terminator or the gastrin terminator. Likewise, the vectors may utilize a diversity of RNA Pol II promoters different from the CMV promoter examples provided herein, for example, constitutive promoters such as the elongation factor 1 (EF1) promoter, the chicken β-actin promoter, the β-actin promoter from other species, the elongation factor-1α (EF1α) promoter, the phosphoglycerokinase (PGK) promoter, the Rous sarcoma virus (RSV) promoter, the human serum albumin (SA) promoter, the α-1 antitrypsin (AAT) promoter, the thyroxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EF1α) promoters, CpG free versions of the human or murine CMV-derived enhancer elements combined with the elongation factor 1α (EF1α) promoters, the albumin promoter combined with an α-fetoprotein MERII enhancer, etc, or the diversity of tissue specific or inducible promoters know in the art such as the muscle specific promoters muscle creatine kinase (MCK), and C5-12 described herein or the liver-specific promoter apolipoprotein A-I (ApoAI).

Accordingly, the scope of the invention should be determined not by the embodiments illustrated, but by the appended claims.

What is claimed is:

1. A method for heat inducible production of a Rep protein dependent replication origin plasmid vector, comprising:
   a. cloning the plasmid replication regulating Rep protein into an expression vector to create a $P_L$-Rep protein expression cassette in which said Rep protein is expressed under the control of the $P_L$ promoter and said $P_L$ promoter further comprises an OL1 mutation in which repressor binding to OL1 is decreased or lost by mutation in OL1, said OL1 mutation comprising either a single base substitution or a single base deletion within the $P_L$ promoter (−35 to −10) SEQ ID NO:10;
   b. integrating said $P_L$-Rep protein expression cassette into a host strain genome to create a $P_L$-Rep protein host strain in which expression from the said $P_L$-Rep protein expression cassette is repressed by a temperature sensitive lambda repressor expressed from the host strain genome;
   c. transforming said $P_L$-Rep protein host strain with said Rep protein dependent replication origin plasmid vector;
   d. isolating the resultant transformed bacterial cells;
   e. propagating said transformed bacterial cells at 25-32° C. to maintain the said Rep protein dependent plasmid vector at a basal copy number; and
   f. inducing said transformed bacterial cells at 37-42° C. to increase copy number of said Rep protein dependent plasmid vector.

2. The method of claim 1, wherein said $P_L$ promoter OL1 mutation comprising either a single base substitution or a single base deletion within the $P_L$ promoter (−35 to −10) SEQ ID NO:10 is selected from the group consisting of a $P_L$ promoter OL1-G (SEQ ID NO: 11), and a $P_L$ promoter OL1-G to T (SEQ ID NO: 12).

3. The method of claim 1, wherein said Rep protein dependent replication origin is selected from the group consisting of a R6K replication origin, ColE2-P9 replication origin and ColE2 related replication origin.

4. The method of claim 1, wherein said plasmid replication regulating Rep protein comprises an R6K Rep protein mutation selected from the group consisting of P42L-P113S (SEQ ID NO: 13) and P42L-P106L-F107S (SEQ ID NO: 14).

5. The method of claim 1, wherein said plasmid replication regulating Rep protein comprises a ColE2 Rep protein selected from the group consisting of ColE2 Rep protein (SEQ ID NO: 15) and ColE2 Rep protein mutation G194D (SEQ ID NO: 16).

6. The method of claim 1, wherein said $P_L$-Rep protein host strain further comprises a genomically expressed RNA-IN regulated selection marker.

7. The method of claim 1, wherein said Rep protein dependent plasmid vector for heat inducible production has a vector backbone with at least 95% sequence identity to a sequence selected from the group consisting of: SEQ ID NO: 2, SEQ ID NO: 3, SEQ ID NO: 8, SEQ ID NO: 9, SEQ ID NO: 39, SEQ ID NO: 40, and SEQ ID NO: 41.

* * * * *